US008916709B2

(12) United States Patent
Gu et al.

(10) Patent No.: US 8,916,709 B2

(45) **Date of Patent: *Dec. 23, 2014**

(54) 1,2,4-OXADIAZOLE AND 1,2,4-THIADIAZOLE β-LACTAMASE INHIBITORS

(71) Applicant: Cubist Pharmaceuticals, Inc., Lexington, MA (US)

(72) Inventors: Yu Gui Gu, Acton, MA (US); Yong He, Bedford, MA (US); Ning Yin, Lexington, MA (US); Dylan C. Alexander, Watertown, MA (US); Jason B. Cross, Acton, MA (US); Chester A. Metcalf, III, Needham, MA (US); Jon Christian Baber, Somerville, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/853,506

(22) Filed: Mar. 29, 2013

(65) Prior Publication Data

US 2013/0289012 A1 Oct. 31, 2013

Related U.S. Application Data

(60) Provisional application No. 61/618,136, filed on Mar. 30, 2012.

(51) Int. Cl.

| | |
|---|---|
| ***C07D 471/08*** | (2006.01) |
| ***A61K 31/546*** | (2006.01) |
| ***A61K 31/439*** | (2006.01) |
| ***A61K 31/545*** | (2006.01) |
| ***A61K 31/407*** | (2006.01) |
| ***A61K 45/06*** | (2006.01) |
| ***A61K 31/527*** | (2006.01) |

(52) U.S. Cl.

CPC ............ *C07D 471/08* (2013.01); *A61K 31/546* (2013.01); *A61K 31/545* (2013.01); *A61K 31/527* (2013.01); *A61K 45/06* (2013.01); *A61K 31/407* (2013.01); *A61K 31/439* (2013.01)

USPC ........... 546/183; 546/121; 514/202; 514/203; 514/300; 514/359

(58) Field of Classification Search

USPC .......................................... 546/183; 514/359

See application file for complete search history.

(56) References Cited

U.S. PATENT DOCUMENTS 7,112,592 B2 9/2006 Lampilas et al.
7,612,087 B2 11/2009 Aszodi et al.

(Continued)

FOREIGN PATENT DOCUMENTS

EP 2135959 A1 12/2009
FR 2 812 635 A1 2/2002

(Continued)

OTHER PUBLICATIONS

Patani, Chem. Rev. 1996, 96, 3147-3176.*

(Continued)

*Primary Examiner* — John Mabry
*Assistant Examiner* — Daniel Carcanague
(74) *Attorney, Agent, or Firm* — Lathrop & Gage LLP; Brian C. Trinque

(57) ABSTRACT

β-Lactamase inhibitor compounds (BLIs) are disclosed, including compounds that have activity against class A, class C or class D β-lactamases. Methods of manufacturing the BLIs, and uses of the compounds in the preparation of pharmaceutical compositions and antibacterial applications are also disclosed.

20 Claims, 5 Drawing Sheets

Table I

Compounds of Formula II

| Cmpd. No. | Z | $R^1$ | R |
|---|---|---|---|
| 801 |  | H |  |
| 802 |  | -$NH_2$ |  |
| 803 |  |  |  |
| 804 |  | H |  |
| 805 |  | -$NH_2$ |  |
| 806 |  |  |  |

(56) References Cited

U.S. PATENT DOCUMENTS

| | | | | |
|---|---|---|---|---|
| 7,732,610 | B2 | 6/2010 | Lampilas et al. | |
| 8,178,554 | B2 | 5/2012 | Lampilas et al. | |
| 8,471,025 | B2 | 6/2013 | Dedhiya et al. | |
| 8,487,093 | B2 | 7/2013 | Blizzard et al. | |
| 2011/0046102 | A1 | 2/2011 | Ledoussal et al. | |
| 2012/0016533 | A1 | 1/2012 | Lim et al. | |
| 2012/0053350 | A1 | 3/2012 | Mangion et al. | |
| 2012/0323010 | A1 | 12/2012 | Ronsheim et al. | |
| 2013/0012712 | A1 | 1/2013 | Priour et al. | |
| 2013/0059774 | A1 | 3/2013 | Patel et al. | |
| 2013/0289012 | A1 | 10/2013 | Gu et al. | |
| 2013/0296290 | A1* | 11/2013 | Gu et al. | 514/202 |
| 2013/0296291 | A1* | 11/2013 | Gu et al. | 514/202 |
| 2013/0296292 | A1* | 11/2013 | Gu et al. | 514/202 |
| 2013/0296293 | A1* | 11/2013 | Gu et al. | 514/202 |
| 2013/0296555 | A1* | 11/2013 | Gu et al. | 544/127 |
| 2013/0303504 | A1* | 11/2013 | Gu et al. | 514/202 |
| 2013/0345190 | A1* | 12/2013 | Gu et al. | 514/207 |

FOREIGN PATENT DOCUMENTS

| | | | |
|---|---|---|---|
| FR | 2 835 186 | A1 | 8/2003 |
| FR | 2 930 553 | A1 | 10/2009 |
| FR | 2 951 171 | A | 4/2011 |
| KR | 2010130176 | A | 12/2010 |
| WO | WO 02/10172 | A1 | 7/2002 |
| WO | WO 03/063864 | A2 | 8/2003 |
| WO | WO2007/129176 | A2 | 11/2007 |
| WO | WO 2009/091856 | A2 | 7/2009 |
| WO | WO2009/133442 | A1 | 11/2009 |
| WO | WO 2010/056827 | A1 | 5/2010 |
| WO | WO 2010/118361 | A1 | 10/2010 |
| WO | WO2010/126820 | A1 | 11/2010 |
| WO | WO 2011/042560 | A1 | 4/2011 |
| WO | WO2011/101710 | A1 | 8/2011 |
| WO | WO2012/086241 | A1 | 6/2012 |
| WO | WO2012/172368 | A1 | 12/2012 |
| WO | WO 2013/014496 | A1 | 1/2013 |
| WO | WO 2013/014497 | A1 | 1/2013 |
| WO | WO 2013/030735 | A1 | 3/2013 |
| WO | WO 2013/038330 | A1 | 3/2013 |

OTHER PUBLICATIONS

Dorwald, "Side Reactions in Organic Synthesis: A Guide to Successful Synthesis Design" 2005 Wiley-VCH Verlag GmbH & Co. KGaA, Wienheim, chapter 1.*

Crompton, et al: Beta-Lactamase inhibitors, the inhibition of serine beta-lactamases by specific boronic acids; Biochem J., 1988, vol. 251, pp. 453-459.

International Search Report, PCT/US2013/034562, dated Jul. 30, 2013, 6 pages.

Written Opinion, PCT/US2013/034562, dated Jul. 30, 2013, 5 pages.

Patani, et al: Bioisosterism: A Rational Approach in Drug Design; Chem Rev, 1996, vol. 96, pp. 3147-3176.

International Search Report, PCT/US2013/034589, dated Jul. 29, 2013, 4 pages.

Written Opinion, PCT/US2013/034589, dated Jul. 29, 2013, 5 pages.

Mangion, et al: A Concise Synthesis of a beta-Lactamase Inhibitor; Organic Letters, 2011, vol. 13, pp. 5480-5483.

Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 2: Synthesis and stucture—activity relationships in the S-3578 series"; Bioorganic and Medicinal Chemistry 2004, vol. 12, pp. 4211-4219.

Yoshizawa, H. et al.; "New broad-spectrum parenteral cephalosporins exhibiting potent activity against both methicillin-resistant *Staphylococcus aureus* (MRSA) and *Pseudomonas aeruginosa*. Part 3: 7b-[2-(5-Amino-1,2,4-thiadiazol-3-yl)-2-ethoxyiminoacetamido] cephalosporins bearing 4-[3-(aminoalkyl)-ureido] -1-pyridinium at C-3"; Bioorganic and Medicinal Chemistry 2004, vol. 12, pp. 4221-4231.

Yoshizawa, H. et al.; "S-3578, A New Broad Spectrum Parenteral Cephalosporin Exhibiting Potent Activity Against both Methicillin-resistant *Staphylococcus aureus* (MRSA) and *Pseudomonas aeruginosa* Synthesis and Structure-activity Relationships"; The Journal of Antibiotics 2002, vol. 55, No. 11, pp. 975-992.

Ida, T. et al. "CP6679, a new injectable cephalosporin with broad spectrum and potent activities against methicillin-resistant *Staphylococcus aureus* and *Pseudomonas aeruginosa*"; Journal of Infection and Chemotherapy 2002, vol. 8, pp. 138-144.

* cited by examiner

FIGURE 1
Table I
Compounds of Formula II
| Cmpd. No. | Z | $R^1$ | R |
|---|---|---|---|
| 801 | 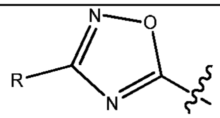 | H | 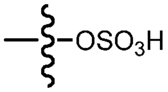 |
| 802 | 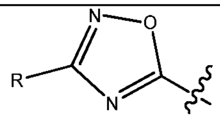 | $-NH_2$ | 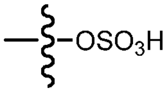 |
| 803 | 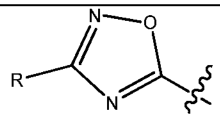 | 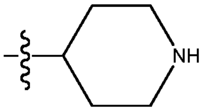 | 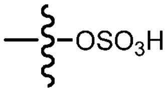 |
| 804 | 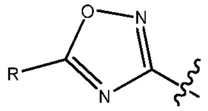 | H | 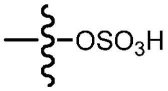 |
| 805 | 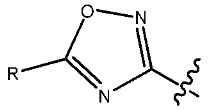 | $-NH_2$ | 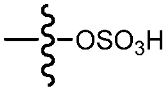 |
| 806 | 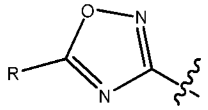 | 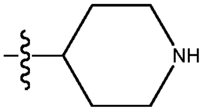 | 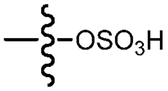 |

FIGURE 2A

Table II Standard BLI Potentiation MIC Assay Against a Panel of Isogenic and Clinical Strains Expressing β-Lactamases

| **Strain #** | **β-Lactamase** | **Bkgd** | **No BLI** | **CCC** | **801** | **802** | **804** | **805** |
|---|---|---|---|---|---|---|---|---|
| Eco.2806 | KPC-2 | isogenic | E | B | B | B | A | A |
| Pae.2808 | KPC-2 | clinical | E | C | C | C | C | C |
| Kpn.2478 | KPC-2, TEM+ | clinical | E | C | C | C | B | C |
| Kpn.2490 | KPC-3, SHV+, TEM+ | clinical | E | B | A | A | A | A |
| Kpn.2783 | CTX-M-15, SHV+, TEM+ | clinical | E | A | B | B | A | B |
| Kpn.571 | TEM-26 | clinical | D | AA | A | AA | B | A |
| Pae.2885 | AmpC | clinical | B | A | A | A | A | A |
| Cfr.568 | AmpC | clinical | E | C | C | C | B | B |
| Ecl.569 | AmpC | clinical | E | B | B | A | A | C |
| Kpn.2914 | KPC-2, SHV+ | clinical | D | B | B | B | B | B |
| Kpn.2913 | KPC-2, SHV+ | clinical | D | A | A | A | A | B |
| Kpn.2917 | KPC-2, SHV+ | clinical | D | A | A | A | A | A |
| Kpn.2918 | KPC-3, SHV+, TEM+ | clinical | E | C | C | C | B | C |
| Kpn.2909 | KPC-3, SHV+, TEM+ | clinical | E | B | C | C | B | C |
| Eco.2711 | KPC | clinical | D | A | A | A | B | A |
| Eco.2781 | KPC-2, TEM+ | clinical | C | AA | A | A | A | AA |
| Kpn.2926 | CTX-M-15, OXA-48 | clinical | E | B | B | B | B | B |
| Pae.2757 | AmpC over-expn | clinical | C | B | B | B | B | A |
| Pae.2863 | AmpC de-repress | clinical | C | B | B | B | B | B |
| Eco.2843 | DHA-1 | isogenic | E | A | A | A | AA | AA |
| Eco.2491 | CMY-2 | clinical | D | A | B | A | A | A |

FIGURE 2B

| Strain # | β-Lactamase | Bkgd | No BLI | CCC | 801 | 802 | 804 | 805 |
|---|---|---|---|---|---|---|---|---|
| Eco.2902 | Aba-ADC-33 | isogenic | E | B | B | B | B | C |
| Eco.2840 | KPC-4 | isogenic | E | D | C | D | D | D |
| Eco.2845 | OXA-15 | isogenic | E | D | C | B | C | C |
| MIC90 | | | E | C | C | C | B | C |
| MIC50 | | | E | B | B | B | A | B |

Table III: Synergy MIC (sMIC) Against a Panel of Isogenic and Clinical Strains Expressing β-lactamases

| β-Lactamase | Bkgd | Sp | β-Lactam (4 ug/mL) | CCC | 801 | 802 | 803 | 804 | 805 | 806 |
|---|---|---|---|---|---|---|---|---|---|---|
| none | isogenic | Eco | none | D | F | F | F | F | F | F |
| KPC-2 | isogenic | Eco | CXA-101 | B | A | B | B | A | B | B |
| OXA-15 | isogenic | Eco | CXA-101 | D | C` | C | | C | C | D |
| CTX-M-15 | isogenic | Eco | CXA-101 | A | B | B | C | A | B | C |
| SHV-12 | isogenic | Eco | CXA-101 | B | B | A | C | B | B | D |
| P99 | isogenic | Eco | CXA-101 | A | A | B | B | A | B | B |
| KPC-2 | clinical | Kpn | CXA-101 | C | C | C | C | C | C | C |
| KPC-2 | clinical | Pae | CXA-101 | B | C | C | C | B | C | C |

AA=< 0.25μg/mL; A = 0.25-0.5 μg/mL; B = 1-2 μg/mL; C = 4-8 μg/mL; D = 16-32 μg/mL; E = 64μg/mL; F= ≥128μg/mL

CCC is comparator compound 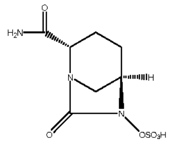

Table IV: Inhibition Kinetics for the KPC-2 β-lactamase

| | Compound | | | | | | |
|---|---|---|---|---|---|---|---|
| | **CCC** | **801** | **802** | **803** | **804** | **805** | **806** |
| Kinact/K $mM^{-1}s^{-1}$ | C | B | B | C | B | B | B |

A = 1000-5000 $mM^{-1}s^{-1}$; B = 100-999 $mM^{-1}s^{-1}$; C = 1-99 $mM^{-1}s^{-1}$

CCC is comparator compound

1,2,4-OXADIAZOLE AND 1,2,4-THIADIAZOLE β-LACTAMASE INHIBITORS

RELATED APPLICATIONS

This application claims priority to U.S. Provisional Application No. 61/618,136, filed Mar. 30, 2012. The entire content of this application is incorporated herein by reference in its entirety.

TECHNICAL FIELD

This disclosure is directed to β-lactamase inhibitors (BLIs) which are effective as inhibitors of β-lactamases and, when used in combination with β-lactam antibiotics are useful in the treatment of bacterial infections. The compounds when combined with a β-lactam antibiotic are effective in treating bacteria that are resistant to β-lactam antibiotics due to the presence of β-lactamases. Pharmaceutical compositions comprising such compounds, methods of using such compounds, and processes for preparing such compounds are also disclosed.

BACKGROUND

Bacterial resistance to β-lactam antibiotics, especially in Gram-negative bacteria, is most commonly mediated by β-lactamases. β-lactamases are enzymes that catalyze the hydrolysis of the β-lactam ring, which inactivates the antibacterial activity of the β-lactam antibiotic and allows the bacteria to become resistant. Inhibition of the β-lactamase with a BLI slows or prevents degradation of the β-lactam antibiotic and restores β-lactam antibiotic susceptibility to β-lactamase producing bacteria. Many of these β-lactamases are not effectively inhibited by BLIs currently on the market rendering the β-lactam antibiotics ineffective in treating bacteria that produce these β-lactamases. There is an urgent need for novel BLIs that inhibit β-lactamases that are not effectively inhibited by the current clinical BLIs (e.g. KPC, class C and class D β-lactamases) and that could be used in combination with β-lactam antibiotics to treat infections caused by β-lactam resistant bacteria.

SUMMARY OF INVENTION

The present invention provides, in one aspect, compounds of chemical formula (I), or pharmaceutically-acceptable salts thereof, which are BLIs and are useful in combination with β-lactam antibiotics for the treatment of bacterial infections.

A compound of Formula (I) or a pharmaceutically acceptable salt thereof:

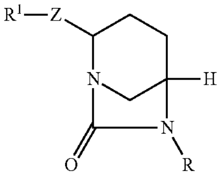

(I)

wherein

Z is selected from a 1,2,4-oxadiazole or a 1,2,4-thiadiazole;

R is selected from

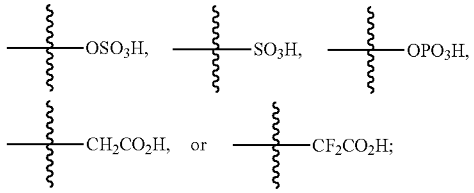

, , , or ;

and $R^1$ is selected from:

a. hydrogen, b.

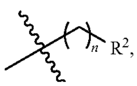

wherein $R^2$ is selected from

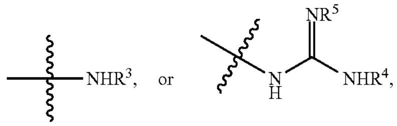

or wherein each of $R^3$, $R^4$ and $R^5$ is independently selected from hydrogen, $(C_1\text{-}C_3)$-alkyl, aminoalkyl, aminocycloalkyl, or hydroxyalkyl, and n is selected from 1, 2 or 3, c. amino, d.

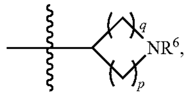

wherein $R^6$ is selected from H, $(C_1\text{-}C_3)$-unsubstituted alkyl, amino-$(C_2\text{-}C_3)$-alkyl, aminocycloalkyl, hydroxyalkyl,

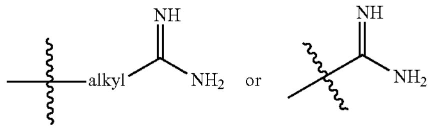

or and each of p and q is independently selected from 1 or 2; and e. —$CH_2(R^7)CH_2NH_2$ wherein $R^7$ is selected from amino or hydroxyl.

In another aspect, the invention provides use of a compound of Formula I for inhibiting β-lactamases.

In yet another aspect, the invention provides compounds of Formula I with high binding affinity for β-lactamase enzymes.

In a further aspect, the present invention also provides antibacterial compositions comprising compounds of Formula I and at least one β-lactam antibiotic.

In an even further embodiment, the present invention provides pharmaceutical compositions comprising compounds of Formula I and at least one β-lactam antibiotic and methods of use thereof.

In a still further aspect, the invention provides methods of use of the compounds of Formula Ito treat bacterial infections in a subject.

BRIEF DESCRIPTION OF THE DRAWINGS

FIG. 1 shows Table I, Representative Compounds of Formula II

FIGS. 2*a*-2*b* show Table II, Standard BLI potentiation MIC assay against a panel of isogenic and clinical strains expressing β-lactamases.

FIG. 3 shows Table III, the synergy MIC of representative compounds of Formula I against a panel of isogenic and clinical strains expressing β-lactamases.

DETAILED DESCRIPTION

Definitions

Figure 4:
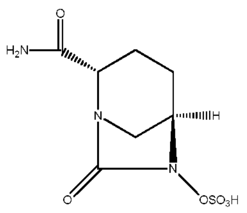
FIG. 4 shows Table IV, an assay to determine inhibition kinetics of representative compounds of Formula I for the KPC-2 β-lactamase.

Molecular terms, when used in this application, have their common meaning unless otherwise specified.

The term "alkyl" is defined as a linear or branched, saturated radical having one to about twenty carbon atoms unless otherwise specified. Preferred alkyl radicals are "lower alkyl" radicals having one to about five carbon atoms. Examples of alkyl groups include, without limitation, methyl, ethyl, tert-butyl, isopropyl, and hexyl. A subset of the term alkyl is "($C_1$-$C_3$)-unsubstituted alkyl" which is defined as an alkyl group that bears no substituent groups. Examples of ($C_1$-$C_3$)-unsubstituted alkyl groups include methyl, ethyl, propyl and isopropyl. It is understood that if a ($C_1$-$C_3$)-alkyl is "substituted" that one or more hydrogen atoms is replaced by a substitutent.

The term amino denotes a $NH_2$ radical

The term "aminoalkyl" denotes an alkyl in which one or more of the alkyl hydrogen atoms has been replaced by an amino group.

The term "aminocycloalkyl" denotes a cycloalkyl in which one of the cycloalkyl hydrogen atoms has been replaced by an amino group.

The term "cycloalkyl" or "cycloalkyl ring" is defined as a saturated or partially unsaturated carbocyclic ring in a single or fused carbocyclic ring system having from three to twelve ring members. In a preferred embodiment, a cycloalkyl is a ring system having three to seven ring members. Examples of a cycloalkyl group include, without limitation, cyclopropyl, cyclobutyl, cyclohexyl, and cycloheptyl.

The term "hydroxyalkyl" denotes an alkyl radical in which one or more of the alkyl hydrogen atoms has been replaced by a hydroxyl group.

It will be understood by one of skill in the art that a  or — denote the point of attachment of a substituent group where indicated. For example

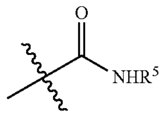

or —C(O)$NHR^5$ represent that the point of attachment of the amide moiety is at the carbonyl carbon.

The functional classification of β-lactamases and terms "Class A", "Class C", and "Class D" β-lactamases are understood by one of skill in the art and are described in "Updated Functinal Classification of β-Lactamases", Bush, K.; Jacoby, G. A.; *Antimicrob. Agents Chemother.* 2010, 54, 969-976, herein incorporated by reference.

The salts of the compounds of the invention include acid addition salts and base addition salts. In a one embodiment, the salt is a pharmaceutically acceptable salt of the compound of Formula I. The term "pharmaceutically acceptable salts" embraces salts commonly used to form alkali metal salts and to form addition salts of free acids or free bases. The nature of the salt is not critical, provided that it is pharmaceutically-acceptable. Suitable pharmaceutically acceptable acid addition salts of the compounds of the invention may be prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention by treating, for example, the compound of the invention with the appropriate acid or base.

The compounds of the invention can possess one or more asymmetric carbon atoms and are thus capable of existing in the form of optical isomers as well as in the form of racemic or non-racemic mixtures thereof. The compounds of the invention can be utilized in the present invention as a single isomer or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from the optically active salts. An alternative process for separation of optical isomers includes the use of a chiral chromatography column optimally chosen to maximize the separation of the enantiomers. Still another available method involves synthesis of covalent diastereoisomeric molecules by treating compounds of the invention with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention can likewise be obtained by utilizing optically active starting materials. These isomers may be in the form of a free acid, a free base, an ester or a salt.

The invention also embraces isolated compounds. An isolated compound refers to a compound which represents at least 10%, such as at least 20%, such as at least 50% and further such as at least 80% of the compound present in the mixture. In one embodiment, the compound, a pharmaceutically acceptable salt thereof, or a pharmaceutical composition comprising the compound exhibits detectable (i.e. statistically significant) activity when tested in conventional biological assays such as those described herein.

β-Lactamase Inhibitors (BLIs)

In one aspect, the invention provides compounds of Formula I or pharmaceutically-acceptable salts thereof:

(I)

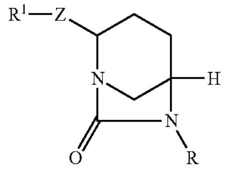

The substituent Z of Formula I is selected from a 1,2,4-oxadiazole or a 1,2,4-thiadiazole. In one aspect of the invention the substituent

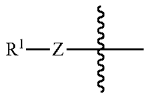

is selected from

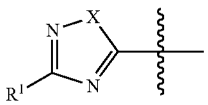

or

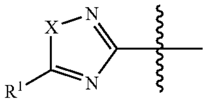

wherein X is as described previously. In another embodiment of the invention,

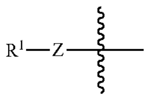

is selected from

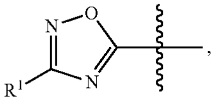
,
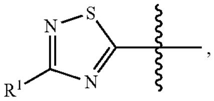
,
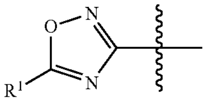
or
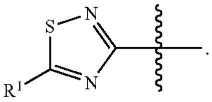
.

Substituent R of Formula I is selected from

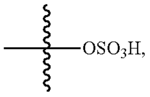
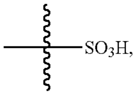
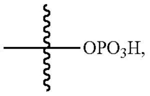
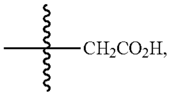
or
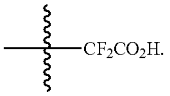

In a preferred embodiment, R is

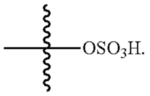

The group $R^1$ is selected from:

a. hydrogen, b.

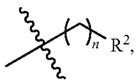

wherein $R^2$ is selected from

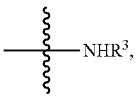
or
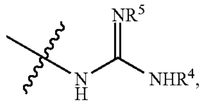

wherein each of $R^3$, $R^4$ and $R^5$ is independently selected from hydrogen, $(C_1-C_3)$-alkyl, aminoalkyl, aminocycloalkyl, or hydroxyalkyl, and n is selected from 1, 2 or 3, c. amino, d.

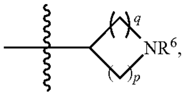

wherein $R^6$ is selected from H, $(C_1-C_3)$-unsubstituted alkyl, amino-$(C_2-C_3)$-alkyl, aminocycloalkyl, hydroxyalkyl,

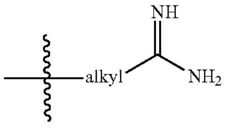
or
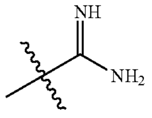

and each of p and q is independently selected from 1 or 2; and e. —$CH_2(R^7)CH_2NH_2$ wherein $R^7$ is selected from amino or hydroxyl.

In one aspect of the invention n is 1. In another aspect of the invention n is 2. In another aspect of the invention n is 3.

In one aspect of the invention $R^1$ is selected from H, $NH_2$, or,

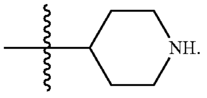 [SMILES: *C1CCNCC1]

In one embodiment of the invention, the compounds of the invention are of the stereochemistry disclosed in Formula II.

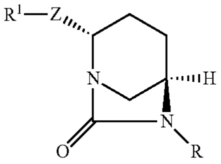
(II)

In another embodiment of the invention, Z, R and $R^1$ are chosen from the substituents listed in Table I (See FIG. 1)

Preferred compounds of Formula I are the compounds:

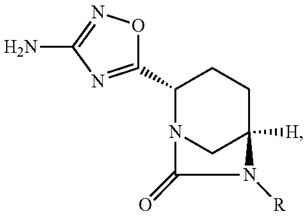
,

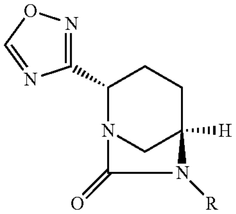
and

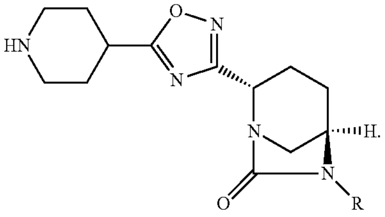
.

It will be understood by one of skill in the art that depending on the nature of $R^1$ and R, compounds of Formula I may exist in a salt or zwitterionic form.

Enzyme Inhibition and Binding Affinity

The compounds of Formula I are effective in inhibiting β-lactamase. When used in combination with β-lactam antibiotics, the compounds of Formula I potentiate the activity of the β-lactam antibiotic against microorganisms that are normally resistant to β-lactam antibiotics due to the presence of a β-lactamase or multiple β-lactamases.

In one aspect of the invention the compounds of Formula I inhibit β-lactamases selected from class A, class C or class D β-lactamases. Class A β-lactamases for example, include, but are not limited to, TEM, SHV, CTX-M, KPC, GES, VEB, SME, and GEX. In a preferred aspect of the invention, the compounds of the invention inhibit KPC β-lactamases. More preferably the compounds of the invention inhibit KPC-2 or KPC-3 β-lactamases. In one aspect of the invention, the compounds of Formula I inhibit KPC-2 or KPC-3 β-lactamases in clinical strains (FIG. 2, Table II). Class C β-lactamases for example, include, but are not limited to chromosomal AmpCs, and plasmid based ACC, DHA, CMY, FOX, ACT, MIR, LAT, MOX β-lactamases. Class D β-lactamase enzymes, for example, include, but are not limited to oxacillinases or OXA β-lactamases.

Unless otherwise indicated, the activity of the BLI compounds can be described by the MIC value obtained from a Synergy MIC assay or a BLI potentiation assay (e.g as described herein), both of which are run in the presence a β-lactam. The lower the sMIC or MIC value the more active the BLI, regardless of the mechanism of action of the BLI compound (e.g., including inhibition of β-lactamases by the BLI or any other mechanism of action or combination of mechanisms of action). The sMIC and BLI potentiation assay data supports that the compounds of Formula I potentiate (i.e. make more potent) the activity of the β-lactam antibiotic against β-lactamase producing strains by inhibiting the β-lactamase.

In one embodiment, the BLI activity is measured by growth inhibition of a β-lactamase producing bacterial strains in a Synergy MIC (sMIC) assay. Preferably, sMIC is 8 μg/mL or less. In a more preferred aspect of the invention, the sMIC is 4 μg/mL to 8 μg/mL. In an even more preferred aspect of the invention, the ssMIC is 1 to 2 μg/mL. In a still more preferred aspect of the invention, the sMIC is 0.2 to 0.5 μg/mL. Synergy MICs for representative compounds of the invention are described in Table III (See FIG. 3). It will be understood by one of skill in the art that the growth inhibition of β-lactamase producing strains can also be measured by a checkerboard synergy assay like that disclosed in International Patent Application Number WO 2008/039420 or a standard BLI potentiation assay using a fixed concentration of BLI.

In one embodiment, the BLI activity is measured by growth inhibition of a β-lactamase producing bacterial strains in a standard BLI potentiation assay using a fixed concentration of BLI. Preferably, the MIC is 8 μg/mL or less. In a more preferred aspect of the invention, the MIC is 4 to 8 μg/mL. In an even more preferred aspect of the invention, the MIC is 1 to 2 μg/mL. In a still more preferred aspect of the invention, the MIC is 0.2 to 0.5 μg/mL.

The compounds of the present invention have a broad spectrum of activity across a wide variety of β-lactamase producing bacteria. It was surprisingly found that the compounds of the present invention are active in potentiating activity of β-lactam antibiotics, in particular, Ceftolozane, against strains expressing class D β-lactamases, in particular the OXA-15 β-lactamase. Currently marketed BLIs inhibit most of the class A β-lactamases, but poorly inhibit class A KPC β-lactamases and class C β-lactamases and have variable success in inhibiting penicillinase and carbapenemase-type class D β-lactamases. The compounds of the present invention are active against a wide variety of bacterial strains that express class A and C β-lactamases and also, surprisingly are active against bacterial strains that express the class D cephalosporinase OXA-15 (Tables II and III). This increased activity against the class D β-lactamase is critical because differential effectiveness against different types of β-lactamase producing bacteria is necessary in order to effectively use β-lactam antibiotics to treat resistant strains of bacteria (vide infra).

In one embodiment, the compounds of Formula I are unexpectedly more active against bacterial strains that express OXA-15 β-lactamases than the most structurally similar compound, Avibactam (comparator compound CCC). Compounds that are more active than Avibactam are, for example, compounds 801, 802, 804, and 805.

In one embodiment, the compounds of Formula I are unexpectedly more active against and/or show broader spectrum of activity against bacterial strains that express KPC β-lactamases than the most structurally similar compound, Avibactam. Compounds that are more active than, and/or show a better spectrum of activity than Avibactam are, for example, compounds 801, 802, 804, and 805.

In another aspect of the invention, the compounds of Formula I have higher binding affinity for the β-lactamase enzyme. Consequently these compounds are better inhibitors of the β-lactamase enzyme. The inhibition kinetics of the compounds of Formula I was measured according to the procedure outlined in Example 14. The compounds of Formula I have a high binding affinity for the β-lactamase enzyme.

In one embodiment the compounds of Formula I have a binding affinity of 1000-5000 $mM^{-1}s^{-1}$.

In one embodiment the compounds of Formula I have a binding affinity of 100-999 $mM^{-1}s^{-1}$. Compounds that have a binding affinity of 100-999 $mM^{-1}s^{-1}$ are, for example, compounds 801, 802, 804, 805, and 806 (Table IV).

In one embodiment the compounds of Formula I have a binding affinity of 1-99 $mM^{-1}s^{-}$.

It was surprisingly found that the compounds of the present invention have a higher binding affinity for the β-lactamase enzyme than the closest structural comparator Avibactam (Table IV, See FIG. 4).

Pharmaceutical Compositions Comprising the Compounds of Formula I and Use Thereof Another object of the invention is pharmaceutical compositions or formulations comprising compounds of Formula I, or salts thereof, preferably further comprising a β-lactam antibiotic.

The pharmaceutical compositions can be formulated for oral, intravenous, intramuscular, subcutaneous or parenteral administration for the therapeutic or prophylactic treatment of diseases, such as bacterial infections. Preferably, the pharmaceutical composition is formulated for intravenous administration.

The pharmaceutical preparations disclosed herein may be prepared in accordance with standard procedures and are administered at dosages that are selected to reduce, prevent or eliminate infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical compositions can comprise one or more of the compounds disclosed herein, preferably a compound of Formula I in conjunction with a β-lactam antibiotic, in association with one or more nontoxic, pharmaceutically-acceptable carriers and/or diluents and/or adjuvants and/or excipients. As used herein, the phrase "pharmaceutically-acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. Non-limiting examples of carriers and excipients include corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral or parenteral administration, compounds of the present invention preferably a compound of Formula I in conjunction with a β-lactam antibiotic, can be mixed with conventional pharmaceutical carriers and excipients and used in the form of tablets, capsules, elixirs, suspensions, syrups, wafers and the like. The compositions comprising a compound of this invention may contain from about 0.1% to about 99% by weight of the active compound, such as from about 10% to about 30%.

For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions may be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs, preparations of the invention may contain conventional additives such as suspending agents, emulsifying agents, non-aqueous agents, preservatives, coloring agents and flavoring agents. Non-limiting examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, the pharmaceutical composition, preferably a compound of Formula I in conjunction with a β-lactam antibiotic, can be dissolved or suspended in any of the commonly used intravenous fluids and administered by infusion. Intravenous fluids include, without limitation, physiological saline or Ringer's solution. Intravenous administration may be accomplished by using, without limitation, syringe, mini-pump or intravenous line.

Pharmaceutical compositions of this invention for parenteral injection comprise pharmaceutically-acceptable aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, benzyl alcohol, polyols (such as glycerol, propylene glycol, and polyethylene glycol), and suitable mixtures thereof, vegetable oils (such as corn oil or olive oil), and injectable organic esters such as ethyl oleate. Proper fluidity can be maintained, for example, by the use of coating materials such as lecithin, by the maintenance of the required particle size in the case of dispersions, and by the use of surfactants. The compositions can include various buffers.

These compositions may also contain adjuvants such as preservatives, wetting agents, emulsifying agents, and dispersing agents. They may also contain taggants or other anti-counterfeiting agents, which are well known in the art. Prevention of the action of microorganisms may be ensured by the inclusion of various antibacterial and antifungal agents, for example, paraben, chlorobutanol, and phenol sorbic acid. It may also be desirable to include isotonic agents such as sugars and sodium chloride. Prolonged absorption of the injectable pharmaceutical form may be brought about by the inclusion of agents which delay absorption, such as aluminum monostearate and gelatin.

Injectable depot forms can be made by forming microencapsulating matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations can also be prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use.

Solid dosage forms for oral administration include capsules, tablets, pills, powders, and granules. Such forms may include forms that dissolve or disintegrate quickly in the oral environment. In such solid dosage forms, the active compound preferably a compound of Formula I in conjunction with a β-lactam antibiotic, can be mixed with at least one inert, pharmaceutically-acceptable excipient or carrier. Suitable excipients include, for example, (a) fillers or extenders such as starches, lactose, sucrose, glucose, mannitol, and silicic acid; (b) binders such as cellulose and cellulose derivatives (such as hydroxypropylmethylcellulose, hydroxypropylcellulose, and carboxymethylcellulose), alginates, gelatin, polyvinylpyrrolidone, sucrose, and acacia; (c) humectants such as glycerol; (d) disintegrating agents such as sodium starch glycolate, croscarmellose, agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents, such as cetyl alcohol and glycerol monostearate, fatty acid esters of sorbitan, poloxamers, and polyethylene glycols; (h) absorbents such as kaolin and bentonite clay; (i) lubricants such as talc, calcium stearate, magnesium stearate, solid polyethylene glycols, sodium lauryl sulfate, and mixtures thereof; and (j) glidants such as talc, and silicone dioxide. Other suitable excipients include, for example, sodium citrate or dicalcium phosphate. The dosage forms may also comprise buffering agents.

Solid dosage forms, including those of tablets, dragees, capsules, pills, and granules, can be prepared with coatings and shells such as functional and aesthetic enteric coatings and other coatings well known in the pharmaceutical formulating art. They may optionally contain opacifying agents and colorants. They may also be in a form capable of controlled or sustained release. Examples of embedding compositions that can be used for such purposes include polymeric substances and waxes.

The pharmaceutical compositions can be delivered using controlled (e.g., capsules) or sustained release (e.g., bioerodable matrices) delivery systems. Exemplary delayed release delivery systems for drug delivery that are suitable for administering the pharmaceutical compositions are described in U.S. Pat. No. 4,452,775 (issued to Kent), U.S. Pat. No. 5,039,660 (issued to Leonard), and U.S. Pat. No. 3,854,480 (issued to Zaffaroni).

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form.

Alternatively, delayed absorption of a parenterally administered drug form can be accomplished by dissolving or suspending the drug in an oil vehicle.

For intramuscular preparations, a sterile formulation of compounds, preferably a compound of Formula I in conjunction with a β-lactam antibiotic, or suitable soluble salt forms thereof, for example hydrochloride salts, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular, or parental formulation of compounds, preferably a compound of Formula I in conjunction with a β-lactam antibiotic, may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less. An infusion is a dose that is administered at a rate of 30 minutes or greater. In one embodiment, the infusion is one hour or greater. In another embodiment, the infusion is substantially constant.

For topical use the pharmaceutical compositions, preferably a compound of Formula I in conjunction with a β-lactam antibiotic, can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the pharmaceutical composition can be presented in liquid or semi-liquid form formulated in hydrophobic or hydrophilic bases as ointments, creams, lotions, paints or powders.

For rectal administration, the pharmaceutical compositions, preferably a compound of Formula I in conjunction with a β-lactam antibiotic, can be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the pharmaceutical compositions can be in powder form for reconstitution in the appropriate pharmaceutically acceptable carrier at the time of delivery. In another embodiment, the unit dosage form of compounds, preferably a compound of Formula I in conjunction with a β-lactam antibiotic, can be a solution of one or more compounds, or salts thereof, in a suitable diluent, in sterile hermetically sealed ampoules or sterile syringes. The concentration of the compounds, preferably a compound of Formula I in conjunction with a β-lactam antibiotic, in the unit dosage may vary, e.g. from about 1 percent to about 50 percent, depending on the compound used and its solubility and the dose desired by the physician. If the compositions contain dosage units, each dosage unit can contain from 1-500 mg of the active material. For adult human treatment, the dosage employed can range from 5 mg to 10 g, per day, depending on the route and frequency of administration.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize ar-recognized protocols for delivering the agent with the only substantial procedural modification being the substitution of the compounds of the present invention for the drugs in the art-recognized protocols. Likewise, methods for using the claimed compositions for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention, preferably in combination with a β-lactam antibiotic for the drugs in the art-recognized protocols.

Exemplary procedures for delivering an antibacterial agent are described in U.S. Pat. Nos. 6,468,967; 6,852,689; and 5,041,567, issued to Rogers and in PCT patent application number EP94/02552 (publication no. WO 95/05384), the disclosures of which are incorporated herein by reference in their entirety. In one embodiment, one or more compounds of Formula I, preferably a compound of Formula I in conjunction with a β-lactam antibiotic, or pharmaceutical compositions thereof are administered orally, rectally or via injection (intravenous, intramuscular or subcutaneous). In another embodiment, one or more compounds of Formula I, preferably a compound of Formula I in conjunction with a β-lactam antibiotic, or pharmaceutical compositions thereof are administered orally, rectally or via injection (intravenous, intramuscular or subcutaneous) to treat an infection caused by β-lactam resistant bacteria. In another embodiment, one or more compounds of Formula I, preferably a compound of Formula I in conjunction with a β-lactam antibiotic, or pharmaceutical compositions thereof are administered orally to treat an infection caused by β-lactamase producing bacteria. As used herein, the phrases "therapeutically-effective dose" and "therapeutically-effective amount" refer to an amount of a compound that prevents the onset, alleviates the symptoms, stops the progression of a bacterial infection, or results in another desired biological outcome such as, e.g., improved clinical signs or reduced/elevated levels of lymphocytes and/or antibodies. The term "treating" or "treatment" is defined as administering, to a subject, a therapeutically-effective amount of one or more compounds both to prevent the occurrence of an infection and to control or eliminate an infection. Those in need of treatment may include individuals already having a particular medical disease as well as those at risk for the disease (i.e., those who are likely to ultimately acquire the disorder). The term "subject," as used herein, refers to a mammal, a plant, a lower animal, or a cell culture. In one embodiment, a subject is a human or other animal patient in need of antibacterial treatment.

The term "administering" or "administration" and the like, refers to providing the compound of Formula I to the subject in need of treatment. Preferably the subject is a mammal, more preferably a human. The present invention comprises administering the compound of Formula I in conjunction with a β-lactam antiobiotic. When a compound of Formula I is administered in conjunction with a β-lactam antiobiotic, the compound of Formula I and the β-lactam antiobiotic can be administered at the same time or different times. When the compounds of Formula I and the β-lactam antiobiotic are administered at the same time, they can be administered as a single composition or pharmaceutical composition or they can be administered separately. It is understood that when a compound of Formula I is administered in conjunction with a β-lactam antiobiotic, that the active agents can be administered in a single combination or in multiple combinations. For example, when administered by IV, the compound of Formula I can be dissolved or suspended in any of the commonly used intravenous fluids and administered by infusion, then a β-lactam antibiotic can be dissolved or suspended in any of the commonly used intravenous fluids and administered by infusion. Conversely the β-lactam antibiotic can be dissolved or suspended in any of the commonly used intravenous fluids and administered by infusion, then a compound of Formula I can be dissolved or suspended in any of the commonly used intravenous fluids and administered by infusion. Alternatively, a pharmaceutical composition comprising a compound of Formula I and a β-lactam antibiotic can be dissolved or suspended in any of the commonly used intravenous fluids and administered by infusion.

In one embodiment of the invention, is provided a method of treating or preventing a bacterial infection comprising administering to a subject in need thereof a therapeutically-effective amount of the pharmaceutical composition comprising a compound of Formula I and a β-lactam antibiotic.

In one embodiment of the invention, is provided a method of treating or preventing a bacterial infection comprising administering to a subject in need thereof, a therapeutically-effective amount of a β-lactam antibiotic in conjunction with a compound of claim 1.

In one embodiment of the invention, is provided a method of treating or preventing a bacterial infection in a subject comprising the steps of a. administering to the subject a compound of Formula I; and b. administering a therapeutically-effective amount of a β-lactam antibiotic.

In one embodiment of the invention, is provided a method of treating or preventing a bacterial infection in a subject comprising the steps of a. administering a therapeutically-effective amount of a β-lactam antibiotic; and b. administering to the subject a compound of Formula I.

In one embodiment, the invention provides a method for treating an infection in a subject by administering a therapeutically-effective amount of one or more compounds of Formula I, preferably a compound of Formula I in conjunction with a β-lactam antibiotic, or compositions thereof. In one embodiment, the method comprises administering to a subject in need thereof a pharmaceutical composition comprising at least one of the compounds described herein, preferably a compound of Formula I in conjunction with a β-lactam antibiotic. In one embodiment, the pharmaceutical composition can comprise any one of the compounds described herein as the sole active compound or in combination with another compound, composition, or biological material. The compound may be administered orally, parenterally, by inhalation, topically, rectally, nasally, buccally, vaginally, or by an implanted reservoir, external pump or catheter. The compound may be prepared for opthalmic or aerosolized uses. The compounds of the present invention can be administered as an aerosol for the treatment of pneumonia or other lung-based infections. In one embodiment, the aerosol delivery vehicle is an anhydrous or dry powder inhaler. One or more compounds of Formula I, preferably a compound of Formula I in conjunction with a β-lactam antibiotic, or pharmaceutical compositions thereof also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In one embodiment, one or more compounds of Formula I, preferably a compound of Formula I in conjunction with a β-lactam antibiotic, are administered intravenously, subcutaneously or orally. In one embodiment for administering one or more compounds according to Formula I, preferably a compound of Formula I in conjunction with a β-lactam antibiotic to a cell culture, the one or more compounds may be administered in a nutrient medium.

In one embodiment, one or more compounds according to Formula I, preferably a compound of Formula I in conjunction with a β-lactam antibiotic, may be used to treat a subject having a bacterial infection in which the infection is caused or exacerbated by any type of bacteria, such as Gram-negative bacteria. In one aspect of the invention, the bacterial infection is caused by β-lactam resistant bacteria. In one aspect the bacterial infection is caused by β-lactamase producing bacteria. In another aspect the bacterial infection is caused by class A, class C or class D β-lactamase producing bacteria. In another aspect the bacterial infection is caused by class A β-lactamase producing bacteria. In another aspect the infection is caused by class C β-lactamase producing bacteria. In still another aspect the infection is caused by class D β-lactamase producing bacteria. In still another aspect the infection is caused by KPC β-lactamase producing bacteria. In still another aspect the infection is caused by OXA β-lactamase producing bacteria.

Representative Gram-negative pathogens known to express β-lactamases include, but are not limited to *Acinetobacter* spp. (including *Acinetobacter* baumannii), *Citrobacter* spp., *Escherichia* spp. (including *Escherichia coli*), *Haemophilus influenzae, Morganella morganii, Pseudomonas aeruginosa, Klebsiella* spp. (including *Klebsiella pneumoniae*), *Enterobacter* spp. (including *Enterobacter cloacae* and *Enterobacter aerogenes*), *Pasteurella* spp., *Proteus* spp. (including *Proteus mirabilis*), *Serratia* spp. (including *Serratia marcescens*), and *Providencia* spp. Bacterial infections can be caused or exacerbated by Gram-negative bacteria including strains which express β-lactamases that may confer resistance to penicillins, cephalosporins, monobactams and/or carbapenems. The co-administration of a novel BLIs that inhibits these β-lactamases with a β-lactam antibiotic could be used to treat infections caused β-lactam resistant bacteria.

In one aspect of the invention the infection is caused by a β-lactamase producing bacteria selected from *Acinetobacter* spp, *Citrobacter* spp, *Escherichia coli, Enterobacter cloacae*), *Haemophilus influenzae, Pseudomonas aeruginosa, Proteus mirabilis, Serratia marcescens*, and *Klebsiella pneumoniae,*

β-Lactam antibiotics that may be co-administered with compounds of Formula I include, but are not limited to cephalosporin, carbapenem, monobactam, penem and penicillin classes of antibiotics.

In one embodiment of the invention, the β-lactam antibiotic is a cephalosporin. Examples of cephalosporins include, but are not limited to, Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefinetazole, Cefonicid, Cefotetan, Cefoxitin, Cefprozil (cefprozil), Cefuroxime, Cefuzonam, Cefcapene, Cefdaloxime, Cefdinir, Cefditoren, Cefetamet, Cefixime, Cefinenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefinepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef and Ceftolozane. In one embodiment the cephalosporin is Ceftolozane or Ceftazidime.

In one embodiment of the invention, the β-lactam antibiotic is a carbapenen. Examples of carbapenem antibiotics include, but are not limited to, Imipenem, Imipenem/Cilastatin, Biapenem, Doripenem, Meropenem, Ertapenem and Panipenem. In one embodiment the Carbapenem is Imipenem/Cilastatin or Meropenem.

In one embodiment of the invention, the β-lactam antibiotic is a monobactam. Examples of monobactam antibiotics include, but are not limited to Aztreonam, Tigemonam, Carumonam, BAL30072 and Nocardicin A.

In one embodiment of the invention, the β-lactam antibiotic is a penem.

In one embodiment of the invention, the β-lactam antibiotic is a penicillin. Examples of penicillin antibiotics include, but are not limited to Amoxicillin, Ampicillin, Azlocillin, Mezlocillin, Apalcillin, Hetacillin, Becampicillin, Carbenicillin, Sulbenicillin, Ticarcillin, Piperacillin, Azlocillin, Mecillinam, Pivmecillinam, Methicillin, Ciclacillin, Talampicillin, Aspoxicillin, Oxacillin, Cloxacillin, Dicloxacillin, Flucloxacillin, Nafcillin and Pivampicillin.

The pharmaceutical compositions, preferably a compound of Formula I in conjunction with a β-lactam antibiotic, can be used to treat a bacterial infection of any organ or tissue in the body caused by β-lactam resistant bacteria, preferably, Gram-negative β-lactam resistant bacteria. These organs or tissue include, without limitation, skeletal muscle, skin, bloodstream, kidneys, heart, lung and bone. For example, a pharmaceutical composition comprising at least one compound of Formula (I), preferably a compound of Formula I in conjunction with a β-lactam antibiotic, can be administered to a subject to treat, without limitation, skin and soft tissue infections (e.g., complex skin infections), bacteremia, intra-abdominal infections and urinary tract infections (e.g., cUTI). In addition, a compound of Formula (I) may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *Pseudomonas aeruginosa*. At least one compound of Formula (I), preferably a compound of Formula I in conjunction with a β-lactam antibiotic, can be administered to a subject to treat mixed infections that comprise different types of Gram-negative bacteria, or which comprise both Gram-positive and Gram-negative bacteria. These types of infections include intra-abdominal infections and obstetrical/gynecological infections. At least one compound of Formula (I), preferably a compound of Formula I in conjunction with a β-lactam antibiotic, may also be administered to a subject to treat an infection including, without limitation, endocarditis, nephritis, septic arthritis, intra-abdominal sepsis, bone and joint infections and osteomyelitis. At least one compound of Formula (I), preferably compound of Formula I in conjunction with a β-lactam antibiotic, or pharmaceutical compositions thereof, may also be directly injected or administered into an abscess, ventricle or joint. Pharmaceutical compositions administered as an aerosol for the treatment of pneumonia or other lung-based infections. In one embodiment, the aerosol delivery vehicle is an anhydrous, liquid or dry powder inhaler.

Actual dosage levels of active ingredients in the pharmaceutical compositions of one or more compounds according to Formula I, preferably a compound of Formula I in conjunction with a β-lactam antibiotic, may be varied so as to obtain a therapeutically-effective amount of the active compound(s) to achieve the desired therapeutic response for a particular patient, compositions, and mode of administration. The effective amount can be determined as described herein. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In one embodiment, the data obtained from the assays can be used in formulating a range of dosage for use in humans. It will be understood by one of skill in the art that the when the composition comprises a compound of Formula I and a β-lactam antibiotic, both the compound of Formula I and the β-lactam antibiotic are active compounds.

The method comprises administering to the subject an effective dose of one or more compounds of Formula I, preferably in conjunction with a β lactam antibiotic. An effective dose of a compound of Formula I is generally between 125 mg/day to 2000 mg/day. In one embodiment, an effective dose is from about 0.1 to about 100 mg/kg of one or more compounds of Formula I or pharmaceutically acceptable salts thereof. In one embodiment, the dose is from about 0.1 to about 50 mg/kg of one or more compounds of Formula I or pharmaceutically acceptable salts thereof. In another embodiment, the dose is from about 1 to about 25 mg/kg of one or more compounds of Formula I or pharmaceutically acceptable salts thereof. In another embodiment, the dose is from about 1 to about 12 mg/kg of one or more compounds of Formula I. In another embodiment, the dose is about 1, 2, 3, 4, 5, 6, 7, 8, 9, 10, 11, or 12 mg/kg of one or more compounds of Formula I. In another embodiment, the compounds of Formula I are administered to a human at a dose of 100 mg to 1000 mg per dose up to four times per day. In another embodiment, the compounds of Formula I are administered to a human at a dose of 125 mg to 750 mg per dose up to four times per day. In another embodiment, the compounds of Formula I are administered to a human at a dose of 250 mg to 500 mg per dose up to four times a day. An effective dose for cell culture is usually between about 0.1 and about 1000 μg/mL. In one embodiment, the effect dose for cell culture is between about 0.1 and about 200 μg/mL.

In one embodiment, a β-lactam antibiotic and a compound of Formula I are administered in ratio of 1:4 to 8:1 antibiotic: Formula I compound. In one embodiment the ratio is 1:4. In another embodiment the ratio is 3:4. In another embodiment the ratio is 5:4. In another embodiment the ratio is 7:4. In another embodiment the ratio is 1:2. In another embodiment the ratio is 3:2. In another embodiment the ratio is 5:2. In another embodiment the ratio is 7:2. In another embodiment the ratio is 1:3. In another embodiment the ratio is 2:3. In another embodiment the ratio is 4:3. In another embodiment the ratio is 5:3. In another embodiment the ratio is 7:3. In another embodiment the ratio is 1:2. In another embodiment the ratio is 3:2. In another embodiment the ratio is 5:2. In another embodiment the ratio is 7:2. In another embodiment the ratio is 1:1. In another embodiment the ratio is 2:1. In another embodiment the ratio is 3:1. In another embodiment the ratio is 4:1. In another embodiment the ratio is 5:1. In another embodiment the ratio is 6:1. In another embodiment the ratio is 7:1. In another embodiment the ratio is 8:1. It will be understood by one of skill in the art that the β-lactam antibiotic and compound of Formula I can be administered within the range of ratios provided regardless of the method of drug delivery. It will also be understood by one of skill in the art that the β-lactam antibiotic and compound of Formula I can be administered within the range of ratios provided together, for example, in a pharmaceutical composition, or sequentially, i.e. the β-lactam antibiotic is administered, followed by administration of a compound of Formula I or vice versa.

One or more compounds of Formula I may also be administered in the diet or feed of a patient or animal. If administered as part of a total dietary intake, the amount of compound employed can be less than 1% by weight of the diet, such as no more than 0.5% by weight. The diet for animals can be normal foodstuffs to which the compound can be added or it can be added to a premix.

One or more compounds of Formula I, preferably a compound of Formula I in conjunction with a β-lactam antibiotic, can be administered as a single daily dose or in multiple doses per day. In one embodiment, one or more compounds of Formula I, preferably a compound of Formula I in conjunction with a β-lactam antibiotic, is administered as a single dose per day. In another embodiment, one or more compounds of Formula I, preferably a compound of Formula I in conjunction with a β-lactam antibiotic is administered as two equal doses per day. In another embodiment, the compounds of Formula I, preferably a compound of Formula I in conjunction with a β-lactam antibiotic is administered in three equal doses per day. In another embodiment, the compounds of Formula I, preferably a compound of Formula I in conjunction with a β-lactam antibiotic is administered in four equal doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound and the microorganism or microorganisms involved in the infection. The treatment regimen for one type of infection may differ greatly from the treatment regimen of another infection. For example, one type of infection may require administration via intravenous administration once daily, while another infection may require a treatment regimen of multiple dosing orally.

One or more compounds of Formula I, preferably a compound of Formula I in conjunction with a β-lactam antibiotic, may be administered according to this method until the bacterial infection is eradicated or reduced. In one embodiment, one or more compounds of Formula I, preferably a compound of Formula I in conjunction with a β-lactam antibiotic, are administered for a period of time from 3 days to 6 months. In another embodiment, one or more compounds of Formula I, preferably a compound of Formula I in conjunction with a β-lactam antibiotic, are administered for 7 to 56 days. In another embodiment, one or more compounds of Formula I, preferably a compound of Formula I in conjunction with a β-lactam antibiotic, are administered for 7 to 28 days. In a further embodiment, one or more compounds of Formula I, preferably a compound of Formula I in conjunction with a β-lactam antibiotic, are administered for 7 to 14 days. Compounds of the present invention may be administered for a longer or shorter time period if it is so desired.

Other embodiments of the invention include:

A pharmaceutical composition comprising a compound of Formula I and at least 1 β-lactam antibiotic or a pharmaceutically acceptable salt thereof.

A pharmaceutical composition comprising a compound of Formula I and at least 1 cephalosporin antibiotic or a pharmaceutically acceptable salt thereof.

A pharmaceutical composition comprising a compound of Formula I and Ceftolozane antibiotic or a pharmaceutically acceptable salt thereof.

A pharmaceutical composition comprising a compound of Formula I and at least 1 carbapenem antibiotic or a pharmaceutically acceptable salt thereof.

A pharmaceutical composition comprising a compound of Formula I and at least 1 monobactam antibiotic or a pharmaceutically acceptable salt thereof.

The embodiments described herein provide compounds of Formula I that are novel and active β-lactamase inhibitors. Other embodiments described herein provide novel compounds of Formula I in conjunction with β-lactam antibiotics for treatment of infections. Further embodiments described herein provide novel compounds of Formula I that show unexpected activity against β-lactamases that other compounds in the class do not have.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

Preparation of Compounds of Formula I

A compound of formula (I) can be prepared by a variety of synthetic routes, including synthetic schemes described herein. These synthetic routes can be applied to large scale synthesis with appropriate adjustment of reaction sequence, reaction conditions, isolation/purification methods and choice of solvents which are environmentally friendly and cost-effective.

The following abbreviations have the following meanings unless otherwise indicated. Abbreviations not defined below have their generally accepted meaning.

Bn=benzyl
Boc=tert-butoxycarbonyl
$Boc_2O$=di-tert-butyldicarbonate
Burgess reagent=methyl N-triethylammoniumsulfonyl) carbamate
CDI=carbonyldiimidazole
CFU=colony-forming units
CLSI=Clinical Laboratory Standards Institute
cSSSI=complicated skin and skin structure infections
DBU=1,8-diazabicyclo[5.4.0]undec-7-ene
DCM=dichloromethane
DEAD=diethyl azodicarboxylate
DIAD=diisopropyl azodicarboxylate
DIPEA=diisopropylethylamine
DMF=N,N-dimethylformamide
DMAc=N,N-dimethylacetamide
DMSO=dimethyl sulfoxide
EDCI=1-ethyl-3-(3'-dimethylaminopropyl)carbodiimide
ELSD=evaporative light scattering detector
EtOAc=ethyl acetate
ESI-MS=electrospray ionization mass spectrometry
Fmoc=Fluorenylmethyloxycarbonyl
HAP=Hospital-Acquired Pneumonia
HATU=2-(7-aza-1H-benzotriazole-1-yl)-1,1,3,3-tetramethyluronium hexafluorophosphate
HCl=hydrochloride
HOBt=1-hydroxybenzotrizole
Hrs=hours
HPLC=high performance liquid chromatography
Hunig's base=N,N-Diisopropylethylamine
Lawesson's reagent=2,4-bis(4-methoxyphenyl)-1,3,2,4-dithiadiphosphetane-2,4-disulfide
MIC=minimum inhibitory concentration
mL=milliliter
MS=mass spectrometry
MRSA=methicillin-resistant *Staphylococcus aureus*
NMR=nuclear magnetic resonance
Ns=nitrobenzenesulfonyl
Pa=*Pseudomonas aeruginosa*
Prep=preparative
Ppm=parts per million
sat.=saturated
rt=room temperature
TBAF=tetrabutylammonium fluride
TBS=t-butyldimethylsilyl
TES=triethylsilyl
TEA=triethylamine
TEMPO=2,2,6,6-tetramethyl-1-piperidinyloxy, free radical
THF=tetrahydrofuran
TFA=trifluoroacetic acid
TMS=trimethylsilyl
TLC=thin layer chromatography
VAP=Ventilator-Associated Pneumonia The compounds of Formula (I) can be prepared from intermediate 1 or 7, according to the following reaction schemes and examples, or modifications thereof, using readily available starting materials, reagents and conventional synthetic procedures including, for example, procedures described in U.S. Pat. No. 7,112,592 and WO2009/091856. As depicted in Scheme 1, compound 3 can be synthesized following standard heterocyclic ring formation chemistry under appropriate reaction conditions from ester intermediate 1, or its corresponding derivatives, such as carboxylic acid derivative 2a and aldehyde derivative 2b (see, e.g., Jakopin, Z.; Dolenc, M. S. *Curr. Org. Chem.* 2008, 12, 850-898, hereafter Jakopin; Walker, D. G.; Brodfuehrer, P. R.; Brundidge, S. P. Shih, K. M.; Sapino, C. Jr. *J. Org. Chem.* 1988, 53, 983-991 hereafter Walker and references cited therein).

It may be necessary to protect certain functionalities in the molecule depending on the nature of the $R^1$ group. Protecting these functionalities should be within the expertise of one skilled in the art. See, e.g. P. G. M. Wuts and T. W. Greene, *Protective Groups in Organic Synthesis*, Fourth Edition, John Wiley and Sons, 2006, hereafter Greene.

Scheme 1

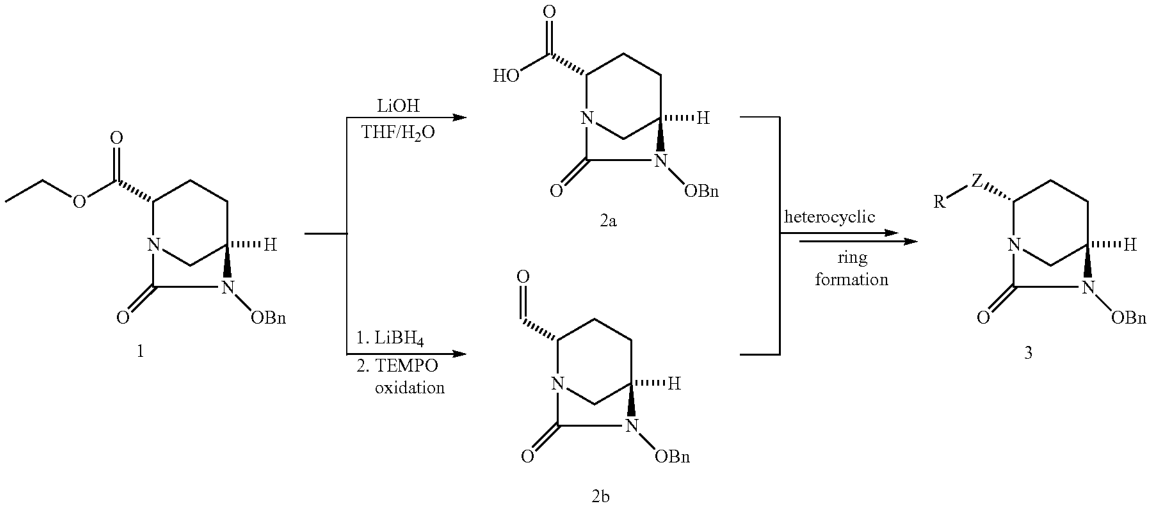

Alternatively, compound 3 can be synthesized from intermediate 7 as shown in Scheme 2. Monocyclic ester intermediate 7 can be converted to 8 under standard Mitsunobu reaction conditions. Compound 9 can then be prepared following standard heterocyclic ring formation chemistry under appropriate reaction conditions from ester intermediate 8, or its corresponding derivatives (see, e.g., Jakopinand Walker and references cited therein). Deprotection of N-Ns group in compound 9 provides compound 10, which can be converted to compound 11 by treating with diphosgene. Compound 3 can be obtained upon deprotection of N-Boc group from compound 11 under appropriate conditions, such as 4M HCl in dioxane, and subsequent treatment with base, such as $NEt_3$. Alternatively, deprotection of N-Boc and N-Ns groups in compound 11 under appropriate conditions provides bis-amine derivative 12, which can then be cyclized to form compound 3 by treatment with diphosgene or triphogene, under appropriate conditions.

Scheme 2

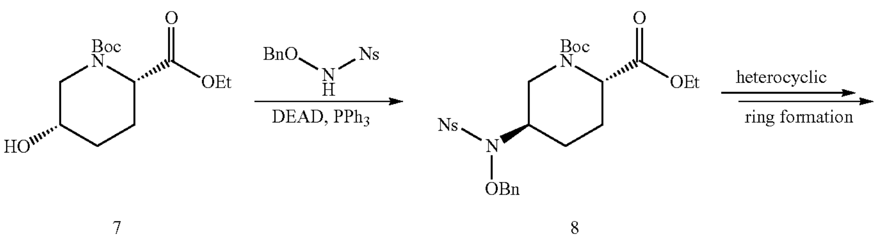

-continued

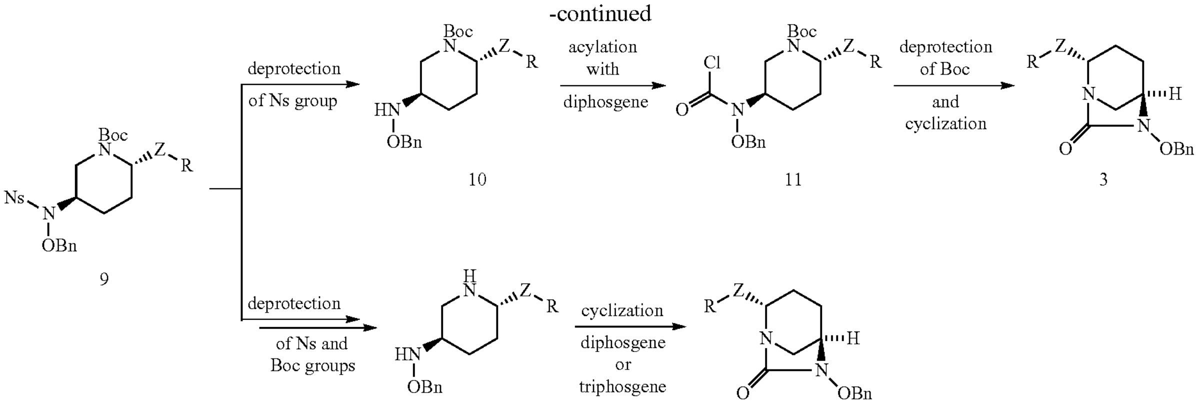

9 10 11 3 12 3

The benzylic ether protecting group in 3 can be removed via standard hydrogenolysis conditions, such as, but not limited to, $Pd/H_2$ in MeOH or THF or by acid-catalyzed hydrolysis, such as, but not limited to, $BCl_3$ in DCM to provide the hydroxy-urea intermediate 4, which can be used directly in the next step without further purification. Sulfation of 4 can be achieved by treatment with a sulfating reagent, such a, but not limited to, $SO_3$.pyridine complex, in an appropriate solvent, such as pyridine, DMF or DMAc at a temperature of 0-80° C., preferable at room temperature. Compound 5 can then be isolated and purified via conventional methods. For example, 5 can be purified by standard reverse phase prep-HPLC using appropriate buffer system, i.e. ammonium formate buffer. In some cases, 5 can be purified by normal phase silica gel chromatography after converting to an appropriate salt form, such as sulfate tetrabutyl ammonium salt. The tetrabutyl ammonium salt can be converted to a sodium salt by cation exchange. When protecting group(s) are present in the sidechain (i.e. Boc or Fmoc for amine and guanidine protection, TBS or TES for alcohol protection, etc), a deprotection step is needed to convert 5 to its final product 6, which can be purified by reverse phase prep-HPLC using the conditions mentioned above. For example, for N-Boc deprotection, 5 can be treated with an acid, such as TFA, in an appropriate solvent, such as DCM at a temperature of 0-30° C., preferable at 0° C. to rt to give 6. For an O-TBS, or O-TES deprotection, a fluoride reagent such as HF.pyridine, $HF.NEt_3$, or TBAF can be used. For an Fmoc deprotection, amines, such as diethylamine, DBU, piperidine, etc can be used.

Scheme 3

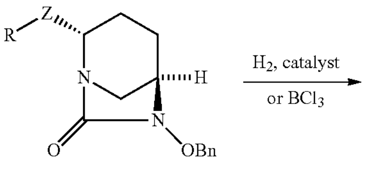

3

-continued

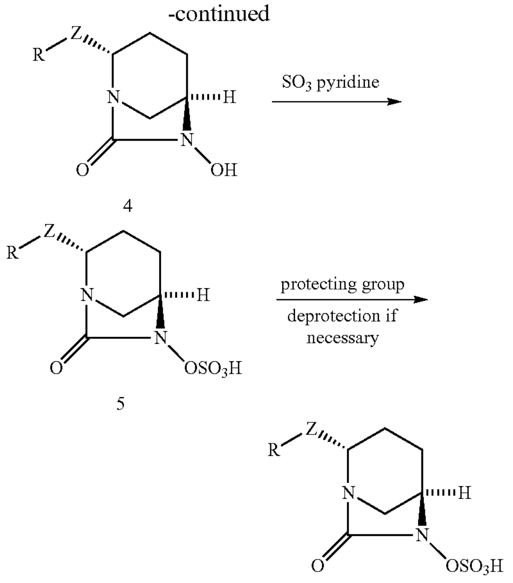

4 5 6

EXAMPLES

The specific examples which follow illustrate the synthesis of certain compounds. The methods disclosed may be adopted to variations in order to produce compounds of Formula (I), but not otherwise specifically disclosed. Further, the disclosure includes variations of the methods described herein to produce the compounds of Formula (I) that would be understood by one skilled in the art based on the instant disclosure.

All temperatures are understood to be in Centigrade (C) when not specified. The nuclear magnetic resonance (NMR) spectral characteristics refer to chemical shifts (γ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), singlet (s), multiplet (m), doublet (d), quartet (q), doublet of doublet (dd), doublet of triplet (dt), and doublet of quartet (dq). The solvents employed for taking NMR spectra are DMSO-d6 (perdeuterodimethysulfoxide), $D_2O$ (deuterated water), $CDCl_3$ (deuterochloroform) and other conventional deuterated solvents. The prep-HPLC conditions are: Waters SunFire® C18 (30×100 mm, 5 μm OBD) column; flow rate: 30-80 mL/minute, ELSD or Mass-triggered fraction collection; sample loading: Each injection loading varied from 30-300 mg for different crude samples depending on their solubility and purity profiles; Solvent system using ammonium formate buffer: solvent A: water with 20 mM ammonium formate, solvent B: 85% of acetonitrile in water with 20 mM ammonium formate. Solvent system using $NH_4HCO_3$ buffer: solvent A: water with 10 mM $NH_4HCO_3$, solvent B: acetonitrile. Solvent system using $NH_4OH$ buffer: solvent A: water with 0.1% $NH_4OH$, solvent B: acetonitrile with 0.1% $NH_4OH$.

Example 1

Synthesis of (2S,5R)-ethyl 6-(benzyloxy)-7-oxo-1,6-diazabicyclo[3.2.1]octane-2-carboxylate (Intermediate Compound 1)

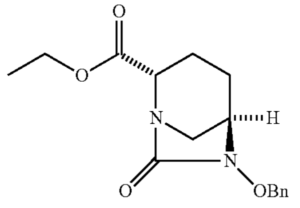

1

Step 1: Synthesis of (S)-1-tert-butyl 2-ethyl 5-oxopiperidine-1,2-dicarboxylate Method A:

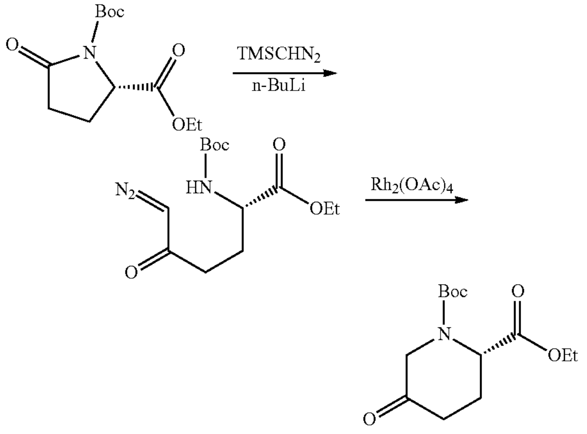

n-BuLi was added dropwise to a solution of $TMSCHN_2$ (690 mL, 1.38 mol) in dry THF (3 L) (600 mL, 1.5 mol) at −78° C., and the mixture was stirred at −78° C. for 30 minutes. The mixture was then transferred to a solution of (S)-1-tert-butyl 2-ethyl 5-oxopyrrolidine-1,2-dicarboxylate (300 g, 1.17 mol) in dry THF (3 L) via cannula, and the mixture was stirred at −78° C. for 30 minutes. The reaction mixture was then quenched with sat. $NH_4Cl$ solution, and extracted with DCM three times. The combined organic layer was concentrated in vacuum and the crude product was purified by silica gel column chromatography (3:1 petroleum ether:EtOAc) to afford (S)-ethyl 2-((tert-butoxycarbonyl)amino)-6-diazo-5-oxohexanoate (262 g, 75%) as a yellow solid.

A solution of (S)-ethyl 2-((tert-butoxycarbonyl)amino)-6-diazo-5-oxohexanoate (350 g, 1.18 mol) in DCM (1500 mL) was added to a solution of $Rh_2(OAc)_4$ (3.5 g, 7.9 mmol) in DCM (750 mL) at 0° C. The reaction was then stiffed at 20° C. overnight and then concentrated in vacuum. The crude sample was purified by silica gel column chromatography (5:1 petroleum ether/EtOAc) to afford (S)-1-tert-butyl 2-ethyl 5-oxopiperidine-1,2-dicarboxylate (175.9 g, 55%) as a yellow oil.

Method B:

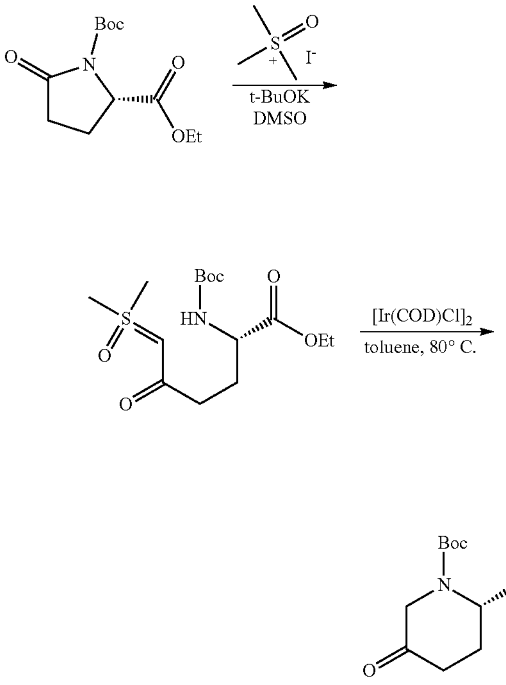

t-BuOK (330 g, 2.9 mol) was added to a solution of trimethylsulfoxonium iodide (750 g, 3.5 mol) in dry DMSO (3 L) and the mixture was stirred at rt for 1 h. (S)-1-tert-Butyl 2-ethyl 5-oxopyrrolidine-1,2-dicarboxylate (900 g, 3.5 mol) was added and the mixture was stirred at rt for 2-3 hrs. Water was added to quench the reaction and the mixture was extracted with EtOAc 5 times. The combined organic layer was concentrated in vacuum and the crude sample was purified by silica gel column chromatography (1:1petroleum ether/EtOAc then 1:10 MeOH/DCM) to afford sulfoxonium ylide intermediate (977 g, 80%) as a white solid.

A solution of sulfoxonium ylide intermediate (156 g, 0.446 mol) and $[Ir(COD)Cl]_2$ (3 g, 4.46 mmol) in toluene (4 L) was degassed by bubbling nitrogen through the solution for 10 minutes. The reaction mixture was heated to 80-90° C. for 2-3 hrs and then cooled to 20° C. Then toluene was concentrated in vacuum, the residue was purified by silica gel column chromatography (gradient elution 10:1 to 3:1 petroleum ether/EtOAc) to afford (S)-1-tert-butyl 2-ethyl 5-oxopiperidine-1,2-dicarboxylate (140 g, 57.8%) as a yellow oil.

Step 2: Synthesis of (2S,5S)-1-tert-butyl 2-ethyl 5-hydroxypiperidine-1,2-dicarboxylate

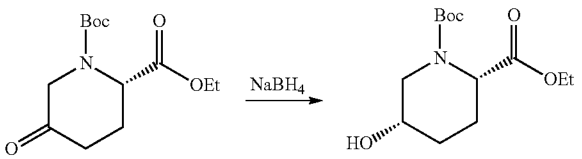

$NaBH_4$ (36 g, 1.0 mol) was added in portions to a solution of (S)-1-tert-butyl 2-ethyl 5-oxopiperidine-1,2-dicarboxylate (250 g, 0.92 mol) in EtOH (1500 mL) at −40° C. The reaction mixture was then stiffed at −40° C. for 0.5 hr then quenched with 10% HOAc solution. After diluting with water, the mixture was extracted with DCM three times. The combined organic layer was concentrated in vacuum and purified by silica gel column chromatography (1:1 petroleum ether/EtOAc) to afford (2S,5S)-1-tert-butyl 2-ethyl 5-hydroxypiperidine-1,2-dicarboxylate (205 g, 80%) as a yellow oil.

Step 3: Synthesis of (2S,5R)-1-tert-butyl 2-ethyl 5-(N-(benzyloxy)-2-nitrophenylsulfonamido)piperidine-1,2-dicarboxylate

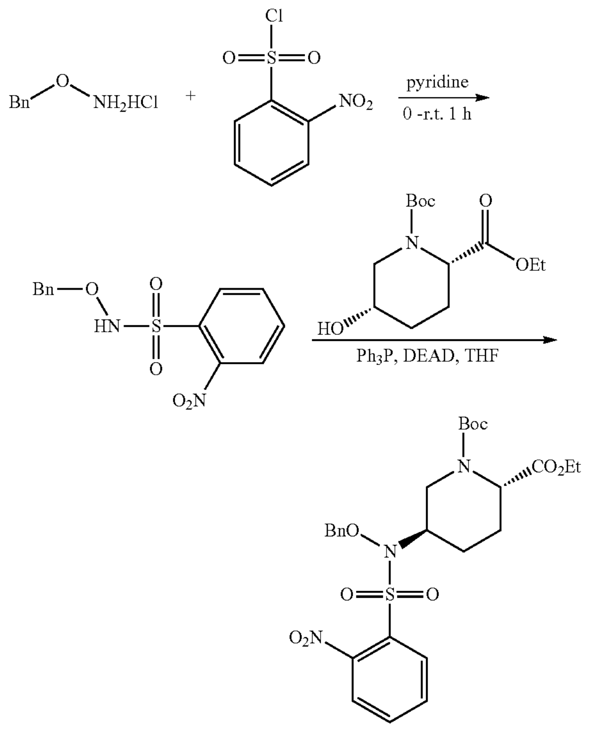

A solution of 2-nitrobenzene-1-sulfonyl chloride (500 g, 2.26 mol) in pyridine (1500 mL) was added dropwise to a solution of O-benzylhydroxylamine hydrochloride (400 g, 2.51 mol) in pyridine (1500 mL) at 0° C. The reaction mixture was then stirred at 20° C. overnight. The mixture was concentrated in vacuum, diluted with DCM and washed with HCl (10%) three times. The combined organic layer was concentrated in vacuum and re-crystallized with DCM to afford N-(benzyloxy)-2-nitrobenzenesulfonamide (485 g, 62.6%) as a yellow solid.

To a solution of N-(benzyloxy)-2-nitrobenzenesulfonamide (212 g, 0.69 mol) in THF (1000 mL) was added (2S, 5S)-1-tert-butyl 2-ethyl 5-hydroxypiperidine-1,2-dicarboxylate (171 g, 0.63 mol) and $PPh_3$ (275 g, 1.05 mol), followed by dropwise addition of a solution of DEAD (195 g, 1.12 mol) in THF (500 mL). The mixture was then stirred at 20° C. overnight. The reaction mixture was then concentrated in vacuum and purified by silica gel column chromatography (3:1 petroleum ether/EtOAc) to afford (2S,5R)-1-tert-butyl 2-ethyl 5-(N-(benzyloxy)-2-nitrophenylsulfonamido)piperidine-1,2-dicarboxylate (283.8 g, 80%) as a yellow oil.

Step 4: Synthesis of (2S,5R)-1-tert-butyl 2-ethyl 5-((benzyloxy)amino)piperidine-1,2-dicarboxylate

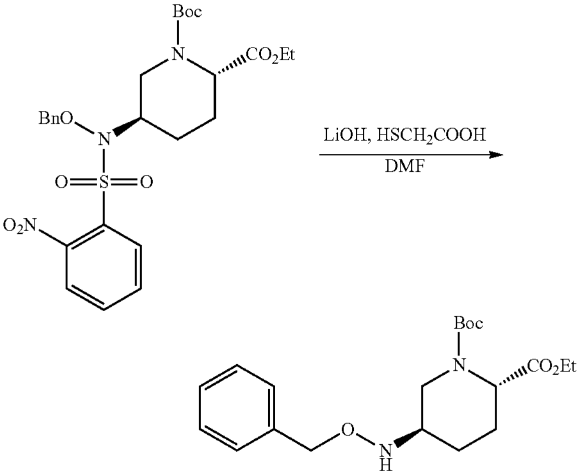

$LiOH.H_2O$ (95 g, 2.3 mol) and 2-mercaptoacetic acid (124 g, 1.3 mol) were added to a solution of (2S,5R)-1-tert-butyl 2-ethyl 5-(N-(benzyloxy)-2-nitrophenylsulfonamido)piperidine-1,2-dicarboxylate (251 g, 0.45 mol) in DMF (1200 mL). The reaction mixture was then stirred at 20° C. overnight. The reaction mixture was diluted with water and extracted with EtOAc (3×). The combined organic layer was washed with brine (3×), concentrated in vacuum and purified by silica gel column chromatography (3:1 petroleum ether/EtOAc) to afford (2S,5R)-1-tert-butyl 2-ethyl 5-((benzyloxy)amino)piperidine-1,2-dicarboxylate (122.9 g, 85%) as a yellow solid.

Step 5: Synthesis of (2S,5R)-ethyl 5-((benzyloxy)amino)piperidine-2-carboxylate

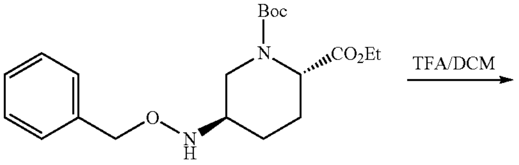

-continued

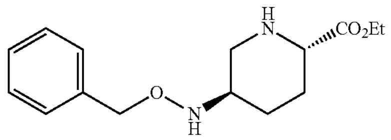

TFA (600 mL) was added to a solution of (2S,5R)-1-tert-butyl 2-ethyl 5-((benzyloxy)amino)piperidine-1,2-dicarboxylate (263 g, 0.7 mol) in DCM (600 mL) at 20° C. The mixture was stiffed at rt overnight and then concentrated in vacuum. The crude product was adjusted to pH 10 with sat. $NaHCO_3$ solution, and then extracted with DCM three times. The combined organic layer was concentrated in vacuum and purified by silica gel column chromatography (20:1 DCM/MeOH) to afford (2S,5R)-ethyl 5-((benzyloxy)amino)piperidine-2-carboxylate (184.9 g, 95%) as a yellow oil.

Step 6: Synthesis of (2S,5R)-ethyl 6-(benzyloxy)-7-oxo-1,6-diazabicyclo[3.2.1]octane-2-carboxylate

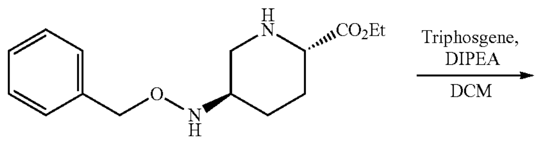

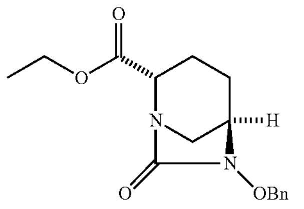

Triphosgene (21.3 g, 72 mmol) was added in portions to a solution of (2S,5R)-ethyl 5-((benzyloxy)amino)piperidine-2-carboxylate (50 g, 0.18 mol) and DIPEA (128 mL, 0.72 mol) in DCM (2000 mL) at 0° C. After stiffing at 20° C. overnight, the reaction mixture was washed with $H_3PO_4$ (10%), sat. $NaHCO_3$ and saturated NaCl. The combined organic layer was concentrated in vacuum and purified by silica gel column chromatography (3:1 petroleum ether/EtOAc) to afford (2S,5R)-ethyl 6-(benzyloxy)-7-oxo-1,6-diazabicyclo[3.2.1]octane-2-carboxylate (27.4 g, 50%) as a yellow solid.

$^1H$ NMR (400Mz, $CDCl_3$): δ 7.43-7.36 (m, 5H), 5.06 (d, J=11.4 Hz, 1H), 4.90 (d, J=11.4 Hz, 1H), 4.24 (q, J=7.1 Hz, 2H), 4.11-4.08 (m, 1H), 3.32-3.31 (m, 1H), 3.08-3.05 (m, 1H), 2.93 (d, J=11.9 Hz, 1H), 2.14-2.05 (m, 2H), 2.05-2.00 (m, 1H), 1.71-1.63 (m, 1H), 1.29 (t, J=7.1 Hz, 3H).

Example 2

Synthesis of (2S,5R)-6-(benzyloxy)-7-oxo-1,6-diazabicyclo[3.2.1]octane-2-carboxylic acid (Intermediate Compound 2a)

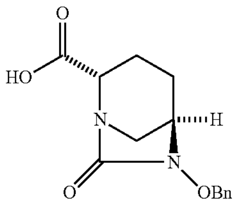

2a

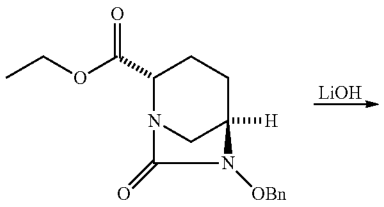

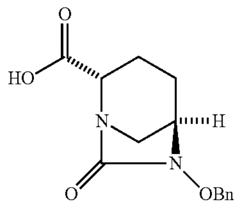

LiOH (1.2 g, 29.6 mmol) was added to a solution of (2S,5R)-ethyl 6-(benzyloxy)-7-oxo-1,6-diazabicyclo[3.2.1]octane-2-carboxylate (9 g, 29.6 mmol) in THF/$H_2O$ (3:1, 240 mL). The mixture was then stiffed at rt overnight. The reaction mixture was washed with EtOAc twice, then the aqueous solution was adjusted pH 2-3 with 1N HCl. The resulting mixture was extracted with DCM three times, and the combined organic layer was dried over saturated $Na_2SO_4$ and concentrated in vacuum to provide (2S,5R)-6-(benzyloxy)-7-oxo-1,6-diazabicyclo[3.2.1]octane-2-carboxylic acid (7.0 g, 77.7%), which was directly used in the next step without further purification. ESI-MS ($EI^+$, m/z): 277.31. $^1H$ NMR (300 MHz, $CDCl_3$) δ 7.49-7.29 (m, 5H), 5.06 (d, J=11.4 Hz, 1H), 4.91 (d, J=11.4 Hz, 1H), 4.15-4.10 (m, 1H), 3.36-3.34

(m, 1H), 3.15-3.11 (m, 1H), 2.83 (d, J=11.8 Hz, 1H), 2.32-2.15 (m, 1H), 2.11-2.01 (m, 2H), 1.74-1.56 (m, 1H).

Example 3

Synthesis of (2S,5R)-6-(benzyloxy)-7-oxo-1,6-diazabicyclo[3.2.1]octane-2-carbaldehyde (intermediate compound 2b)

2b

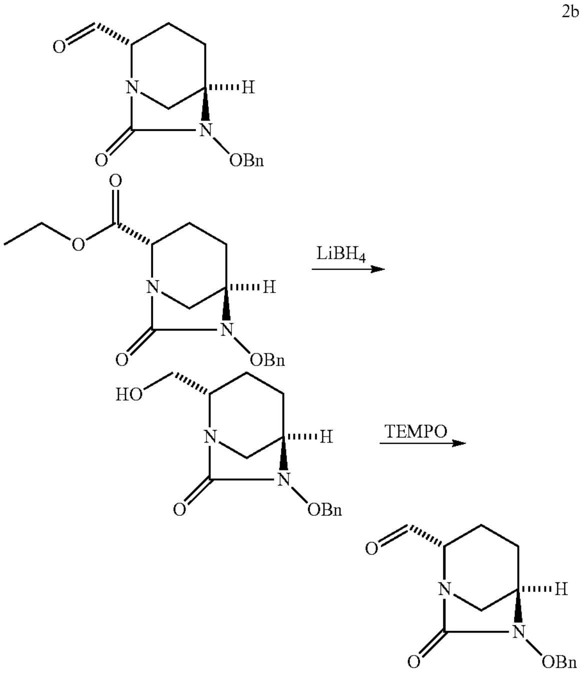

$LiBH_4$ (0.54 g, 24.67 mmol) was added to a solution of (2S,5R)-ethyl 6-(benzyloxy)-7-oxo-1,6-diazabicyclo[3.2.1]octane-2-carboxylate (5 g, 16.44 mmol) in MeOH (50 mL) at −10° C. After 15 minutes another portion of $LiBH_4$ (0.54 g, 24.67 mmol) was added and the mixture was stirred at −10 to 0° C. for 4~5 h. The reaction mixture was carefully quenched by addition of sat. $NaH_2PO_4$ (50 mL) at 0° C. The mixture was diluted with water (20 mL) and extracted with DCM three times. The combined organic layer was concentrated and purified by silica gel column chromatography (gradient elution 0-100% petroleum ether/EtOAc, then 0~2% MeOH/EtOAc) to give (2S,5R)-6-(benzyloxy)-2-(hydroxymethyl)-1,6-diazabicyclo[3.2.1]octan-7-one (3.8 g, 88%) as a white solid. ESI-MS ($EI^+$, m/z): 263.1. $^1$H-NMR (500M, $CDCl_3$): 7.44-7.35 (m, 5H), 5.05 (d, J=11.5 Hz, 1H), 4.90 (d, J=11.5 Hz, 1H), 3.73-3.69 (m, 1H), 3.61-3.58 (m, 2H), 3.33 (m, 1H), 3.01 (br d, J=12.0 Hz, 1H), 2.91 (m, 1H), 2.03-1.95 (m, 2H), 1.58-1.54 (m, 1H), 1.39-1.24 (m, 1H).

TEMPO (48 mg, 0.3 mmol) was added in portions to a solution of (2S,5R)-6-(benzyloxy)-2-(hydroxymethyl)-1,6-diazabicyclo[3.2.1]octan-7-one (7.8 g, 30 mmol) and 1,3,5-trichloro-1,3,5-triazinane-2,4,6-trione (7.0 g, 30 mmol) in DCM (100 mL) at 0° C. The mixture was stirred at 0° C. for 2 h, and filtered through Celite®. The filtrate was dried over $Na_2SO_4$ and concentrated to afford (2S,5R)-6-(benzyloxy)-7-oxo-1,6-diazabicyclo[3.2.1]octane-2-carbaldehyde (7.0 g, 90%) as a yellow oil. ESI-MS ($EI^+$, m/z): 261.1. $^1$H-NMR (500M, $CDCl_3$): 9.74 (s, 1H), 7.45-7.36 (m, 5H), 5.07 (d, J=11.5 Hz, 1H), 4.92 (d, J=11.5 Hz, 1H), 3.89 (d, J=8.0 Hz, 1H), 3.27 (m, 1H), 3.21-3.05 (m, 1H), 2.56 (d, J=12.0 Hz, 1H), 2.20-2.15 (m, 1H), 2.05-2.01 (m, 1H), 1.95-1.93 (m, 1H), 1.49-1.46 (m, 1H).

Example 4

Synthesis of (E)-6-(benzyloxy)-7-oxo-1,6-diazabicyclo[3.2.1]octane-2-carbaldehyde oxime (intermediate compound 2c)

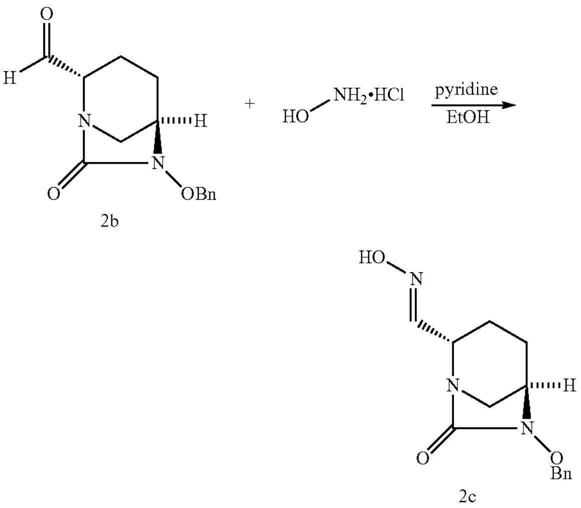

A solution of (2S,5R)-6-(benzyloxy)-7-oxo-1,6-diazabicyclo[3.2.1]octane-2-carbaldehyde (510 mg, 1.96 mmol), hydroxylamine hydrochloride (158 mg, 2.27 mmol) and pyridine (621 mg, 7.85 mmol) in EtOH (15 mL) was stiffed at rt for 2 hrs. Then, the reaction mixture was concentrated and the residue was diluted with DCM (25 mL), washed with water (3×), and saturated sodium chloride, dried over $Na_2SO_4$ and concentrated. The residue was purified by silica gel column chromatography (3:1 to 3:2 petroleum ether/EtOAc) to afford (E)-6-(benzyloxy)-7-oxo-1,6-diazabicyclo[3.2.1]octane-2-carbaldehyde oxime (228 mg, 42%) as a white solid. ESI-MS ($EI^+$, m/z): 276 $[M+H]^+$.

Example 5

Synthesis of (2S,5R)-2-(1,2,4-oxadiazol-3-yl)-7-oxo-1,6-diazabicyclo[3.2.1]octan-6-yl hydrogen sulfate (Compound 804)

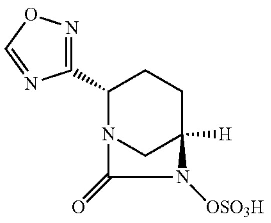

-continued

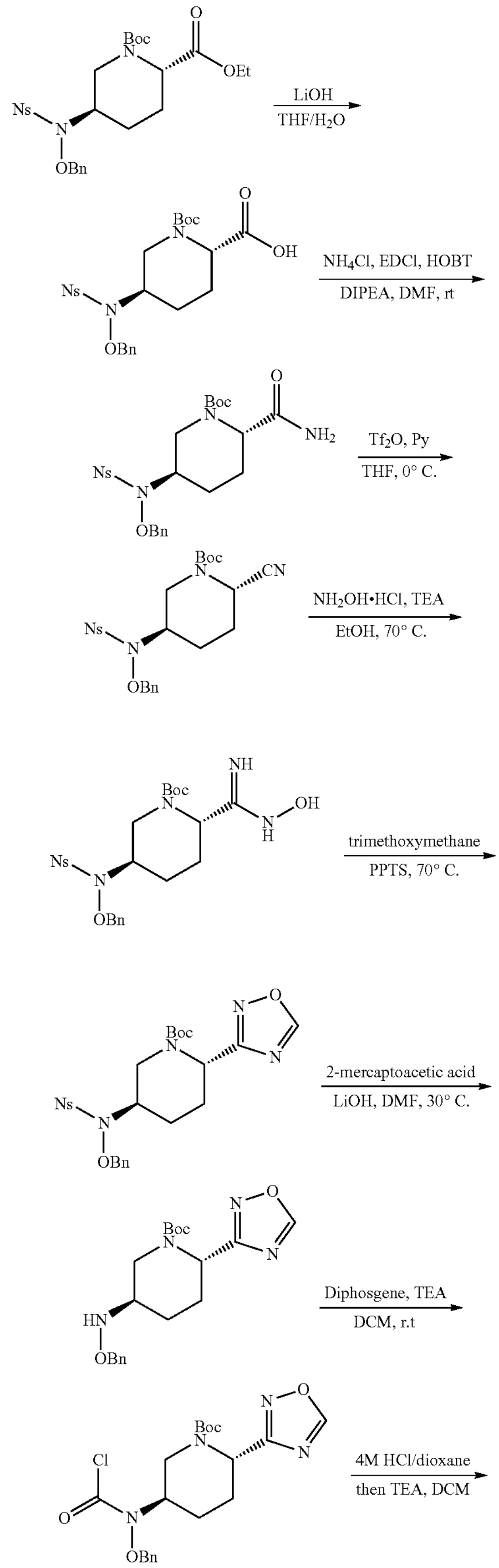

-continued

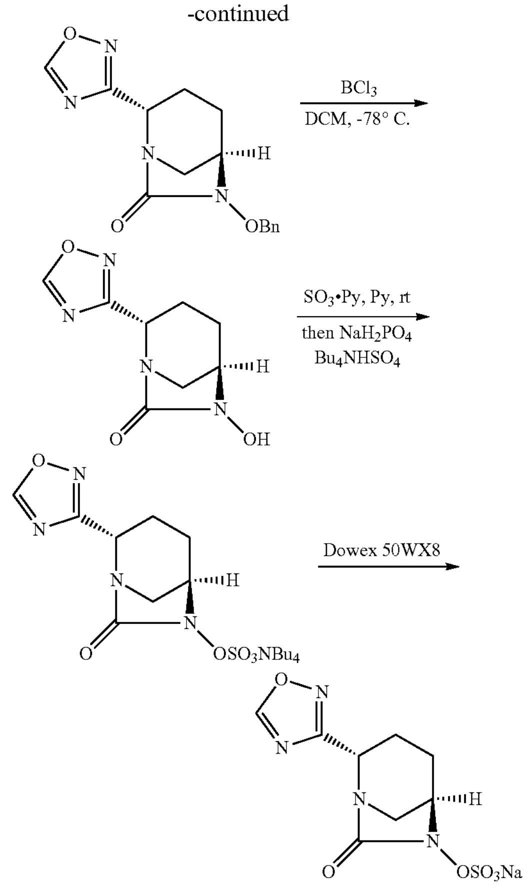

Step 1: A mixture of (2S,5R)-1-tert-butyl 2-ethyl 5-(N-(benzyloxy)-2-nitrophenylsulfonamido) piperidine-1,2-dicarboxylate (5 g, 8.9 mmol), and $LiOH.H_2O$ (1.5 g, 35.5 mmol) in THF (30 mL) and $H_2O$ (100 mL) was stirred at rt for 24 hrs. 1M HCl was then added to adjust the pH to 5~6, following by the addition of EtOAc (300 mL). The mixture was washed with saturated sodium chloride (5×), dried over $Na_2SO_4$, and concentrated. The residue was washed with petroleum ether/EtOAc (95:5, 200 mL) to give (2S,5R)-5-(N-(benzyloxy)-2-nitrophenylsulfonamido)-1-(tert-butoxycarbonyl)piperidine-2-carboxylic acid (4.75 g, 99%) as a pale yellow solid. ESI-MS ($EI^+$, m/z): 436.0 $[M+H-100]^+$.

Step 2: $NH_4Cl$ (1.39 g, 26.18 mmol), HOBt (3.53 g, 26.18 mmol), EDCI (5 g, 26.18 mmol), and DIPEA (8.44 g, 65.45 mmol) were added to a solution of (2S,5R)-5-(N-(benzyloxy)-2-nitrophenylsulfonamido)-1-(tert-butoxycarbonyl) piperidine-2-carboxylic acid (10 g, 18.7 mmol) in DMF (90 mL) The mixture was stirred at rt for 17 hrs, then, EtOAc (500 mL) was added. he mixture was washed with saturated sodium chloride (6×), dried over $Na_2SO_4$, and concentrated. The residue was washed with petroleum ether/EtOAc (95:5, 200 mL) to give (2S,5R)-tert-butyl 5-(N-(benzyloxy)-2-nitrophenylsulfonamido)-2-carbamoylpiperidine-1-carboxylate (9.9 g, 99%) which was used in the next step. ESI-MS ($EI^+$, m/z): 535.0 $[M+H]^+$.

Step 3: Pyridine (2 mL) was added to a solution of (2S,5R)-tert-butyl 5-(N-(benzyloxy)-2-nitrophenylsulfonamido)-2-carbamoylpiperidine-1-carboxylate (1.0 g, 1.87 mmol) in dry THF (40 mL). Then, $Tf_2O$ (1.0 mL) was slowly added over 5 minutes. The mixture was stiffed at 0° C. for 1 h and then EtOAc (30 mL) was added. The mixture was washed with saturated sodium chloride (4×), dried over$Na_2SO_4$, and concentrated. The residue was purified by silica gel column chromatography (gradient elution 0~40% petroleum ether/EtOAc) to give (2S,5R)-tert-butyl 5-(N-(benzyloxy)-2-nitrophenylsulfonamido)-2-cyanopiperidine-1-carboxylate (0.76 g, 79%) as a yellow solid ESI-MS ($EI^+$, m/z): 539.0 $[M+Na]^+$.

Step 4: A solution of (2S,5R)-tert-butyl 5-(N-(benzyloxy)-2-nitrophenylsulfonamido)-2-cyanopiperidine-1-carboxylate (3.1 g, 6.008 mmol), $NH_2OH$.HCl (400 mg, 12 mmol), and TEA (12.136 g, 120.160 mmol) in MeOH (30 mL) and EtOH (30 mL) was stiffed at 70° C. for 17 hrs. EtOAc (300 mL) was then added and the mixture was washed with saturated sodium chloride (3×), dried over$Na_2SO_4$, and concentrated to give (2S,5R)-tert-butyl 5-(N-(benzyloxy)-2-nitrophenylsulfonamido)-2-(N-hydroxycarbamimidoyl) piperidine-1-carboxylate (3.4 g, 99%) as a pale yellow solid, which was used directly in the next step. ESI-MS ($EI^+$, m/z): 550.2 $[M+H]^+$.

Step 5: A mixture of (2S,5R)-tert-butyl 5-(N-(benzyloxy)-2-nitrophenylsulfonamido)-2-(N-hydroxycarbamimidoyl) piperidine-1-carboxylate (3.0 g, 5.46 mmol), trimethoxymethane (60 mL), and PPTS (0.08 g) was stirred at 70° C. for 4 hrs. The solvent was then removed under vacuum. The residue was purified by silica gel column chromatography (gradient elution 0~35% petroleum ether/EtOAc) to give (2S,5R)-tert-butyl 5-(N-(benzyloxy)-2-nitrophenylsulfonamido)-2-(1,2,4-oxadiazol-3-yl)piperidine-1-carboxylate (2.1 g, 69%) as a yellow solid. ESI-MS ($EI^+$, m/z): 582 $[M+Na]^+$.

Step 6: A mixture of (2S,5R)-tert-butyl5-(N-(benzyloxy)-2-nitrophenylsulfonamido)-2-(1,2,4-oxadiazol-3-yl)piperidine-1-carboxylate (1.5 g, 2.683 mmol), $HSCH_2COOH$ (1.48 g, 16.1 mmol), $LiOH.H_2O$ (1.13 g, 26.83 mmol) in DMF (50 mL) was stirred at 30° C. for 17 hrs. EtOAc (150 mL) was then added and the mixture was washed with water (2×), and saturated sodium chloride (2×), dried over $Na_2SO_4$, and concentrated. The residue was purified by silica gel column chromatography (gradient elution 0~50% petroleum ether/EtOAc) to give (2S,5R)-tert-butyl 5-(benzyloxyamino)-2-(1,2,4-oxadiazol-3-yl)piperidine-1-carboxylate (700 mg, 63%) as a pale yellow solid. ESI-MS ($EI^+$, m/z): 375.0 $[M+H]^+$.

Step 7: TEA (405 mg, 4.0 mmol) and diphosgene (514 mg, 2.6 mmol) were added to a solution of (2S,5R)-tert-butyl 5-(benzyloxyamino)-2-(1,2,4-oxadiazol-3-yl)piperidine-1-carboxylate (750 mg, 2.0 mmol) in DCM (70 mL). The mixture was stiffed at 0° C. for 3 hrs. Then, the reaction mixture was washed with saturated sodium chloride (2×), dried over $Na_2SO_4$, and concentrated to give (2S,5R)-tert-butyl 5-(benzyloxy(chlorocarbonyl)amino)-2-(1,2,4-oxadiazol-3-yl)piperidine-1-carboxylate (1.6 g), which was used directly in the next step. ESI-MS ($EI^+$, m/z): 437$[M+H]^+$.

Step 8: A mixture of (2S,5R)-tert-butyl 5-(benzyloxy(chlorocarbonyl)amino)-2-(1,2,4-oxadiazol-3-yl)piperidine-1-carboxylate (1.6 g), and 4 N HCl in dioxane (18 mL), was stirred at rt for 2 hrs. The solvent was then removed under vacuum to give (3R,6S)-6-(1,2,4-oxadiazol-3-yl)piperidin-3-yl(benzyloxy)carbamic chloride (1.4 g) as a white solid, which was used directly in the next step. ESI-MS ($EI^+$, m/z): 301.0.

Step 9: To a solution of (3R,6S)-6-(1,2,4-oxadiazol-3-yl) piperidin-3-yl(benzyloxy)carbamic chloride (1.4 g) in DCM (40 mL) was added TEA until the pH was adjusted topH to 8~9. The mixture was stirred at rt for 2 hrs then, the solvent was removed and the residue was purified by silica gel column chromatography (gradient elution 0~4% petroleum ether/EtOAc) to give the desired product (2S,5R)-6-(benzyloxy)-2-(1,2,4-oxadiazol-3-yl)-1,6-diaza-bicyclo[3.2.1]octan-7-one (400 mg, 67% for 3 steps) as a white solid. ESI-MS ($EI^-$, m/z): 301.2 $[M+H]^+$.

Step 10: $BCl_3$ (1M, 3.34 mL, 3.33 mmol) was added to a solution of (2S,5R)-6-(benzyloxy)-2-(1,2,4-oxadiazol-3-yl)-1,6-diaza-bicyclo[3.2.1]octan-7-one (200 mg, 0.67 mmol) in dry DCM (45 mL) at −78° C. The mixture was stirred at 0° C. for 2 hrs., then it was cooled to −78° C. and quenched with MeOH (8 mL). The solvent was removed by vacuum to give (2S,5R)-6-hydroxy-2-(1,2,4-oxadiazol-3-yl)-1,6-diaza-bicyclo[3.2.1]octan-7-one (180 mg) as a white solid, which was used directly in the next step. ESI-MS ($EI^+$, m/z): 209 $[M-H]^+$.

Step 11: To a solution of (2S,5R)-6-hydroxy-2-(1,2,4-oxadiazol-3-yl)-1,6-diaza-bicyclo[3.2.1]octan-7-one (180 mg crude from above) in dry pyridine (4 mL) was added $SO_3$.Py (608 mg). The mixture was stirred at rt for 3 hrs and then concentrated under vacuum. The residue was re-dissolved in aqueous $NaH_2PO_4$ (1.5 M, 50 mL) and then tetrabutylammonium hydrogensulphate (970 mg) was added. The mixture was stirred at rt for 30 minutes and then extracted with EtOAc (3×). The combined organic layer was dried and concentrated and the residue was purified by silica gel column chromatography (gradient elution 0 to 25% EtOAc:Acetone) to afford tetrabutylammonium (2S,5R)-2-(1,2,4-oxadiazol-3-yl)-7-oxo-1,6-diaza-bicyclo[3.2.1]octan-6-yl sulfate (280 mg, 45% for 2 steps) as a white solid. ESI-MS ($EI^-$, m/z): 289.0 $[M-H]^-$.

Step 12, Resin Exchange: Tetrabutylammonium (2S,5R)-2-(1,2,4-oxadiazol-3-yl)-7-oxo-1,6-diaza-bicyclo[3.2.1]octan-6-yl sulfate (280 mg) was dissolved in a minimum amount of HPLC grade water (~3 mL) and passed through a column of 8 g of DOWEX 50WX 8 $Na^+$ resin (the resin was pre-washed with >200 mL of HPLC grade water) and eluted with HPLC grade water to provide sodium (2S,5R)-2-(1,2,4-oxadiazol-3-yl)-7-oxo-1,6-diaza-bicyclo[3.2.1]octan-6-yl sulfate (180 mg, 90%) as a white solid after lyophilization. ESI-MS ($EI^-$, m/z): 289.1 $[M-H]^-$. $^1$H-NMR (500 MHz, $D_2O$): δ 9.23 (s, 1H), 4.75 (d, J=7.5 Hz, 1H), 4.20 (br s, 1H), 3.18 (m, 1H), 2.99 (d, J=12 Hz, 1H), 2.32-2.27 (m, 1H), 2.21-2.14 (m, 2H), 1.97-1.92 (m, 1H).

Example 6

Synthesis of (2S,5R)-2-(5-amino-1,2,4-oxadiazol-3-yl)-7-oxo-1,6-diazabicyclo[3.2.1]octan-6-yl hydrogen sulfate (Compound 805)

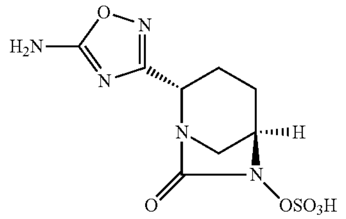

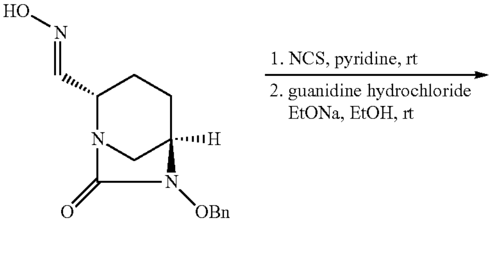

-continued

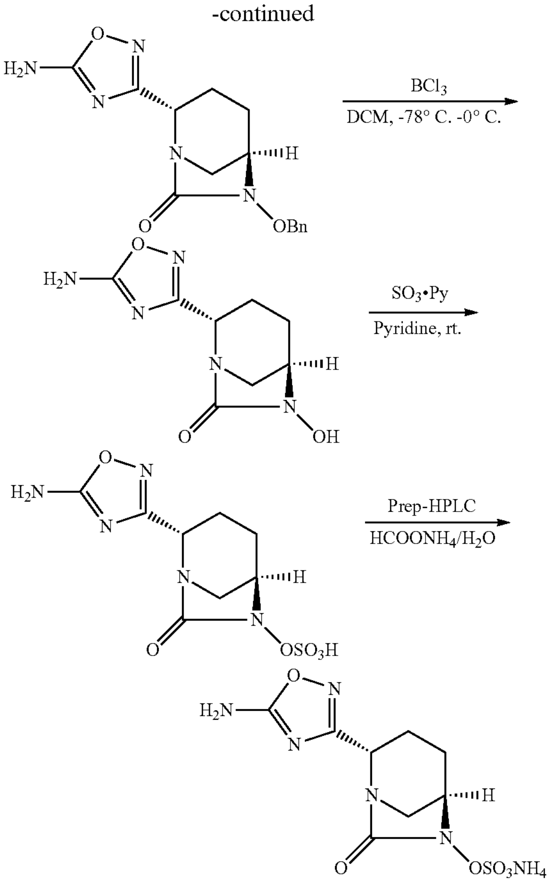

Step 1:

a) NCS (0.76 g, 5.72 mmol) was added to a solution of (E)-6-(benzyloxy)-7-oxo-1,6-diaza-bicyclo[3.2.1]octane-2-carbaldehyde oxime (1.5 g, 5.45 mmol) in DCM (10 mL) then one drop of pyridine was added. The mixture was stirred at rt for 18 hrs, then the mixture was concentrated under reduced pressure and dried under high vacuum. The crude product was dissolved in absolute EtOH (10 mL).

b) In a separate flask, guanidine hydrochloride (1.04 g, 10.9 mmol) was mixed with EtONa (16% in EtOH, 4.63 g, 10.9 mmol) at rt, and the solid was filtered off.

The solution of a) was added to the filtrate of b) at rt. The mixture was stirred at rt overnight, then, the reaction mixture was concentrated, diluted with water (20 mL), and extracted with EtOAc (3×). The combined organic layer was dried over $Na_2SO_4$ and concentrated. The residue was purified by prep-HPLC using ammonium formate buffer to afford (2S,5R)-2-(5-amino-1,2,4-oxadiazol-3-yl)-6-(benzyloxy)-1,6-diaza-bicyclo[3.2.1]octan-7-one (120 mg, 7%) as a white solid. ESI-MS ($EI^+$, m/z): 316 $[M+H]^+$.

Step 2. $BCl_3$ (1M, 5.08 ml, 5.08 mmol) was added to a solution of (2S,5R)-2-(5-amino-1,2,4-oxadiazol-3-yl)-6-(benzyloxy)-1,6-diaza-bicyclo[3.2.1]octan-7-one (160 mg, 0.508 mmol) in dry DCM (8 mL) at −78° C. The mixture was stirred under $N_2$ atmosphere at 0° C. for 2 hrs then, it was cooled to −78° C. and quenched with MeOH (1.0 mL). The solvent was removed by vacuum to afford (2S,5R)-2-(5-amino-1,2,4-oxadiazol-3-yl)-6-hydroxy-1,6-diaza-bicyclo[3.2.1]octan-7-one (110 mg) as a white solid, which was used directly in the next step. ESI-MS ($EI^+$, m/z): 226 $[M+H]^+$.

Step 3: To a mixture of (2S,5R)-2-(5-amino-1,2,4-oxadiazol-3-yl)-6-hydroxy-1,6-diaza-bicyclo[3.2.1]octan-7-one (110 mg, 0.49 mmol) and $SO_3$.Py (389 mg, 2.44 mmol) was added dry pyridine (2 mL) under $N_2$. The mixture was stiffed at rt for 2.5 hrs and then concentrated under vacuum to afford (2S,5R)-2-(5-amino-1,2,4-oxadiazol-3-yl)-7-oxo-1,6-diaza-bicyclo[3.2.1]octan-6-yl hydrogen sulfate, which was used for next step directly. ESI-MS ($EI^-$, 304, m/z): $[M-H]^-$.

Step 4: Crude (2S,5R)-2-(5-amino-1,2,4-oxadiazol-3-yl)-7-oxo-1,6-diaza-bicyclo[3.2.1]octan-6-yl hydrogen sulfate was purified by Prep-HPLC using ammonium formate buffer to afford (2S,5R)-2-(5-amino-1,2,4-oxadiazol-3-yl)-7-oxo-1,6-diaza-bicyclo[3.2.1]octan-6-yl aminooxy sulfonate (25 mg, 20% of two steps). ESI-MS ($EI^-$, m/z): 304 $[M-H]^-$. $^1$H-NMR (500 MHz, $D_2O$): δ 4.42 (d, J=8.0 Hz, 1H), 4.12 (s, 1H), 3.12-3.09 (m, 1H), 3.00 (d, J=15 Hz, 1H), 2.11-1.96 (m, 3H), 1.86-1.79 (m, 1H).

Example 7

Synthesis of (2S,5R)-7-oxo-2-(5-(piperidin-4-yl)-1,2,4-oxadiazol-3-yl)-1,6-diazabicyclo[3.2.1]octan-6-yl hydrogen sulfate (Compound 806)

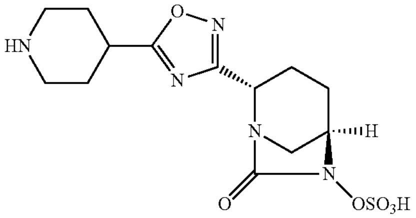

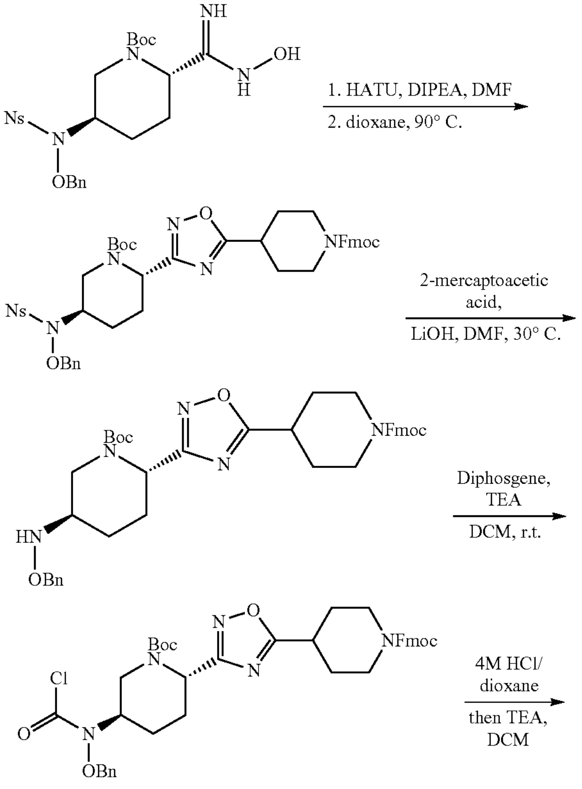

-continued

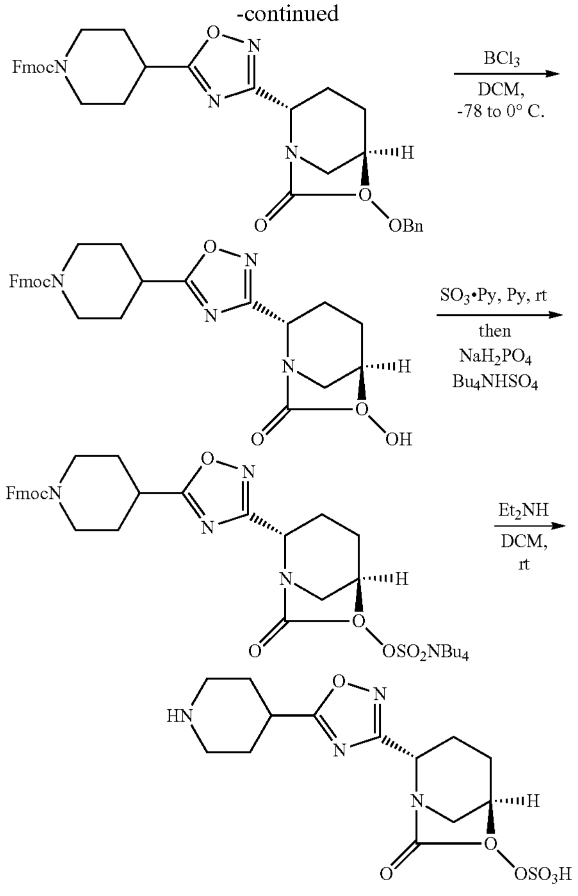

Step 1: A solution of (2S,5R)-tert-butyl 5-(N-(benzyloxy)-2-nitrophenylsulfonamido)-2-(N-hydroxycarbamimidoyl) piperidine-1-carboxylate (3.12 g, 5.7 mmol), 1-(((9H-fluoren-9-yl)methoxy)carbonyl)piperidine-4-carboxylic acid (2 g, 5.7 mmol), HATU (3.23 g, 8.55 mmol) and DIPEA (1.50 g, 11.44 mmol) in DMF (50 mL) was stirred at rt for 1 h. EtOAc (150 mL) was then added and the mixture was washed with saturated sodium chloride (3×), dried over $Na_2SO_4$, and concentrated. The residue was dissolved in dioxane (50 mL) and heated at 90° C. for 17 hrs. The mixture was then concentrated under vacuum and the residue was purified by silica gel column chromatography (gradient elution 0~45% petroleum ether/EtOAc) to give (2S,5R)-tert-butyl 2-(5-(1-(((9H-fluoren-9-yl)methoxy)carbonyl)piperidin-4-yl)-1,2,4-oxadiazol-3-yl)-5-(N-(benzyloxy)-2-nitrophenylsulfonamido)piperidine-1-carboxylate (1.2 g, 24%) as a yellow solid. ESI-MS ($EI^+$, m/z): 765 $[M+H-100]^+$.

Step 2: A mixture of (2S,5R)-tert-butyl 2-(5-(((9H-fluoren-9-yl)methoxy)carbonyl)piperidin-4-yl)-1,2,4-oxadiazol-3-yl)-5-(N-(benzyloxy)-2-nitrophenylsulfonamido)piperidine-1-carboxylate (200 mg, 0.231 mmol), $HSCH_2COOH$ (128 mg, 1.386 mmol) and $LiOH.H_2O$ (97 g, 2.310 mmol) in DMF (5.0 mL) was stirred at 30° C. for 17 hrs. EtOAc (50 mL) was then added and the organic layer was washed with water (2×), and saturated sodium chloride (2×), dried over $Na_2SO_4$, and concentrated. The residue was purified by silica gel column chromatography (gradient elution 0~50% petroleum ether/EtOAc) to give (2S,5R)-tert-butyl 2-(5-(1-(((9H-fluoren-9-yl)methoxy)carbonyl)piperidin-4-yl)-1,2,4-oxadiazol-3-yl)-5-(benzyloxyamino) piperidine-1-carboxylate (40 mg, 25%) as a yellow oil. ESI-MS ($EI^+$, m/z): 680 $[M+H]^+$ Step 3: Diphosgene (144 mg, 0.727 mmol) was added to a solution of (2S,5R)-tert-butyl 2-(5-(1-(((9H-fluoren-9-yl) methoxy) carbonyl)piperidin-4-yl)-1,2,4-oxadiazol-3-yl)-5-(benzyloxyamino)piperidine-1-carboxylate (380 mg, 0.559 mmol) and TEA (113 mg, 1.118 mmol) in DCM (5.0 mL). The mixture was stirred at 0° C. for 1 h, then, DCM (20 mL) was added and the mixture was washed with saturated sodium chloride (2×), dried over $Na_2SO_4$, and concentrated to give (2S,5R)-tert-butyl 2-(5-(1-(((9H-fluoren-9-yl)methoxy)carbonyl)piperidin-4-yl)-1,2,4-oxadiazol-3-yl)-5-(benzyloxy(chlorocarbonyl)amino)piperidine-1-carboxylate (400 mg), which was directly used in the next step. ESI-MS ($EI^+$, m/z): 742 $[M+H]^+$.

Step 4: A mixture of (2S,5R)-tert-butyl 2-(5-(1-(((9H-fluoren-9-yl)methoxy)carbonyl)piperidin-4-yl)-1,2,4-oxadiazol-3-yl)-5-(benzyloxy(chlorocarbonyl)amino)piperidine-1-carboxylate (~400 mg) and 4 N HCl/dioxane (5.0 mL) was stirred at rt for 2 hrs. The solvent was then removed under vacuum to give (9H-fluoren-9-yl)methyl 4-(3-((2S,5R)-5-(benzyloxy(chlorocarbonyl)amino)piperidin-2-yl)-1,2,4-oxadiazol-5-yl)piperidine-1-carboxylate (400 mg) as a white solid. ESI-MS ($EI^+$, m/z): 642 $[M+H]^+$.

To a solution of crude (9H-fluoren-9-yl)methyl 4-(3-((2S,5R)-5-(benzyloxy(chlorocarbonyl)amino)piperidin-2-yl)-1,2,4-oxadiazol-5-yl)piperidine-1-carboxylate (400 mg) in DCM (25 mL) was added TEA until the pH was adjusted topH 8~9. The mixture was stirred at rt for 2 hrsthen, the solvent was removed. The residue was purified by silica gel column (gradient elution 0~45% petroleum ether/EtOAc) to give (9H-fluoren-9-yl)methyl 4-(3-((2S,5R)-6-(benzyloxy)-7-oxo-1,6-diaza-bicyclo[3.2.1]octan-2-yl)-1,2,4-oxadiazol-5-yl)piperidine-1-carboxylate (100 mg, 30% for 3 steps) as a white solid. ESI-MS ($EI^-$, m/z): 606 $[M+H]^+$.

Step 5: $BCl_3$ (850 μL, 0.85 mmol, 1 M in DCM) was added to a solution of (9H-fluoren-9-yl) methyl 4-(3-((2S,5R)-6-(benzyloxy)-7-oxo-1,6-diaza-bicyclo[3.2.1]octan-2-yl)-1,2,4-oxadiazol-5-yl)piperidine-1-carboxylate (100 mg, 0.17 mmol) in dry DCM (10 mL) at −78° C. The mixture was stirred under $N_2$ atmosphere at 0° C. for 6 hrs, cooled to −78° C., then MeOH (1 mL) was slowly added. The solvents were evaporated under vacuum at 0° C. to give (9H-fluoren-9-yl) methyl 4-(3-((2S,5R)-6-hydroxy-7-oxo-1,6-diaza-bicyclo[3.2.1]octan-2-yl)-1,2,4-oxadiazol-5-yl)piperidine-1-carboxylate (97 mg) as a yellow solid, which was used directly in the next step. ESI-MS ($EI^+$, m/z): 516.3 $[M+H]^-$.

Step 6: To a solution of crude (9H-fluoren-9-yl)methyl 4-(3-((2S,5R)-6-hydroxy-7-oxo-1,6-diaza-bicyclo[3.2.1]octan-2-yl)-1,2,4-oxadiazol-5-yl)piperidine-1-carboxylate (97 mg) in dry pyridine (2 mL) was added $SO_3$.Py (140 mg, 0.85 mmol). The mixture was stirred at rt for 6 hrs and then concentrated under vacuum. The residue was re-dissolved in aqueous $NaH_2PO_4$ (1.5 M, 10 mL) thentetrabutylammonium hydrogensulphate (75 mg) was added. The mixture was stirred at rt for 20 minutes, then extracted with EtOAc (3×). The combined organic layer was dried and concentrated. The residue was purified by silica gel column chromatography (gradient elution 10:1 to 2:1 DCM/acetone) to give tetrabutylammonium (9H-fluoren-9-yl)methyl 4-(3-((2S,5R)-7-oxo-6-(sulfooxy)-1,6-diaza-bicyclo[3.2.1]octan-2-yl)-1,2,4-oxadiazol-5-yl)piperidine-1-carboxylate sulfate as a white solid (84 mg, 61% for two steps). ESI-MS ($EI^-$, m/z): 594.1 $[M-H]^-$.

Step 7: $Et_2NH$ (0.5 mL, 5.0 mmol)) was added to a solution of tetrabutylammonium (9H-fluoren-9-yl)methyl 4-(3-((2S,5R)-7-oxo-6-(sulfooxy)-1,6-diaza-bicyclo[3.2.1]octan-2-yl)-1,2,4-oxadiazol-5-yl)piperidine-1-carboxylate sulfate (84 mg, 0.1 mmol) in dry DCM (10 mL. The mixture was stirred at rt for 12 hrs and the solvents were evaporated under vacuum. The residue was purified by prep-HPLC to afford (2S,5R)-7-oxo-2-(5-(piperidin-4-yl)-1,2,4-oxadiazol-3-yl)-1,6-diaza-bicyclo[3.2.1]octan-6-yl hydrogen sulfate (9.0 mg). ESI-MS ($EI^+$, m/z): 374.15 $[M+H]^+$. $^1H$ NMR (300 MHz, $D_2O$) δ 4.61 (d, J=6.0 Hz, 1H), 4.12 (br s, 1H), 3.50-3.33 (m, 3H), 3.15-3.05 (m, 3H), 2.91 (d, J=12.2 Hz, 1H), 2.35-1.72 (m, 8H).

Example 8

Synthesis of (2S,5R)-2-(1,2,4-oxadiazol-5-yl)-7-oxo-1,6-diazabicyclo[3.2.1]octan-6-yl hydrogen sulfate (Compound 801)

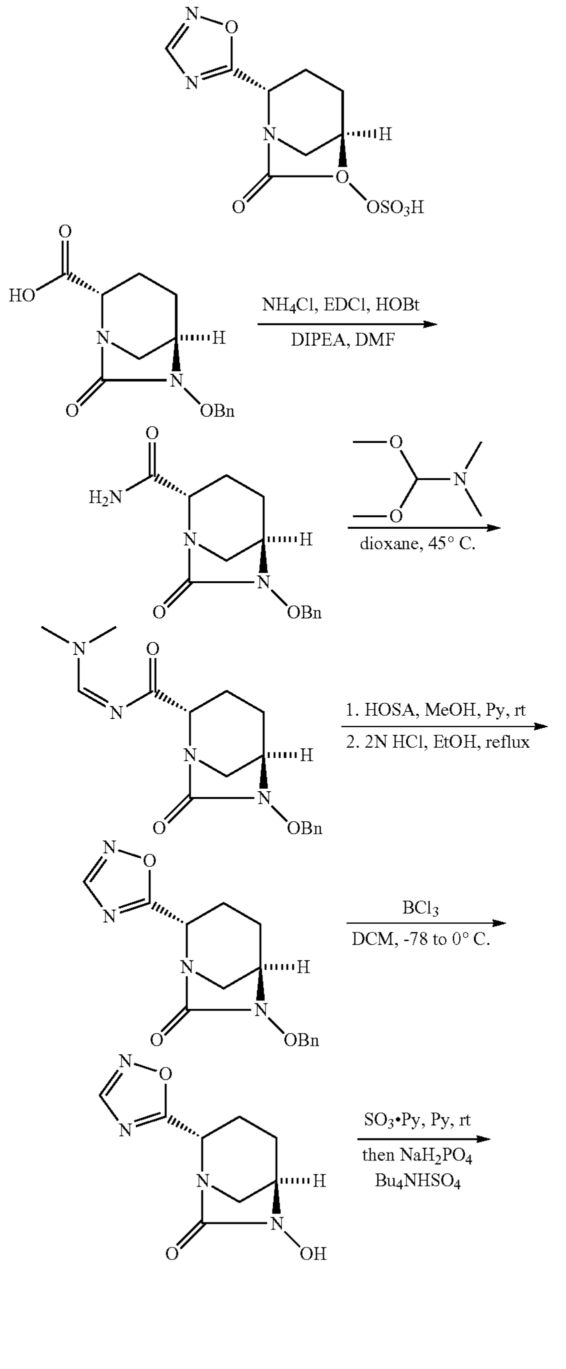

-continued

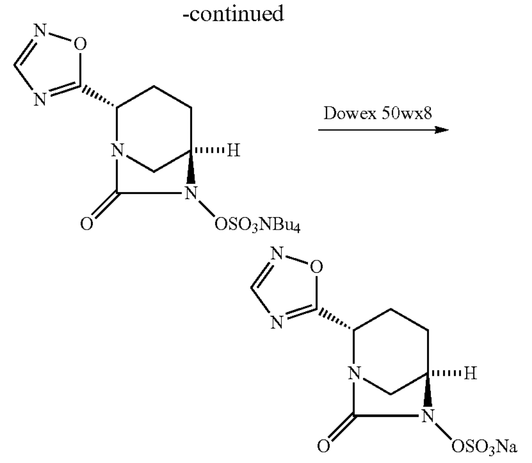

Step 1: DIPEA (5.8 mL, 36.2 mmol) was added to a solution of (2S,5R)-6-(benzyloxy)-7-oxo-1,6-diaza-bicyclo[3.2.1]octane-2-carboxylic acid (5.0 g, 18.1 mmol), EDCI (5.2 g, 27.2 mmol), HOBT (3.7 g, 27.2 mmol) and $NH_4Cl$ (1.94 g, 36.2 mmol) in DMF (60 mL) at rt. The reaction mixture was stiffed for 17 hrs, then diluted with ice water (100 mL) and extracted with EtOAc (3×). The combined organic layer was dried over $Na_2SO_4$, and concentrated. The residue was purified by silica gel column chromatography (2:1 EtOAc/petroleum ether) to afford (2S,5R)-6-(benzyloxy)-7-oxo-1,6-diaza-bicyclo[3.2.1]octane-2-carboxamide (4.0 g, 80%) as a white solid. ESI-MS ($EI^+$, m/z): 276 $[M+H]^+$.

Step 2. Dimethoxy-N,N-dimethylmethanamine (0.97 mL, 7 mmol) was added to a solution of (2S,5R)-6-(benzyloxy)-7-oxo-1,6-diaza-bicyclo[3.2.1]octane-2-carboxamide (1.38 g, 5 mmol) in 1,4-dioxane (20 mL) at rt. The mixture was stiffed at 45-50° C. for 2 hrs under vacuum to remove the methanol formed during the reaction. Then, the reaction mixture was concentrated under vacuum, and the residue was washed with $Et_2O$ (2×) and dried to give (2S,5R,Z)-6-(benzyloxy)-N-((dimethylamino)methylene)-7-oxo-1,6-diaza-bicyclo[3.2.1]octane-2-carboxamide (1.33 g, 80%) as a white solid. (ESI-MS ($EI^+$, 331, m/z): $[M+H]^+$.

Step 3: (2S,5R,Z)-6-(benzyloxy)-N-((dimethylamino)methylene)-7-oxo-1,6-diaza-bicyclo[3.2.1]octane-2-carboxamide (1.33 g, 4.03 mmol) in EtOH (22 mL) was treated with pyridine (0.64 ml, 8.06 mmol), followed by the addition of a solution of HOSA (547 mg, 4.84 mmol) in MeOH (4.5 mL). The resulting mixture was stirred at rt for 30 minutes and then concentrated under vacuum. The residue was dissolved in DCM/THF (1:2, 30 mL) and washed with water (10 mL). The organic layer was dried over$Na_2SO_4$, and concentrated. The residue was re-dissolved in EtOH (22 mL) and 2N HCl (8.0 mL). The mixture was heated at reflux for 20 minutes, concentrated and extracted with DCM (2×). The crude material was purified by prep-HPLC to give (2S,5R)-6-(benzyloxy)-2-(1,2,4-oxadiazol-5-yl)-1,6-diaza-bicyclo[3.2.1]octan-7-one (50 mg, 4.1%) as a light yellow oil. ESI-MS ($EI^+$, 301, m/z): $[M+H]^+$. $^1H$-NMR (500 MHz, $CDCl_3$): δ 8.44 (s, 1H), 7.45-7.35 (m, 5H), 5.09 (d, J=11.5 Hz, 1H), 4.94 (d, J=11.5 Hz, 1H), 4.85 (d, J=8.0 Hz, 1H), 3.36 (m, 1H), 3.01 (d, J=12.0 Hz, 1H), 2.81 (d, J=12.0 Hz, 1H), 2.37-2.35 (m, 1H), 2.25-2.21 (m, 1H), 2.01-2.00 (m, 1H), 1.85-1.84 (m, 1H).

Step 4: $BCl_3$ (1M in DCM, 1.2 mL, 1.2 mmol) was added to (2S,5R)-6-(benzyloxy)-2-(1,2,4-oxadiazol-5-yl)-1,6-diaza-bicyclo[3.2.1]octan-7-one (50 mg, 0.167 mmol) in DCM (10 mL) at −78° C. The mixture was warmed to 0° C. and stirred for 2 hrs. The reaction was then quenched by the addition of MeOH (1 mL) and the resulting solution was concentrated under vacuum to give (2S,5R)-6-hydroxy-2-(1,2,4-oxadiazol-5-yl)-1,6-diaza-bicyclo[3.2.1]octan-7-one (34 mg, 98%) as a white solid, which was used directly in the next step. ESI-MS ($EI^+$, 211, m/z): $[M+H]^+$.

Step 5: A mixture of (2S,5R)-6-hydroxy-2-(1,2,4-oxadiazol-5-yl)-1,6-diaza-bicyclo[3.2.1]octan-7-one (48 mg, 0.228 mmol) and $SO_3$.Py (182 mg, 1.14 mmol) in dry pyridine (2 mL) was stirred at rt for 2.5 hrs. The reaction mixture was then concentrated in vacuum and the residue was re-dissolved in aqueous $NaH_2PO_4$ (1.5 M, 10 mL). Tetrabutylammonium hydrogensulphate (105 mg) was added, the mixture was stirred at rt for 15 minutes, and then extracted with EtOAc (4×). The combined organic layer was dried and concentrated. The residue was purified by silica gel column chromatography (gradient elution 10:1 to 1:1 DCM/acetone) to give tetrabutylammonium (2S,5R)-2-(1,2,4-oxadiazol-5-yl)-7-oxo-1,6-diazabicyclo[3.2.1]octan-6-yl sulfate (50 mg, 41%) as a white solid. ESI-MS ($EI^-$, 289, m/z): $[M-H]^-$.

Step 6: Tetrabutylammonium (2S,5R)-2-(1,2,4-oxadiazol-5-yl)-7-oxo-1,6-diazabicyclo[3.2.1]octan-6-yl sulfate (50 mg) was dissolved in a minimum amount of HPLC grade water (~1 mL) and passed through a column of 2 g of DOWEX 50WX 8 $Na^+$ resin (the resin was pre-washed with >0.5 L of HPLC grade water) and eluted with HPLC grade water to afford sodium (2S,5R)-2-(1,2,4-oxadiazol-5-yl)-7-oxo-1,6-diazabicyclo[3.2.1]octan-6-yl sulfate (21 mg, 72%) as a white solid after lyophilization. ESI-MS ($EI^-$, m/z): 289 $[M-H]^-$. $^1$H-NMR (500 MHz, $CDCl_3$): δ 8.76 (s, 1H), 4.92 (d, J=7.5 Hz, 1H), 4.24 (s, 1H), 3.29 (d, J=12.5 Hz, 1H), 2.98 (d, J=12.5 Hz, 1H), 2.42-2.38 (m, 1H), 2.29-2.20 (m, 2H), 2.0-1.97 (m, 1H).

Example 9

Synthesis of (2S,5R)-2-(3-amino-1,2,4-oxadiazol-5-yl)-7-oxo-1,6-diaza-bicyclo[3.2.1]octan-6-yl tetrabutylaminooxy sulfonate (Compound 802)

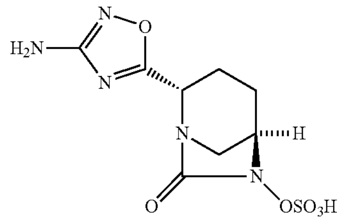

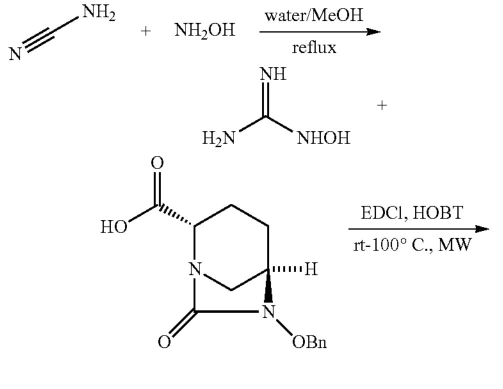

-continued

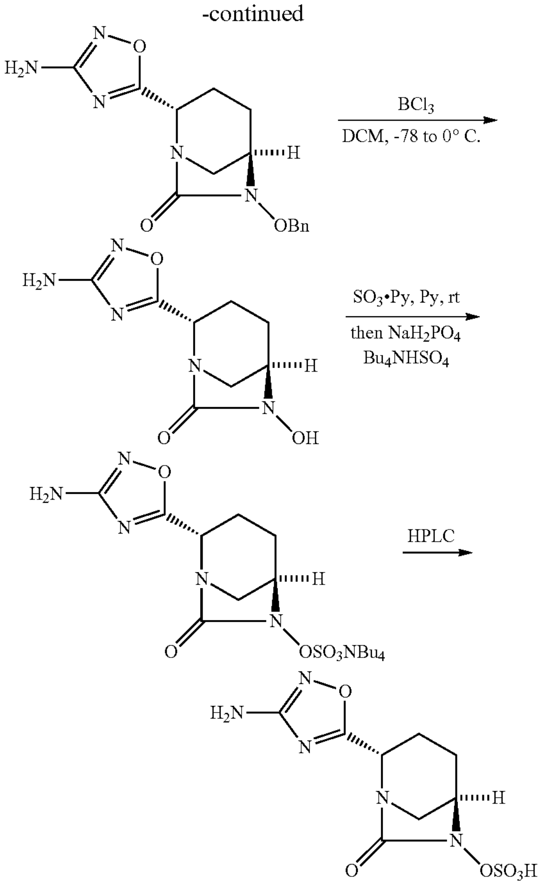

Step 1: Hydroxylamine (50% in water, 3.6 mL, 0.059 mol) was added to cyanamide (50% in water, 3.24 g, 0.077 mol) in methanol (100 mL). The mixture was heated to reflux for 4.5 hrs and concentrated to remove methanol/water, followed by co-evaporation with methanol (2×) to remove residual water to obtain 1-hydroxyguanidine (3.0 g, 68%) as a light yellow solid.

Step 2: A solution of (2S,5R)-6-(benzyloxy)-2-(5-(piperidin-4-yl)-1,3,4-oxadiazol-2-yl)-1,6-diazabicyclo[3.2.1]octan-7-one (2.0 g, 7.25 mmol), EDCI (1.53 g, 7.98 mmol) and HOBT (1.08 g, 7.98 mmol) in DMF (15 mL) was stirred at rt for 0.5 h. 1-Hydroxyguanidine (0.653 g, 7.98 mmol) was then added and the reaction mixture was stirred for an additional 0.5 h. The resulting solution was treated under microwave at 100° C. for 1.5 hrs. The mixture was poured into water and extracted with EtOAc (2×). The combined organic layers were then washed with water (20 mL), and saturated sodium chloride (20 mL), dried over $Na_2SO_4$, and concentrated. The residue was purified by silica gel column chromatography (2:1 EtOAc/petroleum ether) to give (2S,5R)-2-(3-amino-1,2,4-oxadiazol-5-yl)-6-(benzyloxy)-1,6-diaza-bicyclo[3.2.1]octan-7-one (1.0 g, 44%). (ESI-MS ($EI^+$, m/z): 316 $[M+H]^+$.

Step 3: $BCl_3$ (1M, 15.87 mL, 15.87 mmol) was added to a solution of (2S,5R)-2-(3-amino-1,2,4-oxadiazol-5-yl)-6-(benzyloxy)-1,6-diaza-bicyclo[3.2.1]octan-7-one (1.0 g, 3.17 mmol) in dried DCM (20 mL) at −78° C. The mixture was stirred under $N_2$ atmosphere at 0° C. for 2 hrs, cooled to −78° C. and quenched with MeOH (2 mL). The solvent was removed under vacuum to give ((2S,5R)-2-(3-amino-1,2,4-oxadiazol-5-yl)-6-hydroxy-1,6-diaza-bicyclo[3.2.1]octan-7-one (700 mg), which was used in the next step directly. ESI-MS ($EI^+$, m/z): 226 $[M+H]^+$.

Step 4: A mixture of ((2S,5R)-2-(3-amino-1,2,4-oxadiazol-5-yl)-6-hydroxy-1,6-diaza-bicyclo[3.2.1]octan-7-one (700 mg, 3.11 mmol) and $SO_3$.Py (1.48 g, 9.33 mmol) in dry pyridine (5 mL) was stirred at rt for 2.5 hrs. The reaction mixture was then concentrated under vacuum. then re-dissolved in aqueous $NaH_2PO_4$ (1.5 M, 30 mL). Tetrabutylammonium hydrogensulphate (1.16 g) was added, the mixture stirred at rt for 15 minutes, and then extracted with EtOAc (4×). The combined organic layer was dried and concentrated and the residue was purified by silica gel column chromatography (gradient elution 10:1 to 5:1 DCM/acetone) to afford tetrabutylammonium (2S,5R)-2-(3-amino-1,2,4-oxadiazol-5-yl)-7-oxo-1,6-diazabicyclo[3.2.1]octan-6-yl sulfate (1.7 g) as a white solid. (ESI-MS ($EI^-$, 304, m/z): $[M-H]^-$. $^1$H-NMR (500 MHz, DMSO-$d_6$): δ 6.4 (s, 2H), 4.48 (d, J=8.0 Hz, 1H), 3.67 (s, 1H), 3.24-3.14 (m, 8H), 3.00 (d, J=12 Hz, 1H), 2.24 (d, J=11.5 Hz, 1H), 2.2-2.06 (m, 3H), 1.87-1.82 (m, 1H), 1.59-1.53 (m, 8H), 1.35-1.27 (m, 8H), 0.93-0.82 (m, 12H).

Step 5: Tetrabutylammonium (2S,5R)-2-(3-amino-1,2,4-oxadiazol-5-yl)-7-oxo-1,6-diazabicyclo[3.2.1]octan-6-yl sulfate was further purified by prep-HPLC using ammonium formate buffer to afford (2S,5R)-2-(3-amino-1,2,4-oxadiazol-5-yl)-7-oxo-1,6-diazabicyclo[3.2.1]octan-6-yl hydrogen sulfate. ESI-MS ($EI^+$, m/z): 306.1. $^1$H NMR (300 MHz, $D_2O$) δ 4.19 (br s, 1H), 3.27-3.23 (m, 1H), 3.04-2.97 (m, 1H), 2.39-1.66 (m, 4H).

Example 10

Synthesis of (2S,5R)-7-oxo-2-(3-(piperidin-4-yl)-1,2,4-oxadiazol-5-yl)-1,6-diazabicyclo[3.2.1]octan-6-yl hydrogen sulfate (Compound 803)

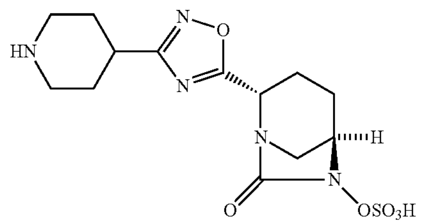

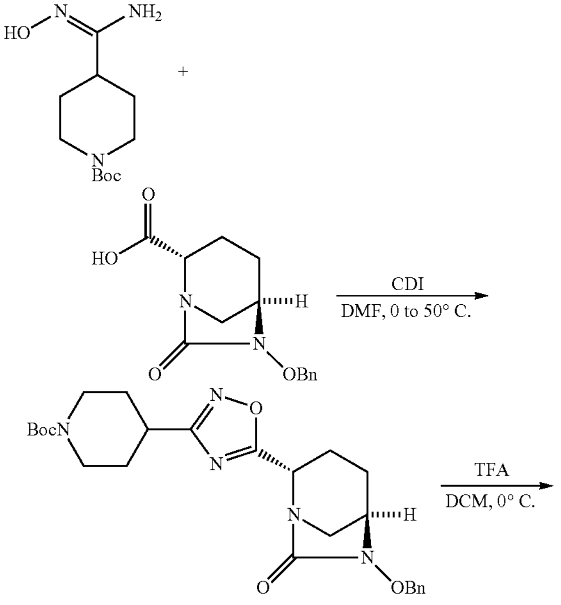

-continued

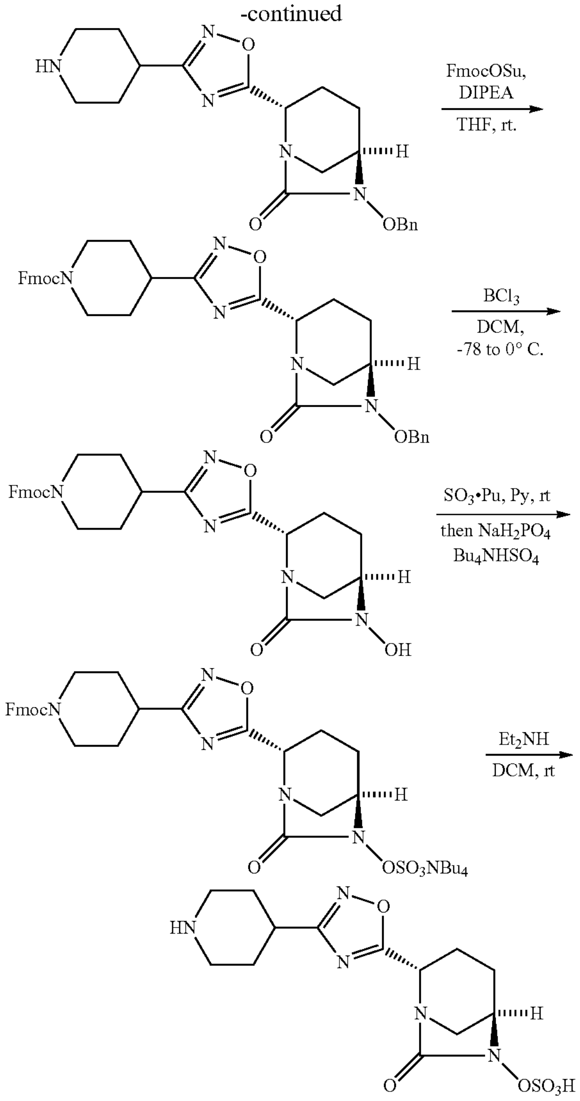

Step 1: CDI (511.3 mg, 3.1 mmol) was added to a solution of crude (2S,5R)-6-(benzyloxy)-2-(5-(piperidin-4-yl)-1,3,4-oxadiazol-2-yl)-1,6-diazabicyclo[3.2.1]octan-7-one (726 mg, 2.6 mmol) in DMF (15 mL). The mixture was stirred at rt for 1 h, then, (E)-tert-butyl 4-(N'-hydroxycarbamimidoyl) piperidine-1-carboxylate (631.8 mg, 2.6 mmol) was added at rt. The mixture was stirred at rt for 2 hrs, and then stirred at 50° C. for another 6 hrs. The mixture was diluted with EtOAc (150 mL) and washed with 1 M HCl (2×), water (2×), and saturated sodium chloride (2×), dried over $Na_2SO_4$, and concentrated. The residue was purified by silica gel column chromatography (1:5 to 1:1 EtOAc/hexanes) to give tert-butyl 4-(5-((2S,5R)-6-(benzyloxy)-7-oxo-1,6-diaza-bicyclo[3.2.1]octan-2-yl)-1,2,4-oxadiazol-3-yl)piperidine-1-carboxylate (968 mg, 76%) as a white solid. ESI-MS ($EI^+$, m/z): 506.2 $[M+Na]^+$. $^1$H-NMR (400 MHz, $CDCl_3$): δ 7.47-7.36 (m, 5H), 4.99-4.94 (m, 2H), 4.73 (d, J=6.0 Hz, 1H), 3.93 (d, J=9.6 Hz, 1H), 3.72 (s, 1H), 3.08-2.90 (m, 4H), 2.72 (d, J=9.6 Hz, 1H), 2.15 (dd, J=12.0, 5.2 Hz, 1H), 2.09-1.93 (m, 5H), 1.85-1.79 (m, 1H), 1.59-1.50 (m, 2H), 1.40 (s, 9H).

Step 2: $CF_3COOH$ (4 mL) was added to the solution of tert-butyl 4-(5-((2S,5R)-6-(benzyloxy)-7-oxo-1,6-diaza-bicyclo[3.2.1]octan-2-yl)-1,2,4-oxadiazol-3-yl)piperidine-1-carboxylate (960 mg, 2.0 mmol) in 16 mL of $CH_2Cl_2$ at 0° C.

The mixture was stiffed at 0° C. for 2 hrs, then concentrated to give (2S,5R)-6-(benzyloxy)-2-(3-(piperidin-4-yl)-1,2,4-oxadiazol-5-yl)-1,6-diaza-bicyclo[3.2.1]octan-7-one (1.1 g) as a brown oil, which was used directly in the next step. ESI-MS ($EI^+$, m/z): 384.2 $[M+H]^+$.

Step 3: DIPEA (1.6 mL, 10.0 mmol) was slowly added dropwise to a solution of (2S,5R)-6-(benzyloxy)-2-(3-(piperidin-4-yl)-1,2,4-oxadiazol-5-yl)-1,6-diaza-bicyclo[3.2.1]octan-7-one (1.1 g, 2.0 mmol) in THF (50 mL) at 0° C. The mixture was stiffed under $N_2$ atmosphere at 0° C. for 15 minutes, then, Fmoc-OSu (2.4 g, 7.2 mmol) was added and the mixture was stirred at rt. for 8 hrs. The mixture was concentrated and the residue was purified by silica gel column chromatography (gradient elution 1:6 to 1:2 EtOAc/hexanes) to give (9H-fluoren-9-yl)methyl 4-(5-((2S,5R)-6-(benzyloxy)-7-oxo-1,6-diaza-bicyclo[3.2.1]octan-2-yl)-1,2,4-oxadiazol-3-yl)piperidine-1-carboxylate (1.0 g, 86%) as a white solid.

Step 4: $BCl_3$ (8.5 ml, 8.5 mmol; 1 M in $CH_2Cl_2$) was added dropwise to a solution of (9H-fluoren-9-yl)methyl 4-(5-((2S,5R)-6-(benzyloxy)-7-oxo-1,6-diaza-bicyclo[3.2.1]octan-2-yl)-1,2,4-oxadiazol-3-yl)piperidine-1-carboxylate (1.0 g, 1.7 mmol, 1.0 eq.) in dried $CH_2Cl_2$ (20 mL) at −78° C. The mixture was stiffed under $N_2$ atmosphere at 0° C. for 6 hrs. Then, the reaction mixture was cooled to −78° C. and MeOH (2 mL) was added dropwise. The solvents were evaporated under vacuum at 0° C. to give ((9H-fluoren-9-yl)methyl 4-(5-((2S,5R)-6-hydroxy-7-oxo-1,6-diaza-bicyclo[3.2.1]octan-2-yl)-1,2,4-oxadiazol-3-yl)piperidine-1-carboxylate (970 mg) as a yellow solid, which was used directly in the next step. ESI-MS ($EI^-$, m/z): 516.3 $[M+H]^-$.

Step 5: To a solution of ((9H-fluoren-9-yl)methyl 4-(5-((2S,5R)-6-hydroxy-7-oxo-1,6-diaza-bicyclo[3.2.1]octan-2-yl)-1,2,4-oxadiazol-3-yl)piperidine-1-carboxylate (970 mg) in dry pyridine (15 mL) was added $SO_3$.Py (1.4 g, 8.5 mmol). The mixture was stirred at rt for 6 h and then concentrated under vacuum. The resulting residue was then re-dissolved in aqueous $NaH_2PO_4$ (1.5 M, 100 mL) and Tetrabutylammonium hydrogensulphate (746 mg) was added. The mixture was stirred at rt for 30 minutes, then extracted with EtOAc (4×). The combined organic layer was dried and concentrated and the residue was purified by silica gel column chromatography (gradient elution 10:1 to 2:1 $CH_2Cl_2$/acetone) to afford tetrabutylammonium (9H-fluoren-9-yl)methyl 4-(5-((2S,5R)-7-oxo-6-(sulfooxy)-1,6-diaza-bicyclo[3.2.1]octan-2-yl)-1,2,4-oxadiazol-3-yl)piperidine-1-carboxylate sulfate as a white solid (1.0 g, 71% for two steps). ESI-MS ($EI^-$, m/z): 594.1 $[M-H]^-$.

Step 6: $Et_2NH$ (6.1 mL, 60.0 mmol) was added to a solution of tetrabutylammonium (9H-fluoren-9-yl)methyl 4-(5-((2S,5R)-7-oxo-6-(sulfooxy)-1,6-diaza-bicyclo[3.2.1]octan-2-yl)-1,2,4-oxadiazol-3-yl)piperidine-1-carboxylate sulfate (1.0 g, 1.2 mmol) in dried $CH_2Cl_2$ (30 mL). The mixture was stirred under $N_2$ atmosphere at rt. for 12 hrs, then evaporated under vacuum. The residue was purified by prep-HPLC using the ammonium formate conditions. E SI-MS ($EI^+$, m/z): 314.2. $^1$H NMR (300 MHz, $D_2O$) δ 4.82 (d, J=8.0 Hz, 1H), 4.17 (br s, 1H), 3.47-3.45 (m, 2H), 3.25-3.12 (m, 3H), 2.96-2.92 (m, 1H), 2.39-1.94 (m, 8H).

Example 11

Construction of Isogenic β-Lactamase Strains

A set of β-lactamase expressing isogenic *E. coli* strains was constructed by cloning a β-lactamase gene into a customized derivative of pBR322 (GenBank Accession Number J01749) and transforming the engineered plasmids into *E. coli*. The NdeI restriction site within the plasmid backbone of pBR322 was removed to generate pBR322ΔNdeI. The pBR322ΔNdeI vector itself, minus the blaTEM-1 gene, was amplified using two primers: (1) pBR-Pbla 5'-cg catatgactcttcctttttcaatattattg-3, SEQ ID 1, a primer with an engineered NdeI restriction site at the 3' end of the blaTEM-1 promoter and (2) pBR-vec-1 5'-gc ggatccctgtcagaccaagtttactc-3', SEQ ID 2, a primer with an engineered BamHI restriction site at the 3' end of the blaTEM-1 open reading frame. The chloramphenicol resistance gene, cat, was generated by PCR amplification from pKD3 (GenBank Accession Number AY048742) using primers with an engineered NdeI restriction site at the 5' end (Pbla-cat 5'-gccatatgatggagaaaaaaatcactgg-3', SEQ ID 3) and an engineered BamHI restriction site at the 3' end (Vec-1-cat 5'-cgggatccctagagaataggaacttcgg-3', SEQ ID 4) of the resistance gene. The two PCR products, pBR322ΔNdeI and cat were ligated together generating pBR-CBST (pBR322ΔNdeI ΔTEM-1::cat Seq. ID 5) which retains both the pBR322 tetracycline resistance cassette, tetA, and the plasmid origin of replication but the blaTEM-1 gene was replaced by the cat gene.

Using this engineering strategy a number of plasmids producing β-lactamase genes from different classes (see below) were generated using synthetic genes with an engineered NdeI restriction site at the 5' end and BamHI restriction site at the 3' end of each gene (GenScript). Both the synthetic β-lactamase genes and cat gene were ligated into the NdeI/BamHI sites of the pBR322ΔNdeI PCR product and transformed into electrocompetent *E. coli* ElectroMax DH10B (Invitrogen/Life Technologies). *E. coli* DH10B harboring the recombinant plasmids were selected on LB agar (supplemented with 25 μg/mL tetracycline) and single isolated colonies were then inoculated into 5 mL LB media (supplemented with 25 μg/mL tetracycline), and incubated at 37° C. with aeration (250 rpm) for 18 hrs. The cultures were frozen back at −80° C. in 20% glycerol. The DNA sequence of the cloned β-lactamase genes was confirmed. The β-lactamase gene expression in the recombinant *E. coli* strains was driven by the blaTEM-1 promoter in the pBR-CBST plasmid and was characterized by MIC profiling of the *E. coli* recombinant strains against comparator β-lactam/BLI combinations in broth microdilution assay.

| β-Lactamase Expressing Strain | Name & SEQ. ID of plasmids producing β-Lactamase | β-Lactamase Class | Species Origin of β-Lactamase Gene | GenBank Accession Number of β-Lactamase Gene Sequence |
|---|---|---|---|---|
| KPC-2 | pBR-CBST-KPC-2 SEQID 6 | A | *K. pneumoniae* | EU784136 |

-continued

| β-Lactamase Expressing Strain | Name & SEQ. ID of plasmids producing β-Lactamase | β-Lactamase Class | Species Origin of β-Lactamase Gene | GenBank Accession Number of β-Lactamase Gene Sequence |
|---|---|---|---|---|
| CTX-M-15 | pBR-CBST-CTX-M-15 SEQ ID 7 | A | *K. pneumoniae* | JF775516 |
| SHV-12 | pBR-CBST-SHV-12 SEQ ID 8 | A | *K. pneumoniae* | AY008838 |
| P99 AmpC | pBR-CBST-P99 AMPC SEQ ID 9 | C | *E. cloacea* | X07274 |
| OXA-15 | pBR-CBST-OXA-15 SEQ ID 10 | D | *P. aeruginosa* | PAU63835 |
| KPC-4 | pBR-CBST-KPC-4 SEQ ID 11 | A | *K. pneumoniae* | EU447304 |
| DHA-1 | pBR-CBST-DHA-1 SEQ ID 12 | C | *K. pneumoniae* | AY585202 |
| ADC-33 | pBR-CBST-ADC-33 SEQ ID 13 | C | *A.baumannii* | EU687478 |

Nucleotide Sequences of pBR-CBST Plasmids (Containing β-Lactamase or cat Genes) Used in the *E. coli* Isogenic Strains (relevant restriction sites are underlined; β-lactamase sequences in all caps, tetA sequence is in italics)

pBR-CBST-cat

SEQ ID 5 ttcttgaagacgaaagggcctcgtgatacgcctatttttataggttaatgt catgataataatggtttcttagacgtcaggtggcacttttcggggaaatgt gcgcggaacccctatttgtttatttttctaaatacattcaaatatgtatcc gctcatgagacaataaccctgataaatgcttcaataatattgaaaaaggaa gagtcatATGGAGAAAAAAATCACTGGATATACCACCGTTGATATATCCCA

ATGGCATCGTAAAGAACATTTTGAGGCATTTCAGTCAGTTGCTCAATGTAC

CTATAACCAGACCGTTCAGCTGGATATTACGGCCTTTTTAAAGACCGTAAA

GAAAAATAAGCACAAGTTTTATCCGGCCTTTATTCACATTCTTGCCCGCCT

GATGAATGCTCATACGGAATTTCGTATGGCAATGAAAGACGGTGAGCTGGT

GATATGGGATAGTGTTCACCCTTGTTACACCGTTTTCCATGAGCAAACTGA

AACGTTTTCATCGCTCTGGAGTGAATACCACGACGATTTCCGGCAGTTTCT

ACACATATATTCGCAAGATGTGGCGTGTTACGGTGAAAACCTGGCCTATTT

CCCTAAAGGGTTTATTGAGAATATGTTTTTCGTCTCAGCCAATCCCTGGGT

GAGTTTCACCAGTTTTGATTTAAACGTGGCCAATATGGACAACTTCTTCGC

CCCCGTTTTCACTATGGGCAAATATTATACGCAAGGCGACAAGGTGCTGAT

GCCGCTGGCGATTCAGGTTCATCATGCCGTCTGTGATGGCTTCCATGTCGG

CAGAATGCTTAATGAATTACAACAGTACTGCGATGAGTGGCAGGGCGGGGC

GTAAGTGGCAGGGCGGGGCGTAAGGCGCGCCATTTAAATGAAGTTCCTATT

CCGAAGTTCCTATTCTCTAGggatccctgtcagaccaagtttactcatata tactttagattgatttaaaacttcatttttaatttaaaaggatctaggtga -continued agatcctttttgataatctcatgaccaaaatcccttaacgtgagttttcgt tccactgagcgtcagaccccgtagaaaagatcaaaggatcttcttgagatc ctttttttctgcgcgtaatctgctgcttgcaaacaaaaaaaccaccgctac cagcggtggtttgtttgccggatcaagagctaccaactctttttccgaagg taactggcttcagcagagcgcagataccaaatactgtccttctagtgtagc cgtagttaggccaccacttcaagaactctgtagcaccgcctacatacctcg ctctgctaatcctgttaccagtggctgctgccagtggcgataagtcgtgtc ttaccgggttggactcaagacgatagttaccggataaggcgcagcggtcgg gctgaacggggggttcgtgcacacagcccagcttggagcgaacgacctaca ccgaactgagatacctacagcgtgagctatgagaaagcgccacgcttcccg aagggagaaaggcggacaggtatccggtaagcggcagggtcggaacaggag agcgcacgagggagcttccagggggaaacgcctggtatctttatagtcctg tcgggtttcgccacctctgacttgagcgtcgatttttgtgatgctcgtcag gggggcggagcctatggaaaaacgccagcaacgcggcctttttacggttcc tggccttttgctggccttttgctcacatgttctttcctgcgttatcccctg attctgtggataaccgtattaccgcctttgagtgagctgataccgctcgcc gcagccgaacgaccgagcgcagcgagtcagtgagcgaggaagcggaagagc gcctgatgcggtattttctccttacgcatctgtgcggtatttcacaccgca tttggtgcactctcagtacaatctgctctgatgccgcatagttaagccagt atacactccgctatcgctacgtgactgggtcatggctgcgccccgacaccc gccaacacccgctgacgcgccctgacgggcttgtctgctcccggcatccgc ttacagacaagctgtgaccgtctccgggagctgcatgtgtcagaggttttc accgtcatcaccgaaacgcgcgaggcagctgcggtaaagctcatcagcgtg gtcgtgaagcgattcacagatgtctgcctgttcatccgcgtccagctcgtt -continued gagtttctccagaagcgttaatgtctggcttctgataaagcgggccatgtt
aagggcggtttttcctgtttggtcactgatgcctccgtgtaagggggatt
tctgttcatgggggtaatgataccgatgaaacgagagaggatgctcacgat
acgggttactgatgatgaacatgcccggttactggaacgttgtgagggtaa
acaactggcggtatggatgcggcgggaccagagaaaaatcactcagggtca
atgccagcgcttcgttaatacagatgtaggtgttccacagggtagccagca
gcatcctgcgatgcagatccggaacataatggtgcagggcgctgacttccg
cgtttccagactttacgaaacacggaaaccgaagaccattcatgttgttgc
tcaggtcgcagacgttttgcagcagcagtcgcttcacgttcgctcgcgtat
cggtgattcattctgctaaccagtaaggcaaccccgccagcctagccgggt
cctcaacgacaggagcacgatcatgcgcacccgtggccaggacccaacgct
gcccgagatgcgccgcgtgcggctgctggagatggcggacgcgatggatat
gttctgccaagggttggtttgcgcattcacagttctccgcaagaattgatt
ggctccaattcttggagtggtgaatccgttagcgaggtgccgccggcttcc
at*tcaggtcgaggtggcccggctccatgcaccgcgacgcaacgcggggagg*
*cagacaaggtatagggcggcgcctacaatccatgccaacccgttccatgtg*
*ctcgccgaggcggcataaatcgccgtgacgatcagcggtccagtgatcgaa*
*gttaggctggtaagagccgcgagcgatccttgaagctgtccctgatggtcg*
*tcatctacctgcctggacagcatggcctgcaacgcgggcatcccgatgccg*
*ccggaagcgagaagaatcataatggggaaggccatccagcctcgcgtcgcg*
*aacgccagcaagacgtagcccagcgcgtcggccgccatgccggcgataatg*
*gcctgcttctcgccgaaacgtttggtggcgggaccagtgacgaaggcttga*
*gcgagggcgtgcaagattccgaataccgcaagcgacaggccgatcatcgtc*
*gcgctccagcgaaagcggtcctcgccgaaaatgacccagagcgctgccggc*
*acctgtcctacgagttgcatgataaagaagacagtcataagtgcggcgacg*
*atagtcatgccccgcgcccaccggaaggagctgactgggttgaaggctctc*
*aagggcatcggtcgacgctctcccttatgcgactcctgcattaggaagcag*
*cccagtagtaggttgaggccgttgagcaccgccgccgcaaggaatggtgca*
*tgcaaggagatggcgcccaacagtcccccggccacggggcctgccaccata*
*cccacgccgaaacaagcgctcatgagcccgaagtggcgagcccgatcttcc*
*ccatcggtgatgtcggcgatataggcgccagcaaccgcacctgtggcgccg*
*gtgatgccggccacgatgcgtccggcgtagaggattcacaggacgggtgtg*
*gtcgccatgatcgcgtagtcgatagtggctccaagtagcgaagcgagcagg*
*actgggcggcggccaaagcggtcggacagtgctccgagaacgggtgcgcat*
*agaaattgcatcaacgcatatagcgctagcagcacgccatagtgactggcg*
*atgctgtcggaatggacgatatcccgcaagaggcccggcagtaccggcata*
*accaagcctatgcctacagcatccagggtgacggtgccgaggatgacgatg*
*agcgcattgttagatttcat*acacggtgcctgactgcgttagcaatttaac
tgtgataaactaccgcattaaagcttatcgatgataagctgtcaaacatga
gaa -continued pBR-CBST-KPC-2

SEQ ID 6 ttcttgaagacgaaagggcctcgtgatacgcctatttttataggttaatgt
catgataataatggtttcttagacgtcaggtggcacttttcggggaaatgt
gcgcggaacccctatttgtttatttttctaaatacattcaaatatgtatcc
gctcatgagacaataaccctgataaatgcttcaataatattgaaaaaggaa
gagtcatATGTCACTGTATCGCCGTCTAGTTCTGCTGTCTTGTCTCTCATG
GCCGCTGGCTGGCTTTTCTGCCACCGCGCTGACCAACCTCGTCGCGGAACC
ATTCGCTAAACTCGAACAGGACTTTGGCGGCTCCATCGGTGTGTACGCGAT
GGATACCGGCTCAGGCGCAACTGTAAGTTACCGCGCTGAGGAGCGCTTCCC
ACTGTGCAGCTCATTCAAGGGCTTTCTTGCTGCCGCTGTGCTGGCTCGCAG
CCAGCAGCAGGCCGGCTTGCTGGACACACCCATCCGTTACGGCAAAAATGC
GCTGGTTCCGTGGTCACCCATCTCGGAAAAATATCTGACAACAGGCATGAC
GGTGGCGGAGCTGTCCGCGGCCGCCGTGCAATACAGTGATAACGCCGCCGC
CAATTTGTTGCTGAAGGAGTTGGGCGGCCCGGCCGGGCTGACGGCCTTCAT
GCGCTCTATCGGCGATACCACGTTCCGTCTGGACCGCTGGGAGCTGGAGCT
GAACTCCGCCATCCCAGGCGATGCGCGCGATACCTCATCGCCGCGCGCCGT
GACGGAAAGCTTACAAAAACTGACACTGGGCTCTGCACTGGCTGCGCCGCA
GCGGCAGCAGTTTGTTGATTGGCTAAAGGGAAACACGACCGGCAACCACCG
CATCCGCGCGGCGGTGCCGGCAGACTGGGCAGTCGGAGACAAAACCGGAAC
CTGCGGAGTGTATGGCACGGCAAATGACTATGCCGTCGTCTGGCCCACTGG
GCGCGCACCTATTGTGTTGGCCGTCTACACCCGGGCGCCTAACAAGGATGA
CAAGCACAGCGAGGCCGTCATCGCCGCTGCGGCTAGACTCGCGCTCGAGGG
ATTGGGCGTCAACGGGCAGTAAggatccctgtcagaccaagtttactcata
tatactttagattgatttaaaacttcatttttaatttaaaaggatctaggt
gaagatcctttttgaiaatctcatgaccaaaatcccttaacgtgagttttc
gttccactgagcgtcagaccccgtagaaaagatcaaaggatcttcttgaga
tcctttttttctgcgcgtaatctgctgcttgcaaacaaaaaaaccaccgct
accagcggtggtttgtttgccggatcaagagctaccaactctttttccgaa
ggtaactggcttcagcagagcgcagataccaaatactgtccttctagtgta
gccgtagttaggccaccacttcaagaactctgtagcaccgcctacatacct
cgctctgctaatcctgttaccagtggctgctgccagtggcgataagtcgtg
tcttaccgggttggactcaagacgatagttaccggataaggcgcagcggtc
gggctgaacggggggttcgtgcacacagcccagcttggagcgaacgaccta
caccgaactgagatacctacagcgtgagctatgagaaagcgccacgcttcc
cgaagggagaaaggcggacaggtatccggtaagcggcagggtcggaacagg
agagcgcacgagggagcttccagggggaaacgcctggtatctttatagtcc
tgtcgggtttcgccacctctgacttgagcgtcgatttttgtgatgctcgtc
aggggggcggagcctatggaaaaacgccagcaacgcggcctttttacggtt
cctggccttttgctggccttttgctcacatgttctttcctgcgttatcccc
tgattctgtggataaccgtattaccgcctttgagtgagctgataccgctcg -continued ccgcagccgaacgaccgagcgcagcgagtcagtgagcgaggaagcggaaga
gcgcctgatgcggtattttctccttacgcatctgtgcggtatttcacaccg
catttggtgcactctcagtacaatctgctctgatgccgcatagttaagcca
gtatacactccgctatcgctacgtgactgggtcatggctgcgccccgacac
ccgccaacacccgctgacgcgccctgacgggcttgtctgctcccggcatcc
gcttacagacaagctgtgaccgtctccgggagctgcatgtgtcagaggttt
tcaccgtcatcaccgaaacgcgcgaggcagctgcggtaaagctcatcagcg
tggtcgtgaagcgattcacagatgtctgcctgttcatccgcgtccagctcg
ttgagtttctccagaagcgttaatgtctggcttctgataaagcgggccatg
ttaagggcggtttttcctgtttggtcactgatgcctccgtgtaaggggga
tttctgttcatgggggtaatgataccgatgaaacgagagaggatgctcacg
atacgggttactgatgatgaacatgcccggttactggaacgttgtgagggt
aaacaactggcggtatggatgcggcgggaccagagaaaaatcactcagggt
caatgccagcgcttcgttaatacagatgtaggtgttccacagggtagccag
cagcatcctgcgatgcagatccggaacataatggtgcagggcgctgacttc
cgcgtttccagactttacgaaacacggaaaccgaagaccattcatgttgtt
gctcaggtcgcagacgttttgcagcagcagtcgcttcacgttcgctcgcgt
atcggtgattcattctgctaaccagtaaggcaaccccgccagcctagccgg
gtcctcaacgacaggagcacgatcatgcgcacccgtggccaggacccaacg
ctgcccgagatgcgccgcgtgcggctgctggagatggcggacgcgatggat
atgttctgccaagggttggtttgcgcattcacagttctccgcaagaattga
ttggctccaattcttggagtggtgaatccgttagcgaggtgccgccggctt
ccat*tcaggtcgaggtggcccggctccatgcaccgcgacgcaacgcgggga*
*ggcagacaaggtatagggcggcgcctacaatccatgccaacccgttccatg*
*tgctcgccgaggcggcataaatcgccgtgacgatcagcggtccagtgatcg*
*aagttaggctggtaagagccgcgagcgatccttgaagctgtccctgatggt*
*cgtcatctacctgcctggacagcatggcctgcaacgcgggcatcccgatgc*
*cgccggaagcgagaagaatcataatggggaaggccatccagcctcgcgtcg*
*cgaacgccagcaagacgtagcccagcgcgtcggccgccatgccggcgataa*
*tggcctgcttctcgccgaaacgtttggtggcgggacagtgacgaaggcttg*
*agcgagggcgtgcaagattccgaataccgcaagcgacaggccgatcatcgt*
*cgcgctccagcgaaagcggtcctcgccgaaaatgaccagagcgctgccggc*
*acctgtcctacgagttgcatgataaagaagacagtcataagtgcggcgacg*
*atagtcatgccccgcgcccaccggaaggagctgactgggttgaaggctctc*
*aagggcatcggtcgacgctctcccttatgcgactcctgcattaggaagcag*
*cccagtagtaggttgaggccgttgagcaccgccgccgcaaggaatggtgca*
*tgcaaggagatggcgcccaacagtcccccggccacggggcctgccaccata*
*cccacgccgaaacaagcgctcatgagcccgaagtggcgagcccgatcttcc*
*ccatcggtgatgtcggcgatataggcgccagcaaccgcacctgtggcgccg*
*gtgatgccggccacgatgcgtccggcgtagaggattcacaggacgggtgtg*
*gtcgccatgatcgcgtagtcgatagtggctccaagtagcgaagcgagcagg*

-continued

*actgggcggcggccaaagcggtcggacagtgctccgagaacgggtgcgcat*
*agaaattgcatcaacgcatatagcgctagcagcacgccatagtgactggcg*
*atgctgtcggaatggacgatatcccgcaagaggcccggcagtaccggcata*
*accaagcctatgcctacagcatccagggtgacggtgccgaggatgacgatg*
*agcgcattgttagatttcat*acacggtgcctgactgcgttagcaatttaac
tgtgataaactaccgcattaaagcttatcgatgataagctgtcaaacatga
gaa pBR-CBST-CTX-M-15

SEQ ID 7 ttcttgaagacgaaagggcctcgtgatacgcctatttttataggttaatgt
catgataataatggtttcttagacgtcaggtggcacttttcggggaaatgt
gcgcggaacccctatttgtttatttttctaaatacattcaaatatgtatcc
gctcatgagacaataaccctgataaatgcttcaataatattgaaaaaggaa
gagtcatATGGAATCTGTTAAATCAGCGAGTTGAGATCAAAAAATCTGACC
TTGTTAACTATAATCCGATTGCGGAAAAGCACGTCAATGGGACGATGTCAC
TGGCTGAGCTTAGCGCGGCCGCGCTACAGTACAGCGATAACGTGGCGATGA
ATAAGCTGATTGCTCACGTTGGCGGCCCGGCTAGCGTCACCGCGTTCGCCC
GACAGCTGGGAGACGAAACGTTCCGTCTCGACCGTACCGAGCCGACGTTAA
ACACCGCCATTCCGGGCGATCCGCGTGATACCACTTCACCTCGGGCAATGG
CGCAAACTCTGCGGAATCTGACGCTGGGTAAAGCATTGGGCGACAGCCAAC
GGGCGCAGCTGGTGACATGGATGAAAGGCAATACCACCGGTGCAGCGAGCA
TTCAGGCTGGACTGCCTGCTTCCTGGGTTGTGGGGGATAAAACCGGCAGCG
GTGGCTATGGCACCACCAACGATATCGCGGTGATCTGGCCAAAAGATCGTG
CGCCGCTGATTCTGGTCACTTACTTCACCCAGCCTCAACCTAAGGCAGAAA
GCCGTCGCGATGTATTAGCGTCGGCGGCTAAAATCGTCACCGACGGTTTGT
AAggatccctgtcagaccaagtttactcatatatactttagattgatttaa
aacttcattttaatttaaaaggatctaggtgaagatcctttttgataatc
tcatgaccaaaatcccttaacgtgagttttcgttccactgagcgtcagacc
ccgtagaaaagatcaaaggatcttcttgagatcctttttttctgcgcgtaa
tctgctgcttgcaaacaaaaaaaccaccgctaccagcggtggtttgtttgc
cggatcaagagctaccaactctttttccgaaggtaactggcttcagcagag
cgcagataccaaatactgtccttctagtgtagccgtagttaggccaccact
tcaagaactctgtagcaccgcctacatacctcgctctgctaatcctgttac
cagtggctgctgccagtggcgataagtcgtgtcttaccgggttggactcaa
gacgatagttaccggataaggcgcagcggtcgggctgaacggggggttcgt
gcacacagcccagcttggagcgaacgacctacaccgaactgagatacctac
agcgtgagctatgagaaagcgccacgcttcccgaagggagaaaggcggaca
ggtatccggtaagcggcagggtcggaacaggagagcgcacgagggagcttc
cagggggaaacgcctggtatctttatagtcctgtcgggtttcgccacctct
gacttgagcgtcgatttttgtgatgctcgtcagggggggcggagcctatgga
aaaacgccagcaacgcggcctttttacggttcctggcctttttgctggcctt -continued ttgctcacatgttctttcctgcgttatcccctgattctgtggataaccgta ttaccgcctttgagtgagctgataccgctcgccgcagccgaacgaccgagc gcagcgagtcagtgagcgaggaagcggaagagcgcctgatgcggtatttc tccttacgcatctgtgcggtatttcacaccgcatttggtgcactctcagta caatctgctctgatgccgcatagttaagccagtatacactccgctatcgct acgtgactgggtcatggctgcgccccgacacccgccaacacccgctgacgc gccctgacgggcttgtctgctcccggcatccgcttacagacaagctgtgac cgtctccgggagctgcatgtgtcagaggttttcaccgtcatcaccgaaacg cgcgaggcagctgcggtaaagctcatcagcgtggtcgtgaagcgattcaca gatgtctgcctgttcatccgcgtccagctcgttgagtttctccagaagcgt taatgtctggcttctgataaagcgggccatgttaagggcggttttttcctg tttggtcactgatgcctccgtgtaagggggatttctgttcatgggggtaat gataccgatgaaacgagagaggatgctcacgatacgggttactgatgatga acatgcccggttactggaacgttgtgagggtaaacaactggcggtatggat gcggcgggaccagagaaaaatcactcagggtcaatgccagcgcttcgttaa tacagatgtaggtgttccacagggtagccagcagcatcctgcgatgcagat ccggaacataatggtgcagggcgctgacttccgcgtttccagactttacga aacacggaaaccgaagaccattcatgttgttgctcaggtcgcagacgtttt gcagcagcagtcgcttcacgttcgctcgcgtatcggtgattcattctgcta accagtaaggcaaccccgccagcctagccgggtcctcaacgacaggagcac gatcatgcgcacccgtggccaggacccaacgctgcccgagatgcgccgcgt gcggctgctggagatggcggacgcgatggatatgttctgccaagggttggt ttgcgcattcacagttctccgcaagaattgattggctccaattcttggagt ggtgaatccgttagcgaggtgccgccggcttccatt*caggtcgaggtggcc*

*cggctccatgcaccgcgacgcaacgcggggaggcagacaaggtatagggcg*

*gcgcctacaatccatgccaacccgttccatgtgctcgccgaggcggcataa*

*atcgccgtgacgatcagcggtccagtgatcgaagttaggctggtaagagcc*

*gcgagcgatccttgaagctgtccctgatggtcgtcatctacctgcctggac*

*agcatggcctgcaacgcgggcatcccgatgccgccggaagcgagaagaatc*

*ataatggggaaggccatccagcctcgcgtcgcgaacgccagcaagacgtag*

*cccagcgcgtcggccgccatgccggcgataatggcctgcttctcgccgaaa*

*cgtttggtggcgggaccagtgacgaaggcttgagcgagggcgtgcaagatt*

*ccgaataccgcaagcgacaggccgatcatcgtcgcgctccagcgaaagcgg*

*tcctcgccgaaaatgacccagagcgctgccggcacctgtcctacgagttgc*

*atgataaagaagacagtcataagtgcggcgacgatagtcatgccccgcgcc*

*caccggaaggagctgactgggttgaaggctctcaagggcatcggtcgacgc*

*tctcccttatgcgactcctgcattaggaagcagcccagtagtaggttgagg*

*ccgttgagcaccgccgccgcaaggaatggtgcatgcaaggagatggcgccc*

*aacagtcccccggccacggggcctgccaccatacccacgccgaaacaagcg*

*ctcatgagcccgaagtggcgagcccgatcttccccatcggtgatgtcggcg*

*atataggcgccagcaaccgcacctgtggcgccggtgatgccggccacgatg*

-continued

*cgtccggcgtagaggattcacaggacgggtgtggtcgccatgatcgcgtag*

*tcgatagtggctccaagtagcgaagcgagcaggactgggcggcggccaaag*

*cggtcggacagtgctccgagaacgggtgcgcatagaaattgcatcaacgca*

*tatagcgctagcagcacgccatagtgactggcgatgctgtcggaatggacg*

*atatcccgcaagaggcccggcagtaccggcataaccaagcctatgcctaca*

*gcatccagggtgacggtgccgaggatgacgatgagcgcattgttagatttc* atacacggtgcctgactgcgttagcaatttaactgtgataaactaccgcat taaagcttatcgatgataagctgtcaaacatgagaa pBR-CBST-SHV-12

SEQ ID 8 ttcttgaagacgaaagggcctcgtgatacgcctatttttataggttaatgt catgataataatggtttcttagacgtcaggtggcacttttcggggaaatgt gcgcggaacccctatttgtttatttttctaaatacattcaaatatgtatcc gctcatgagacaataaccctgataaatgcttcaataatattgaaaaaggaa gagt<u>catATG</u>CGTTATATTCGCCTGTGTATTATCTCCCTGTTAGCCACCCT

GCCGCTGGCGGTACACGCCAGCCCGCAGCCGCTTGAGCAAATTAAACAAAG

CGAAAGCCAGCTGTCGGGCCGCGTAGGCATGATAGAAATGGATCTGGCCAG

CGGCCGCACGCTGACCGCCTGGCGCGCCGATGAACGCTTTCCCATGATGAG

CACCTTTAAAGTAGTGCTCTGCGGCGCAGTGCTGGCGCGGGTGGATGCCGG

TGACGAACAGCTGGAGCGAAAGATCCACTATCGCCAGCAGGATCTGGTGGA

CTACTCGCCGGTCAGCGAAAAACACCTTGCCGACGGCATGACGGTCGGCGA

ACTCTGCGCCGCCGCCATTACCATGAGCGATAACAGCGCCGCCAATCTGCT

GCTGGCCACCGTCGGCGGCCCCGCAGGATTGACTGCCTTTTTGCGCCAGAT

CGGCGACAACGTCACCCGCCTTGACCGCTGGGAAACGGAACTGAATGAGGC

GCTTCCCGGCGACGCCCGCGACACCACTACCCCGGCCAGCATGGCCGCGAC

CCTGCGCAAGCTGCTGACCAGCCAGCGTCTGAGCGCCCGTTCGCAACGGCA

GCTGCTGCAGTGGATGGTGGACGATCGGGTCGCCGGACCGTTGATCCGCTC

CGTGCTGCCGGCGGGCTGGTTTATCGCCGATAAGACCGGAGCTAGCAAGCG

GGGTGCGCGCGGGATTGTCGCCCTGCTTGGCCCGAATAACAAAGCAGAGCG

CATTGTGGTGATTTATCTGCGGGATACCCCGGCGAGCATGGCCGAGCGAAA

TCAGCAAATCGCCGGGATCGGCGCGGCGCTGATCGAGCACTGGCAACGCTA

<u>Aggatcc</u>ctgtcagaccaagtttactcatatatactttagattgatttaaa acttcatttttaatttaaaaggatctaggtgaagatcctttttgataatct catgaccaaaatcccttaacgtgagttttcgttccactgagcgtcagaccc cgtagaaaagatcaaaggatcttcttgagatcctttttttctgcgcgtaat ctgctgcttgcaaacaaaaaaaccaccgctaccagcggtggtttgtttgcc ggatcaagagctaccaactctttttccgaaggtaactggcttcagcagagc gcagataccaaatactgtccttctagtgtagccgtagttaggccaccactt caagaactctgtagcaccgcctacatacctcgctctgctaatcctgttacc agtggctgctgccagtggcgataagtcgtgtcttaccgggttggactcaag acgatagttaccggataaggcgcagcggtcgggctgaacggggggttcgtg -continued cacacagcccagcttggagcgaacgacctacaccgaactgagatacctaca gcgtgagctatgagaaagcgccacgcttcccgaagggagaaaggcggacag gtatccggtaagcggcagggtcggaacaggagagcgcacgagggagcttcc agggggaaacgcctggtatctttatagtcctgtcgggtttcgccacctctg acttgagcgtcgatttttgtgatgctcgtcaggggggcggagcctatggaa aaacgccagcaacgcggcctttttacggttcctggccttttgctggcctttt tgctcacatgttctttcctgcgttatcccctgattctgtggataaccgtat taccgcctttgagtgagctgataccgctcgccgcagccgaacgaccgagcg cagcgagtcagtgagcgaggaagcggaagagcgcctgatgcggtattttct ccttacgcatctgtgcggtatttcacaccgcatttggtgcactctcagtac aatctgctctgatgccgcatagttaagccagtatacactccgctatcgcta cgtgactgggtcatggctgcgccccgacacccgccaacacccgctgacgcg ccctgacgggcttgtctgctcccggcatccgcttacagacaagctgtgacc gtctccgggagctgcatgtgtcagaggttttcaccgtcatcaccgaaacgc gcgaggcagctgcggtaaagctcatcagcgtggtcgtgaagcgattcacag atgtctgcctgttcatccgcgtccagctcgttgagtttctccagaagcgtt aatgtctggcttctgataaagcgggccatgttaagggcggtttttttcctgt ttggtcactgatgcctccgtgtaagggggatttctgttcatgggggtaatg ataccgatgaaacgagagaggatgctcacgatacgggttactgatgatgaa catgcccggttactggaacgttgtgagggtaaacaactggcggtatggatg cggcgggaccagagaaaaatcactcagggtcaatgccagcgcttcgttaat acagatgtaggtgttccacagggtagccagcagcatcctgcgatgcagatc cggaacataatggtgcagggcgctgacttccgcgtttccagactttacgaa acacggaaaccgaagaccattcatgttgttgctcaggtcgcagacgttttg cagcagcagtcgcttcacgttcgctcgcgtatcggtgattcattctgctaa ccagtaaggcaaccccgccagcctagccgggtcctcaacgacaggagcacg atcatgcgcacccgtggccaggacccaacgctgcccgagatgcgccgcgtg cggctgctggagatggcggacgcgatggatatgttctgccaagggttggtt tgcgcattcacagttctccgcaagaattgattggctccaattcttggagtg gtgaatccgttagcgaggtgccgccggcttccat*tcaggtcgaggtggccc*

*ggctccatgcaccgcgacgcaacgcggggaggcagacaaggtatagggcgg*

*cgcctacaatccatgccaacccgttccatgtgctcgccgaggcggcataaa*

*tcgccgtgacgatcagcggtccagtgatcgaagttaggctggtaagagccg*

*cgagcgatccttgaagctgtccctgatggtcgtcatctacctgcctggaca*

*gcatggcctgcaacgcgggcatcccgatgccgccggaagcgagaagaatca*

*taatggggaaggccatccagcctcgcgtcgcgaacgccagcaagacgtagc*

*ccagcgcgtcggccgccatgccggcgataatggcctgcttctcgccgaaac*

*gtttggtggcgggaccagtgacgaaggcttgagcgagggcgtgcaagattc*

*cgaataccgcaagcgacaggccgatcatcgtcgcgctccagcgaaagcggt*

*cctcgccgaaaatgacccagagcgctgccggcacctgtcctacgagttgca*

*tgataaagaagacagtcataagtgcggcgacgatagtcatgccccgcgccc*

-continued

*accggaaggagctgactgggttgaaggctctcaagggcatcggtcgacgct*

*ctcccttatgcgactcctgcattaggaagcagcccagtagtaggttgaggc*

*cgttgagcaccgccgccgcaaggaatggtgcatgcaaggagatggcgccca*

*acagtcccccggccacggggcctgccaccatacccacgccgaaacaagcgc*

*tcatgagcccgaagtggcgagcccgatcttccccatcggtgatgtcggcga*

*tataggcgccagcaaccgcacctgtggcgccggtgatgccggccacgatgc*

*gtccggcgtagaggattcacaggacgggtgtggtcgccatgatcgcgtagt*

*cgatagtggctccaagtagcgaagcgagcaggactgggcggcggccaaagc*

*ggtcggacagtgctccgagaacgggtgcgcatagaaattgcatcaacgcat*

*atagcgctagcagcacgccatagtgactggcgatgctgtcggaatggacga*

*tatcccgcaagaggcccggcagtaccggcataaccaagcctatgcctacag*

*catccagggtgacggtgccgaggatgacgatgagcgcattgttagatttca* tacacggtgcctgactgcgttagcaatttaactgtgataaactaccgcatt aaagcttatcgatgataagctgtcaaacatgagaa pBR-CBST-P99

SEQ ID 9 ttcttgaagacgaaagggcctcgtgatacgcctatttttataggttaatgt catgataataatggtttcttagacgtcaggtggcacttttcggggaaatgt gcgcggaacccctatttgtttatttttctaaatacattcaaatatgtatcc gctcatgagacaataaccctgataaatgcttcaataatattgaaaaaggaa gagtcatATGATGAGAAAATCCCTTTGCTGCGCCCTGCTGCTCGGCATCTC

TTGCTCTGCTCTCGCCACGCCAGTGTCAGAAAAACAGCTGGCGGAGGTGGT

CGCGAATACGATTACCCCGCTGATGAAAGCCCAGTCTGTTCCAGGCATGGC

GGTGGCCGTTATTTATCAGGGAAAACCGCACTATTACACATTTGGCAAGGC

CGATATCGCGGCGAATAAACCCGTTACGCCTCAGACCCTGTTCGAGCTGGG

TTCTATAAGTAAAACCTTCACCGGCGTTTTAGGTGGGGATGCCATTGCTCG

CGGTGAAATTTCGCTGGACGATGCGGTGACCAGATACTGGCCACAGCTGAC

GGGCAAGCAGTGGCAGGGTATTCGTATGCTGGATCTCGCCACCTACACCGC

TGGCGGCCTGCCGCTACAGGTACCGGATGAGGTCACGGATAACGCCTCCCT

GCTGCGCTTTTATCAAAACTGGCAGCCGCAGTGGAAGCCTGGCACAACGCG

TCTTTACGCCAACGCCAGCATCGGTCTTTTTGGTGCGCTGGCGGTCAAACC

TTCTGGCATGCCCTATGAGCAGGCCATGACGACGCGGGTCCTTAAGCCGCT

CAAGCTGGACCATACCTGGATTAACGTGCCGAAAGCGGAAGAGGCGCATTA

CGCCTGGGGCTATCGTGACGGTAAAGCGGTGCGCGTTTCGCCGGGTATGCT

GGATGCACAAGCCTATGGCGTGAAAACCAACGTGCAGGATATGGCGAACTG

GGTCATGGCAAACATGGCGCCGGAGAACGTTGCTGATGCCTCACTTAAGCA

GGGCATCGCGCTGGCGCAGTCGCGCTACTGGCGTATCGGGTCAATGTATCA

GGGTCTGGGCTGGGAGATGCTCAACTGGCCCGTGGAGGCCAACACGGTGGT

CGAGGGCAGCGACAGTAAGGTAGCACTGGCGCCGTTGCCCGTGGCAGAAGT

GAATCCACCGGCTCCCCCGGTCAAAGCGTCCTGGGTCCATAAAACGGGCTC

TACTGGCGGGTTTGGCAGCTACGTGGCCTTTATTCCTGAAAAGCAGATCGG

-continued

TATTGTGATGCTCGCGAATACAAGCTATCCGAACCCGGCACGCGTTGAGGC
GGCATACCATATCCTCGAGGCGCTACAGTAAggatccctgtcagaccaagt
ttactcatatatactttagattgatttaaaacttcatttttaatttaaaag
gatctaggtgaagatcctttttgataatctcatgaccaaaatcccttaacg
tgagttttcgttccactgagcgtcagaccccgtagaaaagatcaaaggatc
ttcttgagatcctttttttctgcgcgtaatctgctgcttgcaaacaaaaaa
accaccgctaccagcggtggtttgtttgccggatcaagagctaccaactct
ttttccgaaggtaactggcttcagcagagcgcagataccaaatactgtcct
tctagtgtagccgtagttaggccaccacttcaagaactctgtagcaccgcc
tacatacctcgctctgctaatcctgttaccagtggctgctgccagtggcga
taagtcgtgtcttaccgggttggactcaagacgatagttaccggataaggc
gcagcggtcgggctgaacggggggttcgtgcacacagcccagcttggagcg
aacgacctacaccgaactgagatacctacagcgtgagctatgagaaagcgc
cacgcttcccgaagggagaaaggcggacaggtatccggtaagcggcagggt
cggaacaggagagcgcacgagggagcttccagggggaaacgcctggtatct
ttatagtcctgtcgggtttcgccacctctgacttgagcgtcgatttttgtg
atgctcgtcaggggggcggagcctatggaaaaacgccagcaacgcggcctt
tttacggttcctggccttttgctggccttttgctcacatgttctttcctgc
gttatcccctgattctgtggataaccgtattaccgcctttgagtgagctga
taccgctcgccgcagccgaacgaccgagcgcagcgagtcagtgagcgagga
agcggaagagcgcctgatgcggtattttctccttacgcatctgtgcggtat
ttcacaccgcatttggtgcactctcagtacaatctgctctgatgccgcata
gttaagccagtatacactccgctatcgctacgtgactgggtcatggctgcg
ccccgacacccgccaacacccgctgacgcgccctgacgggcttgtctgctc
ccggcatccgcttacagacaagctgtgaccgtctccgggagctgcatgtgt
cagaggttttcaccgtcatcaccgaaacgcgcgaggcagctgcggtaaagc
tcatcagcgtggtcgtgaagcgattcacagatgtctgcctgttcatccgcg
tccagctcgttgagtttctccagaagcgttaatgtctggcttctgataaag
cgggccatgttaagggcggtttttcctgtttggtcactgatgcctccgtg
taagggggatttctgttcatgggggtaatgataccgatgaaacgagagagg
atgctcacgatacgggttactgatgatgaacatgcccggttactggaacgt
tgtgagggtaaacaactggcggtatggatgcggcgggaccagagaaaaatc
actcagggtcaatgccagcgcttcgttaatacagatgtaggtgttccacag
ggtagccagcagcatcctgcgatgcagatccggaacataatggtgcagggc
gctgacttccgcgtttccagactttacgaaacacggaaaccgaagaccatt
catgttgttgctcaggtcgcagacgttttgcagcagcagtcgcttcacgtt
cgctcgcgtatcggtgattcattctgctaaccagtaaggcaaccccgccag
cctagccgggtcctcaacgacaggagcacgatcatgcgcacccgtggccag
gacccaacgctgcccgagatgcgcccgcgtgcggctgctggagatggcggac
gcgatggatatgttctgccaagggttggtttgcgcattcacagttctccgc
aagaattgattggctccaattcttggagtggtgaatccgttagcgaggtgc -continued cgccggcttccat*tcaggtcgaggtggcccggctccatgcaccgcgacgca*
*acgcggggaggcagacaaggtatagggcggcgcctacaatccatgccaacc*
*cgttccatgtgctcgccgaggcggcataaatcgccgtgacgatcagcggtc*
*cagtgatcgaagttaggctggtaagagccgcgagcgatccttgaagctgtc*
*cctgatggtcgtcatctacctgcctggacagcatggcctgcaacgcgggca*
*tcccgatgccgccggaagcgagaagaatcataatggggaaggccatccagc*
*ctcgcgtcgcgaacgccagcaagacgtagcccagcgcgtcggccgccatgc*
*cggcgataatggcctgcttctcgccgaaacgtttggtggcgggaccagtga*
*cgaaggcttgagcgagggcgtgcaagattccgaataccgcaagcgacaggc*
*cgatcatcgtcgcgctccagcgaaagcggtcctcgccgaaaatgacccaga*
*gcgctgccggcacctgtcctacgagttgcatgataaagaagacagtcataa*
*gtgcggcgacgatagtcatgccccgcgcccaccggaaggagctgactgggt*
*tgaaggctctcaagggcatcggtcgacgctctcccttatgcgactcctgca*
*ttaggaagcagcccagtagtaggttgaggccgttgagcaccgccgccgcaa*
*ggaatggtgcatgcaaggagatggcgcccaacagtcccccggccacggggc*
*ctgccaccatacccacgccgaaacaagcgctcatgagcccgaagtggcgag*
*cccgatcttccccatcggtgatgtcggcgatataggcgccagcaaccgcac*
*ctgtggcgccggtgatgccggccacgatgcgtccggcgtagaggattcaca*
*ggacgggtgtggtcgccatgatcgcgtagtcgatagtggctccaagtagcg*
*aagcgagcaggactgggcggcggccaaagcggtcggacagtgctccgagaa*
*cgggtgcgcatagaaattgcatcaacgcatatagcgctagcagcacgccat*
*agtgactggcgatgctgtcggaatggacgatatcccgcaagaggcccggca*
*gtaccggcataaccaagcctatgcctacagcatccagggtgacggtgccga*
*ggatgacgatgagcgcattgttagatttcat*acacggtgcctgactgcgtt
agcaatttaactgtgataaactaccgcattaaagcttatcgatgataagct
gtcaaacatgagaa pBR-CBST-OXA-15

SEQ ID 10 ttcttgaagacgaaagggcctcgtgatacgcctatttttataggttaatgt
catgataataatggtttcttagacgtcaggtggcacttttcggggaaatgt
gcgcggaacccctatttgtttatttttctaaatacattcaaatatgtatcc
gctcatgagacaataaccctgataaatgcttcaataatattgaaaaaggaa
gagtcatATGGCAATCCGAATCTTCGCGATACTTTTCTCCATTTTTTCTCT
TGCCACTTTCGCGCATGCGCAAGAAGGCACGCTAGAACGTTCTGACTGGAG
GAAGTTTTTCAGCGAATTTCAAGCCAAAGGCACGATAGTTGTGGCAGACGA
ACGCCAAGCGGATCGTGCCATGTTGGTTTTTGATCCTGTGCGATCGAAGAA
ACGCTACTCGCCTGCATCGACATTCAAGATACCTCATACACTTTTTGCACT
TGATGCAGGCGCTGTTCGTGATGAGTTCCAGATTTTTCGATGGGACGGCGT
TAACAGGGGCTTTGCAGGCCACAATCAAGACCAAGATTTGCGATCAGCAAT
GCGGAATTCTACTGTTTGGGTGTATGAGCTATTTGCAAAGGAAATTGGTGA
TGACAAAGCTCGGCGCTATTTGAAGAAAATCGACTATGGCAACGCCGGTCC -continued TTCGACAAGTAATGGCGATTACTGGATAGAAGGCAGCCTTGCAATCTCGGC
GCAGGAGCAAATTGCATTTCTCAGGAAGCTCTATCGTAACGAGCTGCCCTT
TCGGGTAGAACATCAGCGCTTGGTCAAGGATCTCATGATTGTGGAAGCCGG
TCGCAACTGGATACTGCGTGCAAAGACGGGCTGGGAAGGCCGTATGGGTTG
GTGGGTAGGATGGGTTGAGTGGCCGACTGGCTCCGTATTCTTCGCACTGAA
TATTGATACGCCAAACAGAATGGATGATCTTTTCAAGAGGGAGGCAATCGT
GCGGGCAATCCTTCGCTCTATTGAAGCGTTACCGCCCAACCCGGCAGTCAA
CTCGGACGCTGCGCGATAAggatccctgtcagaccaagtttactcatatat
actttagattgatttaaaacttcatttttaatttaaaaggatctaggtgaa
gatcctttttgataatctcatgaccaaaatcccttaacgtgagttttcgtt
ccactgagcgtcagaccccgtagaaaagatcaaaggatcttcttgagatcc
tttttttctgcgcgtaatctgctgcttgcaaacaaaaaaaccaccgctacc
agcggtggtttgtttgccggatcaagagctaccaactctttttccgaaggt
aactggcttcagcagagcgcagataccaaatactgtccttctagtgtagcc
gtagttaggccaccacttcaagaactctgtagcaccgcctacatacctcgc
tctgctaatcctgttaccagtggctgctgccagtggcgataagtcgtgtct
taccgggttggactcaagacgatagttaccggataaggcgcagcggtcggg
ctgaacggggggttcgtgcacacagcccagcttggagcgaacgacctacac
cgaactgagatacctacagcgtgagctatgagaaagcgccacgcttcccga
agggagaaaggcggacaggtatccggtaagcggcagggtcggaacaggaga
gcgcacgagggagcttccagggggaaacgcctggtatctttatagtcctgt
cgggtttcgccacctctgacttgagcgtcgatttttgtgatgctcgtcagg
ggggcggagcctatggaaaaacgccagcaacgcggcctttttacggttcct
ggccttttgctggccttttgctcacatgttctttcctgcgttatcccctga
ttctgtggataaccgtattaccgcctttgagtgagctgataccgctcgccg
cagccgaacgaccgagcgcagcgagtcagtgagcgaggaagcggaagagcg
cctgatgcggtattttctccttacgcatctgtgcggtatttcacaccgcat
ttggtgcactcicagtacaatctgctctgatgccgcatagttaagccagta
tacactccgctatcgctacgtgactgggtcatggctgcgccccgacacccg
ccaacacccgctgacgcgccctgacgggcttgtctgctcccggcatccgct
tacagacaagctgtgaccgtctccgggagctgcatgtgtcagaggttttca
ccgtcatcaccgaaacgcgcgaggcagctgcggtaaagctcatcagcgtgg
tcgtgaagcgattcacagatgtctgcctgttcatccgcgtccagctcgttg
agtttctccagaagcgttaatgtctggcttctgataaagcgggccatgtta
agggcggtttttcctgtttggtcactgatgcctccgtgtaagggggattt
ctgttcatgggggtaatgataccgatgaaacgagagaggatgctcacgata
cgggttactgatgatgaacatgcccggttactggaacgttgtgagggtaaa
caactggcggtatggatgcggcgggaccagagaaaaatcactcagggtcaa
tgccagcgcttcgttaatacagatgtaggtgttccacagggtagccagcag
catcctgcgatgcagatccggaacataatggtgcagggcgctgacttccgc
gtttccagactttacgaaacacggaaaccgaagaccattcatgttgttgct -continued caggtcgcagacgttttgcagcagcagtcgcttcacgttcgctcgcgtatc
ggtgattcattctgctaaccagtaaggcaaccccgccagcctagccgggtc
ctcaacgacaggagcacgatcatgcgcacccgtggccaggacccaacgctg
cccgagatgcgccgcgtgcggctgctggagatggcggacgcgatggatatg
ttctgccaagggttggtttgcgcattcacagttctccgcaagaattgattg
gctccaattcttggagtggtgaatccgttagcgaggtgccgccggcttcca
ttcaggtcgaggtggcccggctccatgcaccgcgacgcaacgcggggaggc
agacaaggtatagggcggcgcctacaatccatgccaacccgttccatgtgc
tcgccgaggcggcataaatcgccgtgacgatcagcggtccagtgatcgaag
ttaggctggtaagagccgcgagcgatccttgaagctgtccctgatggtcgt
catctacctgcctggacagcatggcctgcaacgcgggcatcccgatgccgc
cggaagcgagaagaatcataatggggaaggccatccagcctcgcgtcgcga
acgccagcaagacgtagcccagcgcgtcggccgccatgccggcgataatgg
cctgcttctcgccgaaacgtttggtggcgggaccagtgacgaaggcttgag
cgagggcgtgcaagattccgaataccgcaagcgacaggccgatcatcgtcg
cgctccagcgaaagcggtcctcgccgaaaatgacccagagcgctgccggca
cctgtcctacgagttgcatgataaagaagacagtcataagtgcggcgacga
tagtcatgccccgcgcccaccggaaggagctgactgggttgaaggctctca
agggcatcggtcgacgctctcccttatgcgactcctgcattaggaagcagc
ccagtagtaggttgaggccgttgagcaccgccgccgcaaggaatggtgcat
gcaaggagatggcgcccaacagtcccccggccacggggcctgccaccatac
ccacgccgaaacaagcgctcatgagcccgaagtggcgagcccgatcttccc
catcggtgatgtcggcgatataggcgccagcaaccgcacctgtggcgccgg
tgatgccggccacgatgcgtccggcgtagaggattcacaggacgggtgtgg
tcgccatgatcgcgtagtcgatagtggctccaagtagcgaagcgagcagga
ctgggcggcggccaaagcggtcggacagtgctccgagaacgggtgcgcata
gaaattgcatcaacgcatatagcgctagcagcacgccatagtgactggcga
tgctgtcggaatggacgatatcccgcaagaggcccggcagtaccggcataa
ccaagcctatgcctacagcatccagggtgacggtgccgaggatgacgatga
gcgcattgttagatttcatacacggtgcctgactgcgttagcaatttaact
gtgataaactaccgcattaaagcttatcgatgataagctgtcaaacatgag
aa pBR-CBST-KPC-4

SEQ ID 11 ttcttgaagacgaaagggcctcgtgatacgcctatttttataggttaatgt
catgataataatggtttcttagacgtcaggtggcacttttcggggaaatgt
gcgcggaacccctatttgtttatttttctaaatacattcaaatatgtatcc
gctcatgagacaataaccctgataaatgcttcaataatattgaaaaaggaa
gagtcatATGTCACTGTATCGCCGTCTAGTTCTGCTGTCTTGTCTCTCATG
GCCGCTGGCTGGCTTTTCTGCCACCGCGCTGACCAACCTCGTCGCGGAACC
ATTCGCTAAACTCGAACAGGACTTTGGCGGCTCCATCGGTGTGTACGCGAT -continued GGATACCGGCTCAGGCGCAACTGTAAGTTACCGCGCTGAGGAGCGCTTCCC
ACTGTGCAGCTCATTCAAGGGCTTTCTTGCTGCCGCTGTGCTGGCTCGCAG
CCAGCAGCAGGCCGGCTTGCTGGACACACCCATCCGTTACGGCAAAAATGC
GCTGGTTCGGTGGTCACCCATCTCGGAAAAATATCTGACAACAGGCATGAC
GGTGGCGGAGCTGTCCGCGGCCGCCGTGCAATACAGTGATAACGCCGCCGC
CAATTTGTTGCTGAAGGAGTTGGGCGGCCCGGCCGGGCTGACGGCCTTCAT
GCGCTCTATCGGCGATACCACGTTCCGTCTGGACCGCTGGGAGCTGGAGCT
GAACTCCGCCATCCCAGGCGATGCGCGCGATACCTCATCGCCGCGCGCCGT
GACGGAAAGCTTACAAAAACTGACACTGGGCTCTGCACTGGCTGCGCCGCA
GCGGCAGCAGTTTGTTGATTGGCTAAAGGGAAACACGACCGGCAACCACCG
CATCCGCGCGGCGGTGCCGGCAGACTGGGCAGTCGGAGACAAAACCGGAAC
CTGCGGAGGGTATGGCACGGCAAATGACTATGCCGTCGTCTGGCCCACTGG
GCGCGCACCTATTGTGTTGGCCGTCTACACCCGGGCGCCTAACAAGGATGA
CAAGCACAGCGAGGCCGTCATCGCCGCTGCGGCTAGACTCGCGCTCGAGGG
ATTGGGCGTCAACGGGCAGTAAggatccctgtcagaccaagtttactcata
tatactttagattgatttaaaacttcatttttaatttaaaaggatctaggt
gaagatcctttttgataatctcatgaccaaaatcccttaacgtgagttttc
gttccactgagcgtcagaccccgtagaaaagatcaaaggatcttcttgaga
tcctttttttctgcgcgtaatctgctgcttgcaaacaaaaaaaccaccgct
accagcggtggtttgtttgccggatcaagagctaccaactctttttccgaa
ggtaactggcttcagcagagcgcagataccaaatactgtccttctagtgta
gccgtagttaggccaccacttcaagaactctgtagcaccgcctacatacct
cgctctgctaatcctgttaccagtggctgctgccagtggcgataagtcgtg
tcttaccgggttggactcaagacgatagttaccggataaggcgcagcggtc
gggctgaacggggggttcgtgcacacagcccagcttggagcgaacgaccta
caccgaactgagatacctacagcgtgagctatgagaaagcgccacgcttcc
cgaagggagaaaggcggacaggtatccggtaagcggcagggtcggaacagg
agagcgcacgagggagcttccagggggaaacgcctggtatctttatagtcc
tgtcgggtttcgccacctctgacttgagcgtcgatttttgtgatgctcgtc
aggggggcggagcctatggaaaaacgccagcaacgcggcctttttacggtt
cctggccttttgctggccttttgctcacatgttctttcctgcgttatcccc
tgattctgtggataaccgtattaccgcctttgagtgagctgataccgctcg
ccgcagccgaacgaccgagcgcagcgagtcagtgagcgaggaagcggaaga
gcgcctgatgcggtattttctccttacgcatctgtgcggtatttcacaccg
catttggtgcactctcagtacaatctgctctgatgccgcatagttaagcca
gtatacactccgctatcgctacgtgactgggtcatggctgcgccccgacac
ccgccaacacccgctgacgcgccctgacgggcttgtctgctcccggcatcc
gcttacagacaagctgtgaccgtctccgggagctgcatgtgtcagaggttt
tcaccgtcatcaccgaaacgcgcgaggcagctgcggtaaagctcatcagcg
tggtcgtgaagcgattcacagatgtctgcctgttcatccgcgtccagctcg
ttgagtttctccagaagcgttaatgtctggcttctgataaagcgggccatg -continued ttaagggcggtttttttcctgtttggtcactgatgcctccgtgtaaggggga
tttctgttcatgggggtaatgataccgatgaaacgagagaggatgctcacg
atacgggttactgatgatgaacatgcccggttactggaacgttgtgagggt
aaacaactggcggtatggatgcggcgggaccagagaaaaatcactcagggt
caatgccagcgcttcgttaatacagatgtaggtgttccacagggtagccag
cagcatcctgcgatgcagatccggaacataatggtgcagggcgctgacttc
cgcgtttccagactttacgaaacacggaaaccgaagaccattcatgttgtt
gctcaggtcgcagacgttttgcagcagcagtcgcttcacgttcgctcgcgt
atcggtgattcattctgctaaccagtaaggcaaccccgccagcctagccgg
gtcctcaacgacaggagcacgatcatgcgcacccgtggccaggacccaacg
ctgcccgagatgcgccgcgtgcggctgctggagatggcggacgcgatggat
atgttctgccaagggttggtttgcgcattcacagttctccgcaagaattga
ttggctccaattcttggagtggtgaatccgttagcgaggtgccgccggctt
ccat*tcaggtcgaggtggcccggctccatgcaccgcgacgcaacgcgggga*
*ggcagacaaggtatagggcggcgcctacaatccatgccaacccgttccatg*
*tgctcgccgaggcggcataaatcgccgtgacgatcagcggtccagtgatcg*
*aagttaggctggtaagagccgcgagcgatccttgaagctgtccctgatggt*
*cgtcatctacctgcctggacagcatggcctgcaacgcgggcatcccgatgc*
*cgccggaagcgagaagaatcataatggggaaggccatccagcctcgcgtcg*
*cgaacgccagcaagacgtagcccagcgcgtcggccgccatgccggcgataa*
*tggcctgcttctcgccgaaacgtttggtggcgggaccagtgacgaaggctt*
*gagcgagggcgtgcaagattccgaataccgcaagcgacaggccgatcatcg*
*tcgcgctccagcgaaagcggtcctcgccgaaaatgacccagagcgctgccg*
*gcacctgtcctacgagttgcatgataaagaagacagtcataagtgcggcga*
*cgatagtcatgccccgcgcccaccggaaggagctgactgggttgaaggctc*
*tcaagggcatcggtcgacgctctcccttatgcgactcctgcattaggaagc*
*agcccagtagtaggttgaggccgttgagcaccgccgccgcaaggaatggtg*
*catgcaaggagatggcgcccaacagtcccccggccacggggcctgccacca*
*tacccacgccgaaacaagcgctcatgagcccgaagtggcgagcccgatctt*
*ccccatcggtgatgtcggcgatataggcgccagcaaccgcacctgtggcgc*
*cggtgatgccggccacgatgcgtccggcgtagaggattcacaggacgggtg*
*tggtcgccatgatcgcgtagtcgatagtggctccaagtagcgaagcgagca*
*ggactgggcggcggccaaagcggtcggacagtgctccgagaacgggtgcgc*
*atagaaattgcatcaacgcatatagcgctagcagcacgccatagtgactgg*
*cgatgctgtcggaatggacgatatcccgcaagaggcccggcagtaccggca*
*taaccaagcctatgcctacagcatccagggtgacggtgccgaggatgacga*
*tgagcgcattgttagatttcatacacggtgcctgactgcgttagcaattta*
actgtgataaactaccgcattaaagcttatcgatgataagctgtcaaacat
gagaa -continued pBR-CBST-DHA-1

SEQ ID 12 ttcttgaagacgaaagggcctcgtgatacgcctatttttataggttaatgt
catgataataatggtttcttagacgtcaggtggcacttttcggggaaatgt
gcgcggaacccctatttgtttatttttctaaatacattcaaatatgtatcc
gctcatgagacaataaccctgataaatgcttcaataatattgaaaaaggaa
gagtcatATGAAAAAATCGTTATCTGCAACACTGATTTCCGCTCTGCTGGC
GTTTTCCGCCCCGGGGTTTTCTGCCGCTGATAATGTCGCGGCGGTGGTGGA
CAGCACCATTAAACCGCTGATGGCACAGCAGGATATTCCCGGGATGGCGGT
TGCCGTCTCCGTAAAGGGTAAGCCCTATTATTTCAATTATGGTTTTGCCGA
TATTCAGGCAAAACAGCCGGTCACTGAAAATACACTATTTGAGCTCGGATC
TGTAAGTAAAACTTTCACAGGTGTGCTGGGTGCGGTTTCTGTGGCGAAAAA
AGAGATGGCGCTGAATGATCCGGCGGCAAAATACCAGCCGGAGCTGGCTCT
GCCGCAGTGGAAGGGGATCACATTGCTGGATCTGGCTACCTATACCGCAGG
CGGACTGCCGTTACAGGTGCCGGATGCGGTAAAAAGCCGTGCGGATCTGCT
GAATTTCTATCAGCAGTGGCAGCCGTCCCGGAAACCGGGCGATATGCGTCT
GTATGCAAACAGCAGTATCGGCCTGTTTGGTGCTCTGACCGCAAACGCGGC
GGGGATGCCGTATGAGCAGTTGCTGACTGCACGCATCCTGGCACCGCTGGG
GTTATCTCACACCTTTATTACTGTGCCGGAAAGTGCGCAAAGCCAGTATGC
GTACGGTTATAAAAACAAAAAACCGGTCCGCGTGTCGCCGGGACAGCTTGA
TGCGGAATCTTACGGCGTGAAATCCGCCTCAAAAGATATGCTGCGCTGGGC
GGAAATGAATATGGAGCCGTCACGGGCCGGTAATGCGGATCTGGAAATGGC
AATGTATCTCGCCCAGACCCGCTACTATAAAACCGCCGCGATTAACCAGGG
GCTGGGCTGGGAAATGTATGACTGGCCGCAGCAGAAAGATATGATCATTAA
CGGTGTGACCAACGAGGTCGCATTGCAGCCGCATCCGGTAACAGACAACCA
GGTTCAGCCGTATAACCGTGCTTCCTGGGTGCATAAAACGGGCGCAACAAC
TGGTTTCGGCGCCTATGTCGCCTTTATTCCGGAAAAACAGGTGGCGATTGT
GATTCTGGCGAATAAAAACTACCCGAATACCGAAAGAGTCAAAGCTGCACA
GGCTATTTTGAGTGCACTGGAATAAggatccctgtcagaccaagtttactc
atatatactttagattgatttaaaacttcatttttaatttaaaaggatcta
ggtgaagatcctttttgataatctcatgaccaaaatcccttaacgtgagtt
ttcgttccactgagcgtcagaccccgtagaaaagatcaaaggatcttcttg
agatcctttttttctgcgcgtaatctgctgcttgcaaacaaaaaaaccacc
gctaccagcggtggtttgtttgccggatcaagagctaccaactctttttcc
gaaggtaactggcttcagcagagcgcagataccaaatactgtccttctagt
gtagccgtagttaggccaccacttcaagaactctgtagcaccgcctacata
cctcgctctgctaatcctgttaccagtggctgctgccagtggcgataagtc
gtgtcttaccgggttggactcaagacgatagttaccggataaggcgcagcg
gtcgggctgaacggggggttcgtgcacacagcccagcttggagcgaacgac
ctacaccgaactgagatacctacagcgtgagctatgagaaagcgccacgct
tcccgaagggagaaaggcggacaggtatccggtaagcggcagggtcggaac
aggagagcgcacgagggagcttccagggggaaacgcctggtatctttatag
tcctgtcgggtttcgccacctctgacttgagcgtcgatttttgtgatgctc
gtcaggggggcggagcctatggaaaaacgccagcaacgcggcctttttacg
gttcctggccttttgctggccttttgctcacatgttctttcctgcgttatc
ccctgattctgtggataaccgtattaccgcctttgagtgagctgataccgc
tcgccgcagccgaacgaccgagcgcagcgagtcagtgagcgaggaagcgga
agagcgcctgatgcggtattttctccttacgcatctgtgcggtatttcaca
ccgcatttggtgcactctcagtacaatctgctctgatgccgcatagttaag
ccagtatacactccgctatcgctacgtgactgggtcatggctgcgccccga
cacccgccaacacccgctgacgcgccctgacgggcttgtctgctcccggca
tccgcttacagacaagctgtgaccgtctccgggagctgcatgtgtcagagg
ttttcaccgtcatcaccgaaacgcgcgaggcagctgcggtaaagctcatca
gcgtggtcgtgaagcgattcacagatgtctgcctgttcatccgcgtccagc
tcgttgagtttctccagaagcgttaatgtctggcttctgataaagcgggcc
atgttaagggcggtttttttcctgtttggtcactgatgcctccgtgtaaggg
ggatttctgttcatgggggtaatgataccgatgaaacgagagaggatgctc
acgatacgggttactgatgatgaacatgcccggttactggaacgttgtgag
ggtaaacaactggcggtatggatgcggcgggaccagagaaaaatcactcag
ggtcaatgccagcgcttcgttaatacagatgtaggtgttccacagggtagc
cagcagcatcctgcgatgcagatccggaacataatggtgcagggcgctgac
ttccgcgtttccagactttacgaaacacggaaaccgaagaccattcatgtt
gttgctcaggtcgcagacgttttgcagcagcagtcgcttcacgttcgctcg
cgtatcggtgattcattctgctaaccagtaaggcaaccccgccagcctagc
cgggtcctcaacgacaggagcacgatcatgcgcacccgtggccaggaccca
acgctgcccgagatgcgccgcgtgcggctgctggagatggcggacgcgatg
gatatgttctgccaagggttggtttgcgcattcacagttctccgcaagaat
tgattggctccaattcttggagtggtgaatccgttagcgaggtgccgccgg
cttccatt*caggtcgaggtggcccggctccatgcaccgcgacgcaacgcgg*
*ggaggcagacaaggtatagggcggcgcctacaatccatgccaacccgttcc*
*atgtgctcgccgaggcggcataaatcgccgtgacgatcagcggtccagtga*
*tcgaagttaggctggtaagagccgcgagcgatccttgaagctgtccctgat*
*ggtcgtcatctacctgcctggacagcatggcctgcaacgcgggcatcccga*
*tgccgccggaagcgagaagaatcataatggggaaggccatccagcctcgcg*
*tcgcgaacgccagcaagacgtagcccagcgcgtcggccgccatgccggcga*
*taatggcctgcttctcgccgaaacgtttggtggcgggaccagtgacgaagg*
*cttgagcgagggcgtgcaagattccgaataccgcaagcgacaggccgatca*
*tcgtcgcgctccagcgaaagcggtcctcgccgaaaatgacccagagcgctg*
*ccggpacctgtcctacgagttgcatgataaagaagacagtcataagtgcgg*
*cgacgatagtcatgccccgcgcccaccggaaggagctgactgggttgaagg*
*ctctcaagggcatcggtcgacgctctcccttatgcgactcctgcattagga*
*agcagcccagtagtaggttgaggccgttgagcaccgccgccgcaaggaatg*

-continued gtgcatgcaaggagatggcgcccaacagtcccccggccacggggcctgcca
ccatacccacgccgaaacaagcgctcatgagcccgaagtggcgagcccgat
cttccccatcggtgatgtcggcgatataggcgccagcaaccgcacctgtgg
cgccggtgatgccggccacgatgcgtccggcgtagaggattcacaggacgg
gtgtggtcgccatgatcgcgtagtcgatagtggctccaagtagcgaagcga
gcaggactgggcggcggccaaagcggtcggacagtgctccgagaacgggtg
cgcatagaaattgcatcaacgcatatagcgctagcagcacgccatagtgac
tggcgatgctgtcggaatggacgatatcccgcaagaggcccggcagtaccg
gcataaccaagcctatgcctacagcatccagggtgacggtgccgaggatga
cgatgagcgcattgttagatttcatacacggtgcctgactgcgttagcaat
ttaactgtgataaactaccgcattaaagcttatcgatgataagctgtcaaa
catgagaa pBR-CBST-ADC-33

SEQ ID 13 ttcttgaagacgaaagggcctcgtgatacgcctatttttataggttaatgt
catgataataatggtttcttagacgtcaggtggcacttttcggggaaatgt
gcgcggaacccctatttgtttatttttctaaatacattcaaatatgtatcc
gctcatgagacaataaccctgataaatgcttcaataatattgaaaaaggaa
gagtcatATGCGATTTAAAAAAATTTCTTGTCTACTTTTATCCCCGCTTTT
TATTTTTAGTACCTCAATTTATGCGGGCAATACACCAAAAGACCAAGAAAT
TAAAAAACTGGTAGATCAAAACTTTAAACCGTTATTAGAAAAATATGATGT
GCCAGGTATGGCTGTGGGTGTTATTCAAAATAATAAAAAGTATGAAATGTA
TTATGGTCTTCAATCTGTTCAAGATAAAAAAGCCGTAAATAGCAGTACCAT
TTTTGAGCTAGGTTCTGTCAGTAAATTATTTACCGCGACAGCAGGTGGATA
TGCAAAAAATAAAGGAAAAATCTCTTTTGACGATACGCCTGGTAAATATTG
GAAAGAACTAAAAAACACACCGATTGACCAAGTTAACTTACTTCAACTCGC
GACGTATACAAGTGGTAACCTTGCCTTGCAGTTTCCAGATGAAGTAAAAAC
AGACCAACAAGTTTTAACTTTTTTCAAAGACTGGAAACCTAAAAACTCAAT
CGGTGAATACAGACAATATTCAAATCCAAGTATTGGCCTATTTGGAAAGGT
TGTGGCTTTGTCTATGAATAAACCTTTCGACCAAGTCTTAGAAAAAACAAT
TTTTCCGGCCCTTGGCTTAAAACATAGCTATGTAAATGTACCTAAGACCCA
GATGCAAAACTATGCATTTGGTTATAACCAAGAAAATCAGCCGATTCGAGT
TAACCGCGGCCCACTCGATGCCGCCCCTGCGTATGGCGTCAAATCGACACT
ACCCGACATGTTGAGTTTTATTCATGCCAACCTTAACCCACAGAAATATCC
GGCTGATATTCAACGGGCAATTAATGAAACACATCAAGGGCGCTATCAAGT
AAATACCATGTATCAGGCACTCGGTTGGGAAGAGTTTTCTTATCCGGCAAC
GTTACAAACTTTATTAGACAGTAATTCAGAACAGATTGTGATGAAACCTAA
TAAAGTGACTGCTATTTCAAAGGAACCTTCAGTTAAGATGTACCATAAAAC
TGGCTCAACCAACGGTTTCGGAACGTATGTAGTGTTTATTCCTAAAGAAAA
TATTGGCTTAGTCATGTTAACCAATAAACGTATTCCAAATGAAGAGCGCAT
TAAGGCAGCTTATGCTGTGCTGAATGCAATAAAGAAATAAggatccctgtc -continued agaccaagtttactcatatatactttagattgatttaaaacttcatttttta
atttaaaaggatctaggtgaagatcctttttgataatctcatgaccaaaat
cccttaacgtgagttttcgttccactgagcgtcagaccccgtagaaaagat
caaaggatcttcttgagatcctttttttctgcgcgtaatctgctgcttgca
aacaaaaaaaccaccgctaccagcggtggtttgtttgccggatcaagagct
accaactctttttccgaaggtaactggcttcagcagagcgcagataccaaa
tactgtccttctagtgtagccgtagttaggccaccacttcaagaactctgt
agcaccgcctacatacctcgctctgctaatcctgttaccagtggctgctgc
cagtggcgataagtcgtgtcttaccgggttggactcaagacgatagttacc
ggataaggcgcagcggtcgggctgaacggggggttcgtgcacacagcccag
cttggagcgaacgacciacaccgaactgagatacctacagcgtgagctatg
agaaagcgccacgcttcccgaagggagaaaggcggacaggtatccggtaag
cggcagggtcggaacaggagagcgcacgagggagcttccaggggggaaacgc
ctggtatctttatagtcctgtcgggtttcgccacctctgacttgagcgtcg
atttttgtgatgctcgtcaggggggcggagcctatggaaaaacgccagcaa
cgcggcctttttacggttcctggccttttgctggccttttgctcacatgtt
ctttcctgcgttatcccctgattctgtggataaccgtattaccgcctttga
gtgagctgataccgctcgccgcagccgaacgaccgagcgcagcgagtcagt
gagcgaggaagcggaagagcgcctgatgcggtattttctccttacgcatct
gtgcggtatttcacaccgcatttggtgcactctcagtacaatctgctctga
tgccgcatagttaagccagtatacactccgctatcgctacgtgactgggtc
atggctgcgccccgacacccgccaacacccgctgacgcgccctgacgggct
tgtctgctcccggcatccgcttacagacaagctgtgaccgtctccgggagc
tgcatgtgtcagaggttttcaccgtcatcaccgaaacgcgcgaggcagctg
cggtaaagctcatcagcgtggtcgtgaagcgattcacagatgtctgcctgt
tcatccgcgtccagctcgttgagtttctccagaagcgttaatgtctggctt
ctgataaagcgggccatgttaagggcggttttttcctgtttggtcactgat
gcctccgtgtaagggggatttctgttcatgggggtaatgataccgatgaaa
cgagagaggatgctcacgatacgggttactgatgatgaacatgcccggtta
ctggaacgttgtgagggtaaacaactggcggtatggatgcggcgggaccag
agaaaaatcactcagggtcaatgccagcgcttcgttaatacagatgtaggt
gttccacagggtagccagcagcatcctgcgatgcagatccggaacataatg
gtgcagggcgctgacttccgcgtttccagactttacgaaacacggaaaccg
aagaccattcatgttgttgctcaggtcgcagacgttttgcagcagcagtcg
cttcacgttcgctcgcgtatcggtgattcattctgctaaccagtaaggcaa
ccccgccagcctagccgggtcctcaacgacaggagcacgatcatgcgcacc
cgtggccaggacccaacgctgcccgagatgcgccgcgtgcggctgctggag
atggcggacgcgatggatatgttctgccaagggttggtttgcgcattcaca
gttctccgcaagaattgattggctccaattcttggagtggtgaatccgtta
gcgaggtgccgccggcttccattcaggtcgaggtggcccggctccatgcac
cgcgacgcaacgcggggaggcagacaaggtatagggcggcgcctacaatcc -continued

```
atgccaacccgttccatgtgctcgccgaggcggcataaatcgccgtgacga
tcagcggtccagtgatcgaagttaggctggtaagagccgcgagcgatcctt
gaagctgtccctgatggtcgtcatctacctgcctggacagcatggcctgca
acgcgggcatcccgatgccgccggaagcgagaagaatcataatggggaagg
ccatccagcctcgcgtcgcgaacgccagcaagacgtagcccagcgcgtcgg
ccgccatgccggcgataatggcctgcttctcgccgaaacgtttggtggcgg
gaccagtgacgaaggcttgagcgagggcgtgcaagattccgaataccgcaa
gcgacaggccgatcatcgtcgcgctccagcgaaagcggtcctcgccgaaaa
tgacccagagcgctgccggcacctgtcctacgagttgcatgataaagaaga
cagtcataagtgcggcgacgatagtcatgccccgcgcccaccggaaggagc
tgactgggttgaaggctctcaagggcatcggtcgacgctctcccttatgcg
actcctgcattaggaagcagcccagtagtaggttgaggccgttgagcaccg
ccgccgcaaggaatggtgcatgcaaggagatggcgcccaacagtcccccgg
ccacggggcctgccaccatacccacgccgaaacaagcgctcatgagcccga
agtggcgagcccgatcttccccatcggtgatgtcggcgatataggcgccag
caaccgcacctgtggcgccggtgatgccggccacgatgcgtccggcgtaga
ggattcacaggacgggtgtggtcgccatgatcgcgtagtcgatagtggctc
caagtagcgaagcgagcaggactgggcggcggccaaagcggtcggacagtg
ctccgagaacgggtgcgcatagaaattgcatcaacgcatatagcgctagca
gcacgccatagtgactggcgatgctgtcggaatggacgatatcccgcaaga
ggcccggcagtaccggcataaccaagcctatgcctacagcatccagggtga
cggtgccgaggatgacgatgagcgcattgttagatttcatacacggtgcct
gactgcgttagcaatttaactgtgataaactaccgcattaaagcttatcga
tgataagctgtcaaacatgagaa
```

Example 12

Standard BLI Potentiation MIC Assay

The ability of compounds to potentiate the activity of β-lactams was demonstrated by determining the minimum inhibitory concentrations (MIC) of β-lactam and BLI compound combinations against various β-lactamase producing bacterial strains using the broth microdilution method. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition").

To prepare for MIC testing, frozen glycerol stocks of clinical isolates (*Klebsiella pneumoniae, Eschericia coli, Enterobacter* spp, *Citrobacter* spp, or *Pseudomonas aeruginosa*) were used to streak for isolated colonies on rich, non-selective, tryptic soy agar containing 5% sheep's blood (TSAB). Frozen glycerol stocks of laboratory engineered, isogenic *E. coli* strains, which contain cloned β-lactamase expressing plasmids were used to streak for isolated colonies on rich, selective LB agar supplemented with 25 μg/mL tetracycline to maintain the plasmid. All strains were incubated at 37° C. for 18-24 hrs.

On the day of testing, primary cultures were started by scraping off 5-10 colonies from the TSAB plates containing clinical strains or the tetracycline supplemented LB plates containing engineered strains. The clinical strain material was suspended in ~5 mL of cation adjusted Mueller Hinton Broth (CAMHB) in 14 mL culture tubes. The engineered strain material was suspended in CAMHB (supplemented with 25 ug/mL tetracycline) in 14 mL culture tubes. All strains were incubated at 37° C. with aeration (200 rpm) for ~2 hrs until the optical density at 600 nm (OD 600) was ≥0.1.

The two compound components of the assay were each diluted in CAMHB and added to the 96-well broth microdilution assay plates. 50 μL of the β-lactam was added to each well of the assay plate in 2-fold dilutions with final concentrations ranging from 128-0.13 μg/mL. 25 μL of the BLI compound was added to all wells in the broth microdilution plates at a final concentration of 4 μg/mL. Inoculum cultures were prepared by standardizing the primary cultures to OD600=0.1 and then adding 20 μL of the adjusted primary culture per 1 mL CAMHB for clinical strains or CAMHB (supplemented with tetracycline at 100 μg/mL) for engineered strains, so that the final inoculum density was ~$10^5$ colony forming units per milliliter. Diluted inoculum cultures were used to inoculate 25 μL per well in 96-well broth microdilution assay plates. The final volume of each well was 100 μL and contained a β-lactam at different concentrations, a BLI compound at 4 μg/mL concentration, the bacterial culture at an OD600 of approximately 0.001 and when necessary tetracycline at 25 μg/mL.

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. MIC values were defined as the lowest concentration producing no visible turbidity.

MIC values of representative compounds are shown in Table II.

Example 13

Synergy MIC (sMIC) Assay

The synergy MIC (sMIC) assay determines the concentration of the BLI required to potentiate the activity of a fixed concentration of a β-lactam antibiotic against β-lactamase producing bacterial strains. The experimental protocol was performed according to Clinical and Laboratory Standards Institute (CLSI) guidelines with modifications as described below (CLSI guidelines can be derived from the CLSI document M07-A9 published in January 2012: "Methods for Dilution Antimicrobial Susceptibility Tests for Bacteria That Grow Aerobically; Approved Standard-Ninth Edition"). The assay is set-up by serially diluting the BLI across 11 of the 12 wells in each row of a 96-well broth microdilution assay plate, adding the β-lactam at a fixed concentration to all wells in the assay plate, inoculating the assay plate with bacterial strains, and determining the lowest concentration of BLI required to inhibit overnight bacterial growth. Bacterial growth in the $12^{th}$ well of the assay plate, which contains the β-lactam at a fixed concentration but does not contain any BLI, demonstrates that the bacterial strains are resistant to the β-lactam antibiotic (e.g ceftolozane) at the fixed concentration of 4 μg/mL.

To prepare for MIC testing, frozen glycerol stocks of clinical isolates (*Klebsiella pneumoniae, Eschericia coli, Enterobacter* spp, *Citrobacter* spp, or *Pseudomonas aeruginosa*) were used to streak for isolated colonies on rich, non-selective, tryptic soy agar containing 5% sheep's blood (TSAB). Frozen glycerol stocks of laboratory engineered, isogenic *E. coli* strains, which contain cloned β-lactamase expressing plasmids were used to streak for isolated colonies on rich, selective LB agar supplemented with 25 μg/mL tetracycline to maintain the plasmid. All strains were incubated at 37° C. for 18-24 hrs.

On the day of testing, primary cultures were started by scraping off 5-10 colonies from the TSAB plates containing clinical strains or the tetracycline supplemented LB plates containing engineered strains. The clinical strain material was suspended in ~5 mL of cation adjusted Mueller Hinton Broth (CAMHB) in 14 mL culture tubes. The engineered strain material was suspended in CAMHB (supplemented with tetracycline at 25 μg/mL) in 14 mL culture tubes. All strains were incubated at 37° C. with aeration (200 rpm) for ~2 hrs until the OD600 was ≥0.1.

The two compound components of the assay were each prepared in CAMHB and added to the 96-well broth microdilution assay plates. 50 μL of the BLI was added to each well of the assay plate in 2-fold dilutions with final concentrations ranging from 128 to 0.13 μg/mL. 25 μL of the β-lactam was added to all wells in the broth microdilution plates at a final concentration of 4 μg/mL. Inoculum cultures were prepared by standardizing the primary cultures to OD600=0.1 and then adding 20 μL of the adjusted primary culture per 1 mL CAMHB for clinical strains or CAMHB (supplemented with tetracycline at 100 μg/mL) for isogenic strains, so that the final inoculum density was ~$10^5$ colony forming units per milliliter. Diluted inoculum cultures were used to inoculate 25 μL per well in 96-well broth microdilution assay plates. The final volume of each well was 100 μL and contained a BLI at different concentrations, a β-lactam at 4 μg/mL concentration, the bacterial culture at an OD600 of approximately 0.001 and when necessary tetracycline at 25 ug/mL.

Interpreting the sMIC Data:

Plates were incubated for 18-20 hours at 37° C. with aeration (200 rpm). Following incubation, growth was confirmed visually placing plates over a viewing apparatus (stand with a mirror underneath) and then OD600 was measured using a SpectraMax 340PC384 plate reader (Molecular Devices, Sunnyvale, Calif.). Growth was defined as turbidity that could be detected with the naked eye or achieving minimum OD600 of 0.1. sMIC values were defined as the lowest concentration producing no visible turbidity.

The sMIC values represent the amount of BLI required to potentiate the activity of 4 μg/ml of 0CA-101 (Ceftolozane) or ceftazidime to inhibit the growth of the β-lactamase producing bacteria.

sMIC values of representative compounds are shown in Table III.

Example 14

Inhibition Kinetics

Inhibition or inactivation of KPC-2 by test inhibitors was assessed using 100 μM nitrocefin (NCF) as a reporter substrate. Assays were performed in 1×PBS pH 7.4, 0.1 mg/ml BSA, in 96-well half area plates, 50 μl reaction volume. NCF was dissolved in DMSO and diluted in assay buffer. Test inhibitors were dissolved in water or DMSO and serially diluted in the assay with final concentrations between 2000-0.195 μM.

The enzyme activity in the presence of varying concentrations of test inhibitor was determined by monitoring the hydrolysis of NCF spectrophotometrically at 486 nm, for 5 minutes, 25° C., using a SpectraMax Plus384 microplate reader with SoftMax Pro software (Molecular Devices). Data analysis was performed using GraphPad Prism (GraphPad Software, Inc.).

Progress curves were fit to a first-order rate decay equation (Eq. 1) to determine $k_{observed}$ ($k_{obs}$).

$k_{obs}$ vs. inhibitor concentration [I] curves were then fit to Eq. 2 to determine the inhibitor dissociation constant (K) and the first order rate constant of enzyme inactivation at infinite inhibitor concentration ($k_{inact}$). Table IV shows kinetics results from representative test compounds. A larger $k_{inact}$/K ratio indicates a more effective enzyme inactivator.

$$Y_t=V_0*(1-e^{(-k_{obd}*t)})/k_{obs} \quad \text{Eq. 1}$$

Where Y is the absorbance at time t, $V_0$ is the uninhibited enzyme velocity, $k_{obs}$ is the observed rate constant of the enzyme inactivation.

$$k_{obs}=k_{inact}*[I]/([I]+K(1+S/K_m)) \quad \text{Eq. 2}$$

Where S is the NCF concentration, $K_m$ is the KPC-2 $K_m$ for NCF.

We claim:

1. A compound of Formula (I) or a pharmaceutically acceptable salt thereof:

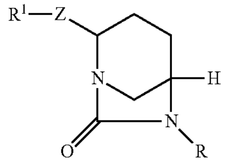

(I)

wherein

Z is selected from a 1,2,4-oxadiazole or a 1,2,4-thiadiazole;

R is selected from

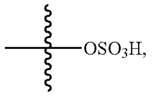

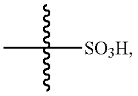

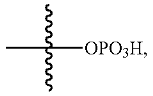

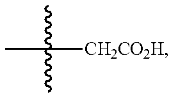

or

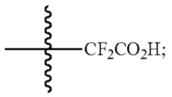

and $R^1$ is selected from:

hydrogen,

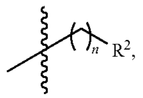

wherein $R^2$ is selected from

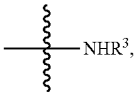

or

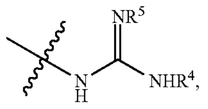

wherein each of $R^3$, $R^4$ and $R^5$ is independently selected from hydrogen, $(C_1\text{-}C_3)$-alkyl, aminoalkyl, aminocycloalkyl, or hydroxyalkyl, and n is selected from 1, 2 or 3, amino,

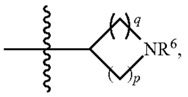

wherein $R^6$ is selected from H, $(C_1\text{-}C_3)$-unsubstituted alkyl, amino-$(C_2\text{-}C_3)$-alkyl, aminocycloalkyl, hydroxyalkyl,

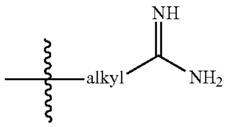

or

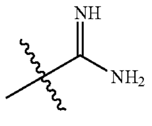

and each of p and q is independently selected from 1 or 2; and $—CH_2(R^7)CH_2NH_2$ wherein $R^7$ is selected from amino or hydroxyl.

2. The compound of claim 1 wherein Z-$R^1$ is

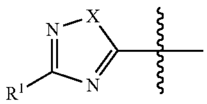

, wherein X is selected from O or S and wherein R and $R^1$ are as previously described.

3. The compound of claim 1 wherein Z-$R^1$ is

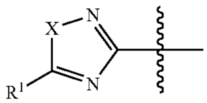

, wherein X is selected from O or S and wherein R and $R^1$ are as previously described.

4. A pharmaceutical composition comprising a compound of claim 1 and at least 1 β-lactam antibiotic or a pharmaceutically acceptable salt thereof.

5. The pharmaceutical composition of claim 4 wherein the β-lactam antibiotic is selected from the group consisting of: a cephalosporin, a carbapenem and a monobactam.

6. The pharmaceutical composition of claim 5 wherein the cephalosporin is Ceftolozane.

7. The compound of claim 1 wherein the compound of Formula (I) exhibits a binding affinity for the KPC-2 β-lactamase enzyme of at least 250 $mM^{-1}s^{-1}$.

8. A compound selected from the group consisting of Formula (III), Formula (IV), Formula (V), Formula (VI), Formula (VII) and Formula (VIII), and pharmaceutically acceptable salts thereof:

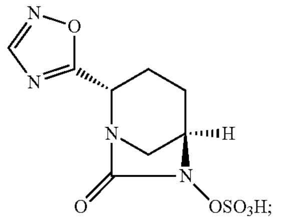

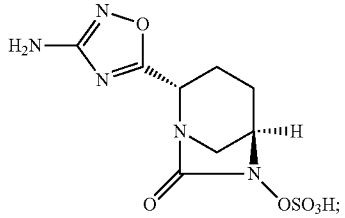

-continued

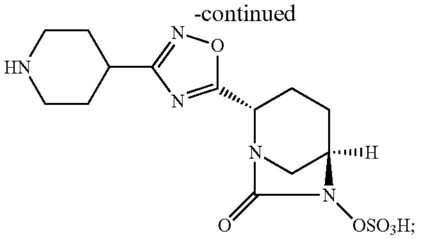

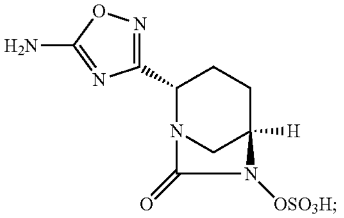

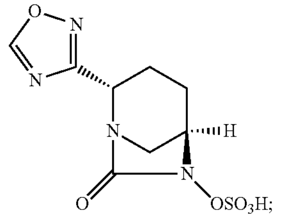

and

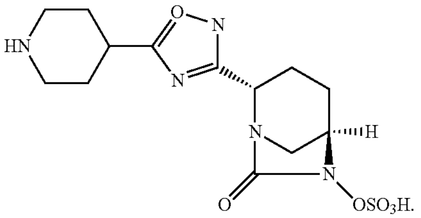

9. A pharmaceutical composition comprising a compound of claim 1 and a cephalosporin antibiotic.

10. The pharmaceutical composition of claim 9, wherein the cephalosporin antibiotic is selected from the group consisting of: Cefacetrile, Cefadroxil, Cefalexin, Cefaloglycin, Cefalonium, Cefaloridine, Cefalotin, Cefapirin, Cefatrizine, Cefazaflur, Cefazedone, Cefazolin, Cefradine, Cefroxadine, Ceftezole, Cefaclor, Cefamandole, Cefmetazole, Cefonicid, Cefotetan, Cefoxitin, Cefprozil, Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef, and Ceftolozane.

11. A pharmaceutical composition comprising a compound of claim 1 and a carbapenem antibiotic.

12. The pharmaceutical composition of claim 11, wherein the carbapenem antibiotic is selected from the group consisting of: Imipenem, Impenem/Cilastatin, Biapenem, Doripenem, Meropenem, Ertapenem, and Paripenem.

13. A pharmaceutical composition comprising a compound of claim 1 and a monobactam antibiotic.

14. The pharmaceutical composition of claim 13, wherein the monobactam antibiotic is selected from the group consisting of: Aztreonam, Tigemonam, Carumonam, BAL30072, and Nocardicin A.

15. A pharmaceutical composition comprising a compound of claim 7 and a cephalosporin antibiotic.

16. The pharmaceutical composition of claim 15, wherein the cephalosporin antibiotic is selected from the group consisting of: Cefacetrile, Cefadroxil, Cefalexin, Cefaloglycin, Cefalonium, Cefaloridine, Cefalotin, Cefapirin, Cefatrizine, Cefazaflur, Cefazedone, Cefazolin, Cefradine, Cefroxadine, Ceftezole, Cefaclor, Cefamandole, Cefmetazole, Cefonicid, Cefotetan, Cefoxitin, Cefprozil, Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef, and Ceftolozane.

17. A pharmaceutical composition comprising a compound of claim 7 and a carbapenem antibiotic.

18. The pharmaceutical composition of claim 17, wherein the carbapenem antibiotic is selected from the group consisting of: Imipenem, Impenem/Cilastatin, Biapenem, Doripenem, Meropenem, Ertapenem, and Paripenem.

19. A pharmaceutical composition comprising a compound of claim 7 and a monobactam antibiotic.

20. The pharmaceutical composition of claim 19, wherein the monobactam antibiotic is selected from the group consisting of: Aztreonam, Tigemonam, Carumonam, BAL30072, and Nocardicin A.

* * * * *

SEQUENCE LISTING

```
<160> NUMBER OF SEQ ID NOS: 13

<210> SEQ ID NO 1
<211> LENGTH: 32
<212> TYPE: DNA
<213> ORGANISM: Artificial Sequence
<220> FEATURE:
<223> OTHER INFORMATION: Sythetic primer: pBR-Pbla

<400> SEQUENCE: 1

cgcatatgac tcttcctttt tcaatattat tg                               32


<210> SEQ ID NO 2
<211> LENGTH: 28
<212> TYPE: DNA
<213> ORGANISM: Artificial Sequence
<220> FEATURE:
<223> OTHER INFORMATION: Sythetic primer: pBR-vec-1
```

<400> SEQUENCE: 2
gcggatccct gtcagaccaa gtttactc 28

<210> SEQ ID NO 3
<211> LENGTH: 28
<212> TYPE: DNA
<213> ORGANISM: Artificial Sequence
<220> FEATURE:
<223> OTHER INFORMATION: Sythetic primer: Pbla-cat

<400> SEQUENCE: 3
gccatatgat ggagaaaaaa atcactgg 28

<210> SEQ ID NO 4
<211> LENGTH: 28
<212> TYPE: DNA
<213> ORGANISM: Artificial Sequence
<220> FEATURE:
<223> OTHER INFORMATION: Sythetic primer: Vec-1-cat

<400> SEQUENCE: 4
cgggatccct agagaatagg aacttcgg 28

<210> SEQ ID NO 5
<211> LENGTH: 4236
<212> TYPE: DNA
<213> ORGANISM: Artificial Sequence
<220> FEATURE:
<223> OTHER INFORMATION: Synthetic construct: pBR-CBST-cat

<400> SEQUENCE: 5
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtca tatggagaaa aaaatcactg gatataccac 240
cgttgatata tcccaatggc atcgtaaaga acattttgag gcatttcagt cagttgctca 300
atgtacctat aaccagaccg ttcagctgga tattacggcc tttttaaaga ccgtaaagaa 360
aaataagcac aagttttatc cggcctttat tcacattctt gcccgcctga tgaatgctca 420
tacggaattt cgtatggcaa tgaaagacgg tgagctggtg atatgggata gtgttcaccc 480
ttgttacacc gttttccatg agcaaactga aacgttttca tcgctctgga gtgaatacca 540
cgacgatttc cggcagtttc tacacatata ttcgcaagat gtggcgtgtt acggtgaaaa 600
cctggcctat ttccctaaag ggtttattga gaatatgttt ttcgtctcag ccaatccctg 660
ggtgagtttc accagttttg atttaaacgt ggccaatatg gacaacttct tcgcccccgt 720
tttcactatg ggcaaatatt atacgcaagg cgacaaggtg ctgatgccgc tggcgattca 780
ggttcatcat gccgtctgtg atggcttcca tgtcggcaga atgcttaatg aattacaaca 840
gtactgcgat gagtggcagg gcggggcgta agtggcaggg cggggcgtaa ggcgcgccat 900
ttaaatgaag ttcctattcc gaagttccta ttctctaggg atccctgtca gaccaagttt 960
actcatatat actttagatt gatttaaaac ttcattttta atttaaaagg atctaggtga 1020
agatcctttt tgataatctc atgaccaaaa tcccttaacg tgagttttcg ttccactgag 1080
cgtcagaccc cgtagaaaag atcaaaggat cttcttgaga tccttttttt ctgcgcgtaa 1140
tctgctgctt gcaaacaaaa aaaccaccgc taccagcggt ggtttgtttg ccggatcaag 1200

-continued

```
agctaccaac tctttttccg aaggtaactg gcttcagcag agcgcagata ccaaatactg   1260
tccttctagt gtagccgtag ttaggccacc acttcaagaa ctctgtagca ccgcctacat   1320
acctcgctct gctaatcctg ttaccagtgg ctgctgccag tggcgataag tcgtgtctta   1380
ccgggttgga ctcaagacga tagttaccgg ataaggcgca gcggtcgggc tgaacggggg   1440
gttcgtgcac acagcccagc ttggagcgaa cgacctacac cgaactgaga tacctacagc   1500
gtgagctatg agaaagcgcc acgcttcccg aagggagaaa ggcggacagg tatccggtaa   1560
gcggcagggt cggaacagga gagcgcacga gggagcttcc agggggaaac gcctggtatc   1620
tttatagtcc tgtcgggttt cgccacctct gacttgagcg tcgatttttg tgatgctcgt   1680
caggggggcg gagcctatgg aaaaacgcca gcaacgcggc ctttttacgg ttcctggcct   1740
tttgctggcc ttttgctcac atgttctttc ctgcgttatc ccctgattct gtggataacc   1800
gtattaccgc ctttgagtga gctgataccg ctcgccgcag ccgaacgacc gagcgcagcg   1860
agtcagtgag cgaggaagcg gaagagcgcc tgatgcggta ttttctcctt acgcatctgt   1920
gcggtatttc acaccgcatt tggtgcactc tcagtacaat ctgctctgat gccgcatagt   1980
taagccagta tacactccgc tatcgctacg tgactgggtc atggctgcgc cccgacaccc   2040
gccaacaccc gctgacgcgc cctgacgggc ttgtctgctc ccggcatccg cttacagaca   2100
agctgtgacc gtctccggga gctgcatgtg tcagaggttt tcaccgtcat caccgaaacg   2160
cgcgaggcag ctgcggtaaa gctcatcagc gtggtcgtga agcgattcac agatgtctgc   2220
ctgttcatcc gcgtccagct cgttgagttt ctccagaagc gttaatgtct ggcttctgat   2280
aaagcgggcc atgttaaggg cggttttttc ctgtttggtc actgatgcct ccgtgtaagg   2340
gggatttctg ttcatggggg taatgatacc gatgaaacga gagaggatgc tcacgatacg   2400
ggttactgat gatgaacatg cccggttact ggaacgttgt gagggtaaac aactggcggt   2460
atggatgcgg cgggaccaga gaaaaatcac tcagggtcaa tgccagcgct tcgttaatac   2520
agatgtaggt gttccacagg gtagccagca gcatcctgcg atgcagatcc ggaacataat   2580
ggtgcagggc gctgacttcc gcgtttccag actttacgaa acacggaaac cgaagaccat   2640
tcatgttgtt gctcaggtcg cagacgtttt gcagcagcag tcgcttcacg ttcgctcgcg   2700
tatcggtgat tcattctgct aaccagtaag gcaaccccgc cagcctagcc gggtcctcaa   2760
cgacaggagc acgatcatgc gcacccgtgg ccaggaccca acgctgcccg agatgcgccg   2820
cgtgcggctg ctggagatgg cggacgcgat ggatatgttc tgccaagggt tggtttgcgc   2880
attcacagtt ctccgcaaga attgattggc tccaattctt ggagtggtga atccgttagc   2940
gaggtgccgc cggcttccat tcaggtcgag gtggcccggc tccatgcacc gcgacgcaac   3000
gcggggaggc agacaaggta tagggcggcg cctacaatcc atgccaaccc gttccatgtg   3060
ctcgccgagg cggcataaat cgccgtgacg atcagcggtc cagtgatcga agttaggctg   3120
gtaagagccg cgagcgatcc ttgaagctgt ccctgatggt cgtcatctac ctgcctggac   3180
agcatggcct gcaacgcggg catcccgatg ccgccggaag cgagaagaat cataatgggg   3240
aaggccatcc agcctcgcgt cgcgaacgcc agcaagacgt agcccagcgc gtcggccgcc   3300
atgccggcga taatggcctg cttctcgccg aaacgtttgg tggcgggacc agtgacgaag   3360
gcttgagcga gggcgtgcaa gattccgaat accgcaagcg acaggccgat catcgtcgcg   3420
ctccagcgaa agcggtcctc gccgaaaatg acccagagcg ctgccggcac ctgtcctacg   3480
agttgcatga taaagaagac agtcataagt gcggcgacga tagtcatgcc ccgcgcccac   3540
cggaaggagc tgactgggtt gaaggctctc aagggcatcg gtcgacgctc tcccttatgc   3600
```

```
gactcctgca ttaggaagca gcccagtagt aggttgaggc cgttgagcac cgccgccgca   3660
aggaatggtg catgcaagga gatggcgccc aacagtcccc cggccacggg gcctgccacc   3720
atacccacgc cgaaacaagc gctcatgagc ccgaagtggc gagcccgatc ttccccatcg   3780
gtgatgtcgg cgatataggc gccagcaacc gcacctgtgg cgccggtgat gccggccacg   3840
atgcgtccgg cgtagaggat tcacaggacg ggtgtggtcg ccatgatcgc gtagtcgata   3900
gtggctccaa gtagcgaagc gagcaggact gggcggcggc caaagcggtc ggacagtgct   3960
ccgagaacgg gtgcgcatag aaattgcatc aacgcatata gcgctagcag cacgccatag   4020
tgactggcga tgctgtcgga atggacgata tcccgcaaga ggcccggcag taccggcata   4080
accaagccta tgcctacagc atccagggtg acggtgccga ggatgacgat gagcgcattg   4140
ttagatttca tacacggtgc ctgactgcgt tagcaattta actgtgataa actaccgcat   4200
taaagcttat cgatgataag ctgtcaaaca tgagaa                             4236
```

<210> SEQ ID NO 6
<211> LENGTH: 4391
<212> TYPE: DNA
<213> ORGANISM: Artificial Sequence
<220> FEATURE:
<223> OTHER INFORMATION: Synthetic construct: pBR-CBST-KPC-2

<400> SEQUENCE: 6

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtca tatgtcactg tatcgccgtc tagttctgct    240
gtcttgtctc tcatggccgc tggctggctt ttctgccacc gcgctgacca acctcgtcgc    300
ggaaccattc gctaaactcg aacaggactt tggcggctcc atcggtgtgt acgcgatgga    360
taccggctca ggcgcaactg taagttaccg cgctgaggag cgcttcccac tgtgcagctc    420
attcaagggc tttcttgctg ccgctgtgct ggctcgcagc cagcagcagg ccggcttgct    480
ggacacaccc atccgttacg gcaaaaatgc gctggttccg tggtcaccca tctcggaaaa    540
atatctgaca acaggcatga cggtggcgga gctgtccgcg gccgccgtgc aatacagtga    600
taacgccgcc gccaatttgt tgctgaagga gttgggcggc ccggccgggc tgacggcctt    660
catgcgctct atcggcgata ccacgttccg tctggaccgc tgggagctgg agctgaactc    720
cgccatccca ggcgatgcgc gcgatacctc atcgccgcgc gccgtgacgg aaagcttaca    780
aaaactgaca ctgggctctg cactggctgc gccgcagcgg cagcagtttg ttgattggct    840
aaagggaaac acgaccggca accaccgcat ccgcgcggcg gtgccggcag actgggcagt    900
cggagacaaa accggaacct gcggagtgta tggcacggca aatgactatg ccgtcgtctg    960
gcccactggg cgcgcaccta ttgtgttggc cgtctacacc cgggcgccta acaaggatga   1020
caagcacagc gaggccgtca tcgccgctgc ggctagactc gcgctcgagg gattgggcgt   1080
caacgggcag taaggatccc tgtcagacca agtttactca tatatacttt agattgattt   1140
aaaacttcat ttttaattta aaaggatcta ggtgaagatc ctttttgata atctcatgac   1200
caaaatccct taacgtgagt tttcgttcca ctgagcgtca gaccccgtag aaaagatcaa   1260
aggatcttct tgagatcctt tttttctgcg cgtaatctgc tgcttgcaaa caaaaaaacc   1320
accgctacca gcggtggttt gtttgccgga tcaagagcta ccaactcttt ttccgaaggt   1380
```

-continued

```
aactggcttc agcagagcgc agataccaaa tactgtcctt ctagtgtagc cgtagttagg   1440
ccaccacttc aagaactctg tagcaccgcc tacatacctc gctctgctaa tcctgttacc   1500
agtggctgct gccagtggcg ataagtcgtg tcttaccggg ttggactcaa gacgatagtt   1560
accggataag gcgcagcggt cgggctgaac ggggggttcg tgcacacagc ccagcttgga   1620
gcgaacgacc tacaccgaac tgagatacct acagcgtgag ctatgagaaa gcgccacgct   1680
tcccgaaggg agaaaggcgg acaggtatcc ggtaagcggc agggtcggaa caggagagcg   1740
cacgagggag cttccagggg gaaacgcctg gtatctttat agtcctgtcg ggtttcgcca   1800
cctctgactt gagcgtcgat ttttgtgatg ctcgtcaggg gggcggagcc tatggaaaaa   1860
cgccagcaac gcggcctttt tacggttcct ggccttttgc tggccttttg ctcacatgtt   1920
ctttcctgcg ttatcccctg attctgtgga taaccgtatt accgcctttg agtgagctga   1980
taccgctcgc cgcagccgaa cgaccgagcg cagcgagtca gtgagcgagg aagcggaaga   2040
gcgcctgatg cggtattttc tccttacgca tctgtgcggt atttcacacc gcatttggtg   2100
cactctcagt acaatctgct ctgatgccgc atagttaagc cagtatacac tccgctatcg   2160
ctacgtgact gggtcatggc tgcgccccga cacccgccaa cacccgctga cgcgccctga   2220
cgggcttgtc tgctcccggc atccgcttac agacaagctg tgaccgtctc cgggagctgc   2280
atgtgtcaga ggttttcacc gtcatcaccg aaacgcgcga ggcagctgcg gtaaagctca   2340
tcagcgtggt cgtgaagcga ttcacagatg tctgcctgtt catccgcgtc cagctcgttg   2400
agtttctcca gaagcgttaa tgtctggctt ctgataaagc gggccatgtt aagggcggtt   2460
ttttcctgtt tggtcactga tgcctccgtg taagggggat ttctgttcat gggggtaatg   2520
ataccgatga aacgagagag gatgctcacg atacgggtta ctgatgatga acatgcccgg   2580
ttactggaac gttgtgaggg taaacaactg gcggtatgga tgcggcggga ccagagaaaa   2640
atcactcagg gtcaatgcca gcgcttcgtt aatacagatg taggtgttcc acagggtagc   2700
cagcagcatc ctgcgatgca gatccggaac ataatggtgc agggcgctga cttccgcgtt   2760
tccagacttt acgaaacacg gaaaccgaag accattcatg ttgttgctca ggtcgcagac   2820
gttttgcagc agcagtcgct tcacgttcgc tcgcgtatcg gtgattcatt ctgctaacca   2880
gtaaggcaac cccgccagcc tagccgggtc ctcaacgaca ggagcacgat catgcgcacc   2940
cgtggccagg acccaacgct gcccgagatg cgccgcgtgc ggctgctgga gatggcggac   3000
gcgatggata tgttctgcca agggttggtt tgcgcattca cagttctccg caagaattga   3060
ttggctccaa ttcttggagt ggtgaatccg ttagcgaggt gccgccggct tccattcagg   3120
tcgaggtggc ccggctccat gcaccgcgac gcaacgcggg gaggcagaca aggtataggg   3180
cggcgcctac aatccatgcc aacccgttcc atgtgctcgc cgaggcggca taaatcgccg   3240
tgacgatcag cggtccagtg atcgaagtta ggctggtaag agccgcgagc gatccttgaa   3300
gctgtccctg atggtcgtca tctacctgcc tggacagcat ggcctgcaac gcgggcatcc   3360
cgatgccgcc ggaagcgaga agaatcataa tggggaaggc catccagcct cgcgtcgcga   3420
acgccagcaa gacgtagccc agcgcgtcgg ccgccatgcc ggcgataatg gcctgcttct   3480
cgccgaaacg tttggtggcg ggaccagtga cgaaggcttg agcgagggcg tgcaagattc   3540
cgaataccgc aagcgacagg ccgatcatcg tcgcgctcca gcgaaagcgg tcctcgccga   3600
aaatgaccca gagcgctgcc ggcacctgtc ctacgagttg catgataaag aagacagtca   3660
taagtgcggc gacgatagtc atgccccgcg cccaccggaa ggagctgact gggttgaagg   3720
ctctcaaggg catcggtcga cgctctccct tatgcgactc ctgcattagg aagcagccca   3780
```

```
gtagtaggtt gaggccgttg agcaccgccg ccgcaaggaa tggtgcatgc aaggagatgg   3840
cgcccaacag tcccccggcc acggggcctg ccaccatacc cacgccgaaa caagcgctca   3900
tgagcccgaa gtggcgagcc cgatcttccc catcggtgat gtcggcgata taggcgccag   3960
caaccgcacc tgtggcgccg gtgatgccgg ccacgatgcg tccggcgtag aggattcaca   4020
ggacgggtgt ggtcgccatg atcgcgtagt cgatagtggc tccaagtagc gaagcgagca   4080
ggactgggcg gcggccaaag cggtcggaca gtgctccgag aacgggtgcg catagaaatt   4140
gcatcaacgc atatagcgct agcagcacgc catagtgact ggcgatgctg tcggaatgga   4200
cgatatcccg caagaggccc ggcagtaccg gcataaccaa gcctatgcct acagcatcca   4260
gggtgacggt gccgaggatg acgatgagcg cattgttaga tttcatacac ggtgcctgac   4320
tgcgttagca atttaactgt gataaactac cgcattaaag cttatcgatg ataagctgtc   4380
aaacatgaga a                                                        4391
```

<210> SEQ ID NO 7
<211> LENGTH: 4116
<212> TYPE: DNA
<213> ORGANISM: Artificial Sequence
<220> FEATURE:
<223> OTHER INFORMATION: Synthetic construct: pBR-CBST-CTX-M-15

<400> SEQUENCE: 7

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtca tatggaatct gttaaatcag cgagttgaga    240
tcaaaaaatc tgaccttgtt aactataatc cgattgcgga aaagcacgtc aatgggacga    300
tgtcactggc tgagcttagc gcggccgcgc tacagtacag cgataacgtg gcgatgaata    360
agctgattgc tcacgttggc ggcccggcta gcgtcaccgc gttcgcccga cagctgggag    420
acgaaacgtt ccgtctcgac cgtaccgagc cgacgttaaa caccgccatt ccgggcgatc    480
cgcgtgatac cacttcacct cgggcaatgg cgcaaactct gcggaatctg acgctgggta    540
aagcattggg cgacagccaa cgggcgcagc tggtgacatg gatgaaaggc aataccaccg    600
gtgcagcgag cattcaggct ggactgcctg cttcctgggt tgtgggggat aaaaccggca    660
gcggtggcta tggcaccacc aacgatatcg cggtgatctg gccaaaagat cgtgcgccgc    720
tgattctggt cacttacttc acccagcctc aacctaaggc agaaagccgt cgcgatgtat    780
tagcgtcggc ggctaaaatc gtcaccgacg gtttgtaagg atccctgtca gaccaagttt    840
actcatatat actttagatt gatttaaaac ttcattttta atttaaaagg atctaggtga    900
agatcctttt tgataatctc atgaccaaaa tcccttaacg tgagttttcg ttccactgag    960
cgtcagaccc cgtagaaaag atcaaaggat cttcttgaga tccttttttt ctgcgcgtaa   1020
tctgctgctt gcaaacaaaa aaaccaccgc taccagcggt ggtttgtttg ccggatcaag   1080
agctaccaac tctttttccg aaggtaactg gcttcagcag agcgcagata ccaaatactg   1140
tccttctagt gtagccgtag ttaggccacc acttcaagaa ctctgtagca ccgcctacat   1200
acctcgctct gctaatcctg ttaccagtgg ctgctgccag tggcgataag tcgtgtctta   1260
ccgggttgga ctcaagacga tagttaccgg ataaggcgca gcggtcgggc tgaacggggg   1320
gttcgtgcac acagcccagc ttggagcgaa cgacctacac cgaactgaga tacctacagc   1380
```

-continued

```
gtgagctatg agaaagcgcc acgcttcccg aagggagaaa ggcggacagg tatccggtaa   1440
gcggcagggt cggaacagga gagcgcacga gggagcttcc agggggaaac gcctggtatc   1500
tttatagtcc tgtcgggttt cgccacctct gacttgagcg tcgatttttg tgatgctcgt   1560
caggggggcg gagcctatgg aaaaacgcca gcaacgcggc ctttttacgg ttcctggcct   1620
tttgctggcc ttttgctcac atgttctttc ctgcgttatc ccctgattct gtggataacc   1680
gtattaccgc ctttgagtga gctgataccg ctcgccgcag ccgaacgacc gagcgcagcg   1740
agtcagtgag cgaggaagcg gaagagcgcc tgatgcggta ttttctcctt acgcatctgt   1800
gcggtatttc acaccgcatt tggtgcactc tcagtacaat ctgctctgat gccgcatagt   1860
taagccagta tacactccgc tatcgctacg tgactgggtc atggctgcgc cccgacaccc   1920
gccaacaccc gctgacgcgc cctgacgggc ttgtctgctc ccggcatccg cttacagaca   1980
agctgtgacc gtctccggga gctgcatgtg tcagaggttt tcaccgtcat caccgaaacg   2040
cgcgaggcag ctgcggtaaa gctcatcagc gtggtcgtga agcgattcac agatgtctgc   2100
ctgttcatcc gcgtccagct cgttgagttt ctccagaagc gttaatgtct ggcttctgat   2160
aaagcgggcc atgttaaggg cggttttttc ctgtttggtc actgatgcct ccgtgtaagg   2220
gggatttctg ttcatggggg taatgatacc gatgaaacga gagaggatgc tcacgatacg   2280
ggttactgat gatgaacatg cccggttact ggaacgttgt gagggtaaac aactggcggt   2340
atggatgcgg cgggaccaga gaaaaatcac tcagggtcaa tgccagcgct tcgttaatac   2400
agatgtaggt gttccacagg gtagccagca gcatcctgcg atgcagatcc ggaacataat   2460
ggtgcagggc gctgacttcc gcgtttccag actttacgaa acacggaaac cgaagaccat   2520
tcatgttgtt gctcaggtcg cagacgtttt gcagcagcag tcgcttcacg ttcgctcgcg   2580
tatcggtgat tcattctgct aaccagtaag gcaaccccgc cagcctagcc gggtcctcaa   2640
cgacaggagc acgatcatgc gcacccgtgg ccaggaccca acgctgcccg agatgcgccg   2700
cgtgcggctg ctggagatgg cggacgcgat ggatatgttc tgccaagggt tggtttgcgc   2760
attcacagtt ctccgcaaga attgattggc tccaattctt ggagtggtga atccgttagc   2820
gaggtgccgc cggcttccat tcaggtcgag gtggcccggc tccatgcacc gcgacgcaac   2880
gcggggaggc agacaaggta tagggcggcg cctacaatcc atgccaaccc gttccatgtg   2940
ctcgccgagg cggcataaat cgccgtgacg atcagcggtc cagtgatcga agttaggctg   3000
gtaagagccg cgagcgatcc ttgaagctgt ccctgatggt cgtcatctac ctgcctggac   3060
agcatggcct gcaacgcggg catcccgatg ccgccggaag cgagaagaat cataatgggg   3120
aaggccatcc agcctcgcgt cgcgaacgcc agcaagacgt agcccagcgc gtcggccgcc   3180
atgccggcga taatggcctg cttctcgccg aaacgtttgg tggcgggacc agtgacgaag   3240
gcttgagcga gggcgtgcaa gattccgaat accgcaagcg acaggccgat catcgtcgcg   3300
ctccagcgaa agcggtcctc gccgaaaatg acccagagcg ctgccggcac ctgtcctacg   3360
agttgcatga taaagaagac agtcataagt gcggcgacga tagtcatgcc ccgcgcccac   3420
cggaaggagc tgactgggtt gaaggctctc aagggcatcg gtcgacgctc tcccttatgc   3480
gactcctgca ttaggaagca gcccagtagt aggttgaggc cgttgagcac cgccgccgca   3540
aggaatggtg catgcaagga gatggcgccc aacagtcccc cggccacggg gcctgccacc   3600
atacccacgc cgaaacaagc gctcatgagc ccgaagtggc gagcccgatc ttccccatcg   3660
gtgatgtcgg cgatataggc gccagcaacc gcacctgtgg cgccggtgat gccggccacg   3720
atgcgtccgg cgtagaggat tcacaggacg ggtgtggtcg ccatgatcgc gtagtcgata   3780
```

gtggctccaa gtagcgaagc gagcaggact gggcggcggc caaagcggtc ggacagtgct 3840
ccgagaacgg gtgcgcatag aaattgcatc aacgcatata gcgctagcag cacgccatag 3900
tgactggcga tgctgtcgga atggacgata tcccgcaaga ggcccggcag taccggcata 3960
accaagccta tgcctacagc atccagggtg acggtgccga ggatgacgat gagcgcattg 4020
ttagatttca tacacggtgc ctgactgcgt tagcaattta actgtgataa actaccgcat 4080
taaagcttat cgatgataag ctgtcaaaca tgagaa 4116

<210> SEQ ID NO 8
<211> LENGTH: 4370
<212> TYPE: DNA
<213> ORGANISM: Artificial Sequence
<220> FEATURE:
<223> OTHER INFORMATION: Synthetic construct: pBR-CBST-SHV-12

<400> SEQUENCE: 8
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtca tatgcgttat attcgcctgt gtattatctc 240
cctgttagcc accctgccgc tggcggtaca cgccagcccg cagccgcttg agcaaattaa 300
acaaagcgaa agccagctgt cgggccgcgt aggcatgata gaaatggatc tggccagcgg 360
ccgcacgctg accgcctggc gcgccgatga acgctttccc atgatgagca cctttaaagt 420
agtgctctgc ggcgcagtgc tggcgcgggt ggatgccggt gacgaacagc tggagcgaaa 480
gatccactat cgccagcagg atctggtgga ctactcgccg gtcagcgaaa aacaccttgc 540
cgacggcatg acggtcggcg aactctgcgc cgccgccatt accatgagcg ataacagcgc 600
cgccaatctg ctgctggcca ccgtcggcgg ccccgcagga ttgactgcct ttttgcgcca 660
gatcggcgac aacgtcaccc gccttgaccg ctgggaaacg gaactgaatg aggcgcttcc 720
cggcgacgcc cgcgacacca ctaccccggc cagcatggcc gcgaccctgc gcaagctgct 780
gaccagccag cgtctgagcg cccgttcgca acggcagctg ctgcagtgga tggtggacga 840
tcgggtcgcc ggaccgttga tccgctccgt gctgccggcg ggctggttta tcgccgataa 900
gaccggagct agcaagcggg gtgcgcgcgg gattgtcgcc ctgcttggcc cgaataacaa 960
agcagagcgc attgtggtga tttatctgcg ggataccccg gcgagcatgg ccgagcgaaa 1020
tcagcaaatc gccgggatcg gcgcggcgct gatcgagcac tggcaacgct aaggatccct 1080
gtcagaccaa gtttactcat atatacttta gattgattta aaacttcatt tttaatttaa 1140
aaggatctag gtgaagatcc tttttgataa tctcatgacc aaaatccctt aacgtgagtt 1200
ttcgttccac tgagcgtcag accccgtaga aaagatcaaa ggatcttctt gagatccttt 1260
ttttctgcgc gtaatctgct gcttgcaaac aaaaaaacca ccgctaccag cggtggtttg 1320
tttgccggat caagagctac caactctttt tccgaaggta actggcttca gcagagcgca 1380
gataccaaat actgtccttc tagtgtagcc gtagttaggc caccacttca agaactctgt 1440
agcaccgcct acatacctcg ctctgctaat cctgttacca gtggctgctg ccagtggcga 1500
taagtcgtgt cttaccgggt tggactcaag acgatagtta ccggataagg cgcagcggtc 1560
gggctgaacg gggggttcgt gcacacagcc cagcttggag cgaacgacct acaccgaact 1620
gagataccta cagcgtgagc tatgagaaag cgccacgctt cccgaaggga gaaaggcgga 1680

-continued caggtatccg gtaagcggca gggtcggaac aggagagcgc acgagggagc ttccaggggg 1740
aaacgcctgg tatctttata gtcctgtcgg gtttcgccac ctctgacttg agcgtcgatt 1800
tttgtgatgc tcgtcagggg ggcggagcct atggaaaaac gccagcaacg cggccttttt 1860
acggttcctg gccttttgct ggccttttgc tcacatgttc tttcctgcgt tatcccctga 1920
ttctgtggat aaccgtatta ccgcctttga gtgagctgat accgctcgcc gcagccgaac 1980
gaccgagcgc agcgagtcag tgagcgagga agcggaagag cgcctgatgc ggtattttct 2040
ccttacgcat ctgtgcggta tttcacaccg catttggtgc actctcagta caatctgctc 2100
tgatgccgca tagttaagcc agtatacact ccgctatcgc tacgtgactg ggtcatggct 2160
gcgccccgac acccgccaac acccgctgac gcgccctgac gggcttgtct gctcccggca 2220
tccgcttaca gacaagctgt gaccgtctcc gggagctgca tgtgtcagag gttttcaccg 2280
tcatcaccga aacgcgcgag gcagctgcgg taaagctcat cagcgtggtc gtgaagcgat 2340
tcacagatgt ctgcctgttc atccgcgtcc agctcgttga gtttctccag aagcgttaat 2400
gtctggcttc tgataaagcg ggccatgtta agggcggttt tttcctgttt ggtcactgat 2460
gcctccgtgt aagggggatt tctgttcatg ggggtaatga taccgatgaa acgagagagg 2520
atgctcacga tacgggttac tgatgatgaa catgcccggt tactggaacg ttgtgagggt 2580
aaacaactgg cggtatggat gcggcgggac cagagaaaaa tcactcaggg tcaatgccag 2640
cgcttcgtta atacagatgt aggtgttcca cagggtagcc agcagcatcc tgcgatgcag 2700
atccggaaca taatggtgca gggcgctgac ttccgcgttt ccagacttta cgaaacacgg 2760
aaaccgaaga ccattcatgt tgttgctcag gtcgcagacg ttttgcagca gcagtcgctt 2820
cacgttcgct cgcgtatcgg tgattcattc tgctaaccag taaggcaacc ccgccagcct 2880
agccgggtcc tcaacgacag gagcacgatc atgcgcaccc gtggccagga cccaacgctg 2940
cccgagatgc gccgcgtgcg gctgctggag atggcggacg cgatggatat gttctgccaa 3000
gggttggttt gcgcattcac agttctccgc aagaattgat tggctccaat tcttggagtg 3060
gtgaatccgt tagcgaggtg ccgccggctt ccattcaggt cgaggtggcc cggctccatg 3120
caccgcgacg caacgcgggg aggcagacaa ggtatagggc ggcgcctaca atccatgcca 3180
acccgttcca tgtgctcgcc gaggcggcat aaatcgccgt gacgatcagc ggtccagtga 3240
tcgaagttag gctggtaaga gccgcgagcg atccttgaag ctgtccctga tggtcgtcat 3300
ctacctgcct ggacagcatg gcctgcaacg cgggcatccc gatgccgccg gaagcgagaa 3360
gaatcataat ggggaaggcc atccagcctc gcgtcgcgaa cgccagcaag acgtagccca 3420
gcgcgtcggc cgccatgccg gcgataatgg cctgcttctc gccgaaacgt ttggtggcgg 3480
gaccagtgac gaaggcttga gcgagggcgt gcaagattcc gaataccgca agcgacaggc 3540
cgatcatcgt cgcgctccag cgaaagcggt cctcgccgaa aatgacccag agcgctgccg 3600
gcacctgtcc tacgagttgc atgataaaga agacagtcat aagtgcggcg acgatagtca 3660
tgccccgcgc ccaccggaag gagctgactg ggttgaaggc tctcaagggc atcggtcgac 3720
gctctccctt atgcgactcc tgcattagga agcagcccag tagtaggttg aggccgttga 3780
gcaccgccgc cgcaaggaat ggtgcatgca aggagatggc gcccaacagt cccccggcca 3840
cggggcctgc caccataccc acgccgaaac aagcgctcat gagcccgaag tggcgagccc 3900
gatcttcccc atcggtgatg tcggcgatat aggcgccagc aaccgcacct gtggcgccgg 3960
tgatgccggc cacgatgcgt ccggcgtaga ggattcacag gacgggtgtg gtcgccatga 4020
tcgcgtagtc gatagtggct ccaagtagcg aagcgagcag gactgggcgg cggccaaagc 4080

```
ggtcggacag tgctccgaga acgggtgcgc atagaaattg catcaacgca tatagcgcta   4140

gcagcacgcc atagtgactg gcgatgctgt cggaatggac gatatcccgc aagaggcccg   4200

gcagtaccgg cataaccaag cctatgccta cagcatccag ggtgacggtg ccgaggatga   4260

cgatgagcgc attgttagat ttcatacacg gtgcctgact gcgttagcaa tttaactgtg   4320

ataaactacc gcattaaagc ttatcgatga taagctgtca aacatgagaa              4370


<210> SEQ ID NO 9
<211> LENGTH: 4655
<212> TYPE: DNA
<213> ORGANISM: Artificial Sequence
<220> FEATURE:
<223> OTHER INFORMATION: Synthetic construct: pBR-CBST-P99

<400> SEQUENCE: 9

ttcttgaaga cgaaagggcc tcgtgatacg cctattttta taggttaatg tcatgataat     60

aatggtttct tagacgtcag gtggcacttt tcggggaaat gtgcgcggaa cccctatttg    120

tttatttttc taaatacatt caaatatgta tccgctcatg agacaataac cctgataaat    180

gcttcaataa tattgaaaaa ggaagagtca tatgatgaga aaatcccttt gctgcgccct    240

gctgctcggc atctcttgct ctgctctcgc cacgccagtg tcagaaaaac agctggcgga    300

ggtggtcgcg aatacgatta ccccgctgat gaaagcccag tctgttccag gcatggcggt    360

ggccgttatt tatcagggaa aaccgcacta ttacacattt ggcaaggccg atatcgcggc    420

gaataaaccc gttacgcctc agaccctgtt cgagctgggt tctataagta aaaccttcac    480

cggcgtttta ggtggggatg ccattgctcg cggtgaaatt tcgctggacg atgcggtgac    540

cagatactgg ccacagctga cgggcaagca gtggcagggt attcgtatgc tggatctcgc    600

cacctacacc gctggcggcc tgccgctaca ggtaccggat gaggtcacgg ataacgcctc    660

cctgctgcgc ttttatcaaa actggcagcc gcagtggaag cctggcacaa cgcgtcttta    720

cgccaacgcc agcatcggtc tttttggtgc gctggcggtc aaaccttctg gcatgcccta    780

tgagcaggcc atgacgacgc gggtccttaa gccgctcaag ctggaccata cctggattaa    840

cgtgccgaaa gcggaagagg cgcattacgc ctggggctat cgtgacggta aagcggtgcg    900

cgtttcgccg ggtatgctgg atgcacaagc ctatggcgtg aaaaccaacg tgcaggatat    960

ggcgaactgg gtcatggcaa acatggcgcc ggagaacgtt gctgatgcct cacttaagca   1020

gggcatcgcg ctggcgcagt cgcgctactg gcgtatcggg tcaatgtatc agggtctggg   1080

ctgggagatg ctcaactggc ccgtggaggc caacacggtg gtcgagggca gcgacagtaa   1140

ggtagcactg gcgccgttgc ccgtggcaga agtgaatcca ccggctcccc cggtcaaagc   1200

gtcctgggtc cataaaacgg gctctactgg cgggtttggc agctacgtgg cctttattcc   1260

tgaaaagcag atcggtattg tgatgctcgc gaatacaagc tatccgaacc cggcacgcgt   1320

tgaggcggca taccatatcc tcgaggcgct acagtaagga tccctgtcag accaagttta   1380

ctcatatata ctttagattg atttaaaact tcatttttaa tttaaaagga tctaggtgaa   1440

gatccttttt gataatctca tgaccaaaat cccttaacgt gagttttcgt tccactgagc   1500

gtcagacccc gtagaaaaga tcaaaggatc ttcttgagat cctttttttc tgcgcgtaat   1560

ctgctgcttg caaacaaaaa aaccaccgct accagcggtg gtttgtttgc cggatcaaga   1620

gctaccaact ctttttccga aggtaactgg cttcagcaga gcgcagatac caaatactgt   1680

ccttctagtg tagccgtagt taggccacca cttcaagaac tctgtagcac cgcctacata   1740
```

-continued

```
cctcgctctg ctaatcctgt taccagtggc tgctgccagt ggcgataagt cgtgtcttac   1800
cgggttggac tcaagacgat agttaccgga taaggcgcag cggtcgggct gaacgggggg   1860
ttcgtgcaca cagcccagct tggagcgaac gacctacacc gaactgagat acctacagcg   1920
tgagctatga gaaagcgcca cgcttcccga agggagaaag gcggacaggt atccggtaag   1980
cggcagggtc ggaacaggag agcgcacgag ggagcttcca gggggaaacg cctggtatct   2040
ttatagtcct gtcgggtttc gccacctctg acttgagcgt cgatttttgt gatgctcgtc   2100
aggggggcgg agcctatgga aaaacgccag caacgcggcc tttttacggt tcctggcctt   2160
ttgctggcct tttgctcaca tgttctttcc tgcgttatcc cctgattctg tggataaccg   2220
tattaccgcc tttgagtgag ctgataccgc tcgccgcagc cgaacgaccg agcgcagcga   2280
gtcagtgagc gaggaagcgg aagagcgcct gatgcggtat tttctcctta cgcatctgtg   2340
cggtatttca caccgcattt ggtgcactct cagtacaatc tgctctgatg ccgcatagtt   2400
aagccagtat acactccgct atcgctacgt gactgggtca tggctgcgcc ccgacacccg   2460
ccaacacccg ctgacgcgcc ctgacgggct tgtctgctcc cggcatccgc ttacagacaa   2520
gctgtgaccg tctccgggag ctgcatgtgt cagaggtttt caccgtcatc accgaaacgc   2580
gcgaggcagc tgcggtaaag ctcatcagcg tggtcgtgaa gcgattcaca gatgtctgcc   2640
tgttcatccg cgtccagctc gttgagtttc tccagaagcg ttaatgtctg gcttctgata   2700
aagcgggcca tgttaagggc ggttttttcc tgtttggtca ctgatgcctc cgtgtaaggg   2760
ggatttctgt tcatgggggt aatgataccg atgaaacgag agaggatgct cacgatacgg   2820
gttactgatg atgaacatgc ccggttactg gaacgttgtg agggtaaaca actggcggta   2880
tggatgcggc gggaccagag aaaaatcact cagggtcaat gccagcgctt cgttaataca   2940
gatgtaggtg ttccacaggg tagccagcag catcctgcga tgcagatccg gaacataatg   3000
gtgcagggcg ctgacttccg cgtttccaga ctttacgaaa cacggaaacc gaagaccatt   3060
catgttgttg ctcaggtcgc agacgttttg cagcagcagt cgcttcacgt tcgctcgcgt   3120
atcggtgatt cattctgcta accagtaagg caaccccgcc agcctagccg ggtcctcaac   3180
gacaggagca cgatcatgcg cacccgtggc caggacccaa cgctgcccga gatgcgccgc   3240
gtgcggctgc tggagatggc ggacgcgatg gatatgttct gccaagggtt ggtttgcgca   3300
ttcacagttc tccgcaagaa ttgattggct ccaattcttg gagtggtgaa tccgttagcg   3360
aggtgccgcc ggcttccatt caggtcgagg tggcccggct ccatgcaccg cgacgcaacg   3420
cggggaggca gacaaggtat agggcggcgc ctacaatcca tgccaacccg ttccatgtgc   3480
tcgccgaggc ggcataaatc gccgtgacga tcagcggtcc agtgatcgaa gttaggctgg   3540
taagagccgc gagcgatcct tgaagctgtc cctgatggtc gtcatctacc tgcctggaca   3600
gcatggcctg caacgcgggc atcccgatgc cgccggaagc gagaagaatc ataatgggga   3660
aggccatcca gcctcgcgtc gcgaacgcca gcaagacgta gcccagcgcg tcggccgcca   3720
tgccggcgat aatggcctgc ttctcgccga aacgtttggt ggcgggacca gtgacgaagg   3780
cttgagcgag ggcgtgcaag attccgaata ccgcaagcga caggccgatc atcgtcgcgc   3840
tccagcgaaa gcggtcctcg ccgaaaatga cccagagcgc tgccggcacc tgtcctacga   3900
gttgcatgat aaagaagaca gtcataagtg cggcgacgat agtcatgccc cgcgcccacc   3960
ggaaggagct gactgggttg aaggctctca agggcatcgg tcgacgctct cccttatgcg   4020
actcctgcat taggaagcag cccagtagta ggttgaggcc gttgagcacc gccgccgcaa   4080
ggaatggtgc atgcaaggag atggcgccca acagtccccc ggccacgggg cctgccacca   4140
```

tacccacgcc gaaacaagcg ctcatgagcc cgaagtggcg agcccgatct tccccatcgg 4200
tgatgtcggc gatataggcg ccagcaaccg cacctgtggc gccggtgatg ccggccacga 4260
tgcgtccggc gtagaggatt cacaggacgg gtgtggtcgc catgatcgcg tagtcgatag 4320
tggctccaag tagcgaagcg agcaggactg ggcggcggcc aaagcggtcg gacagtgctc 4380
cgagaacggg tgcgcataga aattgcatca acgcatatag cgctagcagc acgccatagt 4440
gactggcgat gctgtcggaa tggacgatat cccgcaagag gcccggcagt accggcataa 4500
ccaagcctat gcctacagca tccagggtga cggtgccgag gatgacgatg agcgcattgt 4560
tagatttcat acacggtgcc tgactgcgtt agcaatttaa ctgtgataaa ctaccgcatt 4620
aaagcttatc gatgataagc tgtcaaacat gagaa 4655

<210> SEQ ID NO 10
<211> LENGTH: 4337
<212> TYPE: DNA
<213> ORGANISM: Artificial Sequence
<220> FEATURE:
<223> OTHER INFORMATION: Synthetic construct: pBR-CBST-OXA-15

<400> SEQUENCE: 10
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtca tatggcaatc cgaatcttcg cgatactttt 240
ctccattttt tctcttgcca ctttcgcgca tgcgcaagaa ggcacgctag aacgttctga 300
ctggaggaag tttttcagcg aatttcaagc caaaggcacg atagttgtgg cagacgaacg 360
ccaagcggat cgtgccatgt tggtttttga tcctgtgcga tcgaagaaac gctactcgcc 420
tgcatcgaca ttcaagatac ctcatacact tttgcactt gatgcaggcg ctgttcgtga 480
tgagttccag atttttcgat gggacggcgt taacaggggc tttgcaggcc acaatcaaga 540
ccaagatttg cgatcagcaa tgcggaattc tactgtttgg gtgtatgagc tatttgcaaa 600
ggaaattggt gatgacaaag ctcggcgcta tttgaagaaa atcgactatg gcaacgccgg 660
tccttcgaca agtaatggcg attactggat agaaggcagc cttgcaatct cggcgcagga 720
gcaaattgca tttctcagga agctctatcg taacgagctg ccctttcggg tagaacatca 780
gcgcttggtc aaggatctca tgattgtgga agccggtcgc aactggatac tgcgtgcaaa 840
gacgggctgg gaaggccgta tgggttggtg ggtaggatgg gttgagtggc cgactggctc 900
cgtattcttc gcactgaata ttgatacgcc aaacagaatg gatgatcttt tcaagaggga 960
ggcaatcgtg cgggcaatcc ttcgctctat tgaagcgtta ccgcccaacc cggcagtcaa 1020
ctcggacgct gcgcgataag gatccctgtc agaccaagtt tactcatata tactttagat 1080
tgatttaaaa cttcattttt aatttaaaag gatctaggtg aagatccttt ttgataatct 1140
catgaccaaa atcccttaac gtgagttttc gttccactga gcgtcagacc ccgtagaaaa 1200
gatcaaagga tcttcttgag atcctttttt tctgcgcgta atctgctgct tgcaaacaaa 1260
aaaaccaccg ctaccagcgg tggtttgttt gccggatcaa gagctaccaa ctctttttcc 1320
gaaggtaact ggcttcagca gagcgcagat accaaatact gtccttctag tgtagccgta 1380
gttaggccac cacttcaaga actctgtagc accgcctaca tacctcgctc tgctaatcct 1440
gttaccagtg gctgctgcca gtggcgataa gtcgtgtctt accgggttgg actcaagacg 1500

-continued

```
atagttaccg gataaggcgc agcggtcggg ctgaacgggg ggttcgtgca cacagcccag   1560
cttggagcga acgacctaca ccgaactgag atacctacag cgtgagctat gagaaagcgc   1620
cacgcttccc gaagggagaa aggcggacag gtatccggta agcggcaggg tcggaacagg   1680
agagcgcacg agggagcttc caggggggaaa cgcctggtat ctttatagtc ctgtcgggtt   1740
tcgccacctc tgacttgagc gtcgattttt gtgatgctcg tcaggggggc ggagcctatg   1800
gaaaaacgcc agcaacgcgg cctttttacg gttcctggcc ttttgctggc cttttgctca   1860
catgttcttt cctgcgttat cccctgattc tgtggataac cgtattaccg cctttgagtg   1920
agctgatacc gctcgccgca gccgaacgac cgagcgcagc gagtcagtga gcgaggaagc   1980
ggaagagcgc ctgatgcggt attttctcct tacgcatctg tgcggtattt cacaccgcat   2040
ttggtgcact ctcagtacaa tctgctctga tgccgcatag ttaagccagt atacactccg   2100
ctatcgctac gtgactgggt catggctgcg ccccgacacc cgccaacacc cgctgacgcg   2160
ccctgacggg cttgtctgct cccggcatcc gcttacagac aagctgtgac cgtctccggg   2220
agctgcatgt gtcagaggtt ttcaccgtca tcaccgaaac gcgcgaggca gctgcggtaa   2280
agctcatcag cgtggtcgtg aagcgattca cagatgtctg cctgttcatc cgcgtccagc   2340
tcgttgagtt tctccagaag cgttaatgtc tggcttctga taaagcgggc catgttaagg   2400
gcggtttttt cctgtttggt cactgatgcc tccgtgtaag ggggatttct gttcatgggg   2460
gtaatgatac cgatgaaacg agagaggatg ctcacgatac gggttactga tgatgaacat   2520
gcccggttac tggaacgttg tgagggtaaa caactggcgg tatggatgcg gcgggaccag   2580
agaaaaatca ctcagggtca atgccagcgc ttcgttaata cagatgtagg tgttccacag   2640
ggtagccagc agcatcctgc gatgcagatc cggaacataa tggtgcaggg cgctgacttc   2700
cgcgtttcca gactttacga aacacggaaa ccgaagacca ttcatgttgt tgctcaggtc   2760
gcagacgttt tgcagcagca gtcgcttcac gttcgctcgc gtatcggtga ttcattctgc   2820
taaccagtaa ggcaaccccg ccagcctagc cgggtcctca acgacaggag cacgatcatg   2880
cgcacccgtg gccaggaccc aacgctgccc gagatgcgcc gcgtgcggct gctggagatg   2940
gcggacgcga tggatatgtt ctgccaaggg ttggtttgcg cattcacagt tctccgcaag   3000
aattgattgg ctccaattct tggagtggtg aatccgttag cgaggtgccg ccggcttcca   3060
ttcaggtcga ggtggcccgg ctccatgcac cgcgacgcaa cgcggggagg cagacaaggt   3120
atagggcggc gcctacaatc catgccaacc cgttccatgt gctcgccgag gcggcataaa   3180
tcgccgtgac gatcagcggt ccagtgatcg aagttaggct ggtaagagcc gcgagcgatc   3240
cttgaagctg tccctgatgg tcgtcatcta cctgcctgga cagcatggcc tgcaacgcgg   3300
gcatcccgat gccgccggaa gcgagaagaa tcataatggg gaaggccatc cagcctcgcg   3360
tcgcgaacgc cagcaagacg tagcccagcg cgtcggccgc catgccggcg ataatggcct   3420
gcttctcgcc gaaacgtttg gtggcgggac cagtgacgaa ggcttgagcg agggcgtgca   3480
agattccgaa taccgcaagc gacaggccga tcatcgtcgc gctccagcga aagcggtcct   3540
cgccgaaaat gacccagagc gctgccggca cctgtcctac gagttgcatg ataaagaaga   3600
cagtcataag tgcggcgacg atagtcatgc cccgcgccca ccggaaggag ctgactgggt   3660
tgaaggctct caagggcatc ggtcgacgct ctcccttatg cgactcctgc attaggaagc   3720
agcccagtag taggttgagg ccgttgagca ccgccgccgc aaggaatggt gcatgcaagg   3780
agatggcgcc caacagtccc ccggccacgg ggcctgccac catacccacg ccgaaacaag   3840
cgctcatgag cccgaagtgg cgagcccgat cttccccatc ggtgatgtcg gcgatatagg   3900
```

cgccagcaac cgcacctgtg gcgccggtga tgccggccac gatgcgtccg gcgtagagga 3960
ttcacaggac gggtgtggtc gccatgatcg cgtagtcgat agtggctcca agtagcgaag 4020
cgagcaggac tgggcggcgg ccaaagcggt cggacagtgc tccgagaacg ggtgcgcata 4080
gaaattgcat caacgcatat agcgctagca gcacgccata gtgactggcg atgctgtcgg 4140
aatggacgat atcccgcaag aggcccggca gtaccggcat aaccaagcct atgcctacag 4200
catccagggt gacggtgccg aggatgacga tgagcgcatt gttagatttc atacacggtg 4260
cctgactgcg ttagcaattt aactgtgata aactaccgca ttaaagctta tcgatgataa 4320
gctgtcaaac atgagaa 4337

<210> SEQ ID NO 11
<211> LENGTH: 4391
<212> TYPE: DNA
<213> ORGANISM: Artificial Sequence
<220> FEATURE:
<223> OTHER INFORMATION: Synthetic construct: pBR-CBST-KPC-4

<400> SEQUENCE: 11
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtca tatgtcactg tatcgccgtc tagttctgct 240
gtcttgtctc tcatggccgc tggctggctt ttctgccacc gcgctgacca acctcgtcgc 300
ggaaccattc gctaaactcg aacaggactt tggcggctcc atcggtgtgt acgcgatgga 360
taccggctca ggcgcaactg taagttaccg cgctgaggag cgcttcccac tgtgcagctc 420
attcaagggc tttcttgctg ccgctgtgct ggctcgcagc cagcagcagg ccggcttgct 480
ggacacaccc atccgttacg gcaaaaatgc gctggttcgg tggtcaccca tctcggaaaa 540
atatctgaca acaggcatga cggtggcgga gctgtccgcg gccgccgtgc aatacagtga 600
taacgccgcc gccaatttgt tgctgaagga gttgggcggc ccggccgggc tgacggcctt 660
catgcgctct atcggcgata ccacgttccg tctggaccgc tgggagctgg agctgaactc 720
cgccatccca ggcgatgcgc gcgatacctc atcgccgcgc gccgtgacgg aaagcttaca 780
aaaactgaca ctgggctctg cactggctgc gccgcagcgg cagcagtttg ttgattggct 840
aaagggaaac acgaccggca accaccgcat ccgcgcggcg gtgccggcag actgggcagt 900
cggagacaaa accggaacct gcggagggta tggcacggca aatgactatg ccgtcgtctg 960
gcccactggg cgcgcaccta ttgtgttggc cgtctacacc cgggcgccta acaaggatga 1020
caagcacagc gaggccgtca tcgccgctgc ggctagactc gcgctcgagg gattgggcgt 1080
caacgggcag taaggatccc tgtcagacca agtttactca tatatacttt agattgattt 1140
aaaacttcat ttttaattta aaaggatcta ggtgaagatc ctttttgata atctcatgac 1200
caaaatccct taacgtgagt tttcgttcca ctgagcgtca gaccccgtag aaaagatcaa 1260
aggatcttct tgagatcctt tttttctgcg cgtaatctgc tgcttgcaaa caaaaaaacc 1320
accgctacca gcggtggttt gtttgccgga tcaagagcta ccaactcttt ttccgaaggt 1380
aactggcttc agcagagcgc agataccaaa tactgtcctt ctagtgtagc cgtagttagg 1440
ccaccacttc aagaactctg tagcaccgcc tacatacctc gctctgctaa tcctgttacc 1500
agtggctgct gccagtggcg ataagtcgtg tcttaccggg ttggactcaa gacgatagtt 1560

```
accggataag gcgcagcggt cgggctgaac ggggggttcg tgcacacagc ccagcttgga   1620
gcgaacgacc tacaccgaac tgagatacct acagcgtgag ctatgagaaa gcgccacgct   1680
tcccgaaggg agaaaggcgg acaggtatcc ggtaagcggc agggtcggaa caggagagcg   1740
cacgagggag cttccagggg gaaacgcctg gtatctttat agtcctgtcg ggtttcgcca   1800
cctctgactt gagcgtcgat ttttgtgatg ctcgtcaggg gggcggagcc tatggaaaaa   1860
cgccagcaac gcggcctttt tacggttcct ggccttttgc tggccttttg ctcacatgtt   1920
ctttcctgcg ttatcccctg attctgtgga taaccgtatt accgcctttg agtgagctga   1980
taccgctcgc cgcagccgaa cgaccgagcg cagcgagtca gtgagcgagg aagcggaaga   2040
gcgcctgatg cggtattttc tccttacgca tctgtgcggt atttcacacc gcatttggtg   2100
cactctcagt acaatctgct ctgatgccgc atagttaagc cagtatacac tccgctatcg   2160
ctacgtgact gggtcatggc tgcgccccga cacccgccaa cacccgctga cgcgccctga   2220
cgggcttgtc tgctcccggc atccgcttac agacaagctg tgaccgtctc cgggagctgc   2280
atgtgtcaga ggttttcacc gtcatcaccg aaacgcgcga ggcagctgcg gtaaagctca   2340
tcagcgtggt cgtgaagcga ttcacagatg tctgcctgtt catccgcgtc cagctcgttg   2400
agtttctcca gaagcgttaa tgtctggctt ctgataaagc gggccatgtt aagggcggtt   2460
ttttcctgtt tggtcactga tgcctccgtg taagggggat ttctgttcat gggggtaatg   2520
ataccgatga aacgagagag gatgctcacg atacgggtta ctgatgatga acatgcccgg   2580
ttactggaac gttgtgaggg taaacaactg gcggtatgga tgcggcggga ccagagaaaa   2640
atcactcagg gtcaatgcca gcgcttcgtt aatacagatg taggtgttcc acagggtagc   2700
cagcagcatc ctgcgatgca gatccggaac ataatggtgc agggcgctga cttccgcgtt   2760
tccagacttt acgaaacacg gaaaccgaag accattcatg ttgttgctca ggtcgcagac   2820
gttttgcagc agcagtcgct tcacgttcgc tcgcgtatcg gtgattcatt ctgctaacca   2880
gtaaggcaac cccgccagcc tagccgggtc ctcaacgaca ggagcacgat catgcgcacc   2940
cgtggccagg acccaacgct gcccgagatg cgccgcgtgc ggctgctgga gatggcggac   3000
gcgatggata tgttctgcca agggttggtt tgcgcattca cagttctccg caagaattga   3060
ttggctccaa ttcttggagt ggtgaatccg ttagcgaggt gccgccggct tccattcagg   3120
tcgaggtggc ccggctccat gcaccgcgac gcaacgcggg gaggcagaca aggtataggg   3180
cggcgcctac aatccatgcc aacccgttcc atgtgctcgc cgaggcggca taaatcgccg   3240
tgacgatcag cggtccagtg atcgaagtta ggctggtaag agccgcgagc gatccttgaa   3300
gctgtccctg atggtcgtca tctacctgcc tggacagcat ggcctgcaac gcgggcatcc   3360
cgatgccgcc ggaagcgaga agaatcataa tggggaaggc catccagcct cgcgtcgcga   3420
acgccagcaa gacgtagccc agcgcgtcgg ccgccatgcc ggcgataatg gcctgcttct   3480
cgccgaaacg tttggtggcg ggaccagtga cgaaggcttg agcgagggcg tgcaagattc   3540
cgaataccgc aagcgacagg ccgatcatcg tcgcgctcca gcgaaagcgg tcctcgccga   3600
aaatgaccca gagcgctgcc ggcacctgtc ctacgagttg catgataaag aagacagtca   3660
taagtgcggc gacgatagtc atgccccgcg cccaccggaa ggagctgact gggttgaagg   3720
ctctcaaggg catcggtcga cgctctccct tatgcgactc ctgcattagg aagcagccca   3780
gtagtaggtt gaggccgttg agcaccgccg ccgcaaggaa tggtgcatgc aaggagatgg   3840
cgcccaacag tcccccggcc acggggcctg ccaccatacc cacgccgaaa caagcgctca   3900
tgagcccgaa gtggcgagcc cgatcttccc catcggtgat gtcggcgata taggcgccag   3960
```

caaccgcacc tgtggcgccg gtgatgccgg ccacgatgcg tccggcgtag aggattcaca 4020
ggacgggtgt ggtcgccatg atcgcgtagt cgatagtggc tccaagtagc gaagcgagca 4080
ggactgggcg gcggccaaag cggtcggaca gtgctccgag aacgggtgcg catagaaatt 4140
gcatcaacgc atatagcgct agcagcacgc catagtgact ggcgatgctg tcggaatgga 4200
cgatatcccg caagaggccc ggcagtaccg gcataaccaa gcctatgcct acagcatcca 4260
gggtgacggt gccgaggatg acgatgagcg cattgttaga tttcatacac ggtgcctgac 4320
tgcgttagca atttaactgt gataaactac cgcattaaag cttatcgatg ataagctgtc 4380
aaacatgaga a 4391

<210> SEQ ID NO 12
<211> LENGTH: 4649
<212> TYPE: DNA
<213> ORGANISM: Artificial Sequence
<220> FEATURE:
<223> OTHER INFORMATION: Synthetic construct: pBR-CBST-DHA-1

<400> SEQUENCE: 12
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtca tatgaaaaaa tcgttatctg caacactgat 240
ttccgctctg ctggcgtttt ccgccccggg gttttctgcc gctgataatg tcgcggcggt 300
ggtggacagc accattaaac cgctgatggc acagcaggat attcccggga tggcggttgc 360
cgtctccgta aagggtaagc cctattattt caattatggt tttgccgata ttcaggcaaa 420
acagccggtc actgaaaata cactatttga gctcggatct gtaagtaaaa ctttcacagg 480
tgtgctgggt gcggtttctg tggcgaaaaa agagatggcg ctgaatgatc cggcggcaaa 540
ataccagccg gagctggctc tgccgcagtg gaaggggatc acattgctgg atctggctac 600
ctataccgca ggcggactgc cgttacaggt gccggatgcg gtaaaaagcc gtgcggatct 660
gctgaatttc tatcagcagt ggcagccgtc ccggaaaccg ggcgatatgc gtctgtatgc 720
aaacagcagt atcggcctgt ttggtgctct gaccgcaaac gcggcgggga tgccgtatga 780
gcagttgctg actgcacgca tcctggcacc gctggggtta tctcacacct ttattactgt 840
gccggaaagt gcgcaaagcc agtatgcgta cggttataaa aacaaaaaac cggtccgcgt 900
gtcgccggga cagcttgatg cggaatctta cggcgtgaaa tccgcctcaa aagatatgct 960
gcgctgggcg gaaatgaata tggagccgtc acgggccggt aatgcggatc tggaaatggc 1020
aatgtatctc gcccagaccc gctactataa aaccgccgcg attaaccagg ggctgggctg 1080
ggaaatgtat gactggccgc agcagaaaga tatgatcatt aacggtgtga ccaacgaggt 1140
cgcattgcag ccgcatccgg taacagacaa ccaggttcag ccgtataacc gtgcttcctg 1200
ggtgcataaa acgggcgcaa caactggttt cggcgcctat gtcgccttta ttccggaaaa 1260
acaggtggcg attgtgattc tggcgaataa aaactacccg aataccgaaa gagtcaaagc 1320
tgcacaggct attttgagtg cactggaata aggatccctg tcagaccaag tttactcata 1380
tatactttag attgatttaa aacttcattt ttaatttaaa aggatctagg tgaagatcct 1440
ttttgataat ctcatgacca aaatccctta acgtgagttt tcgttccact gagcgtcaga 1500
ccccgtagaa aagatcaaag gatcttcttg agatcctttt tttctgcgcg taatctgctg 1560

-continued

```
cttgcaaaca aaaaaaccac cgctaccagc ggtggtttgt ttgccggatc aagagctacc   1620
aactcttttt ccgaaggtaa ctggcttcag cagagcgcag ataccaaata ctgtccttct   1680
agtgtagccg tagttaggcc accacttcaa gaactctgta gcaccgccta catacctcgc   1740
tctgctaatc ctgttaccag tggctgctgc cagtggcgat aagtcgtgtc ttaccgggtt   1800
ggactcaaga cgatagttac cggataaggc gcagcggtcg ggctgaacgg ggggttcgtg   1860
cacacagccc agcttggagc gaacgaccta caccgaactg agatacctac agcgtgagct   1920
atgagaaagc gccacgcttc ccgaagggag aaaggcggac aggtatccgg taagcggcag   1980
ggtcggaaca ggagagcgca cgagggagct tccaggggga aacgcctggt atctttatag   2040
tcctgtcggg tttcgccacc tctgacttga gcgtcgattt ttgtgatgct cgtcaggggg   2100
gcggagccta tggaaaaacg ccagcaacgc ggccttttta cggttcctgg ccttttgctg   2160
gccttttgct cacatgttct ttcctgcgtt atcccctgat tctgtggata accgtattac   2220
cgcctttgag tgagctgata ccgctcgccg cagccgaacg accgagcgca gcgagtcagt   2280
gagcgaggaa gcggaagagc gcctgatgcg gtattttctc cttacgcatc tgtgcggtat   2340
ttcacaccgc atttggtgca ctctcagtac aatctgctct gatgccgcat agttaagcca   2400
gtatacactc cgctatcgct acgtgactgg gtcatggctg cgccccgaca cccgccaaca   2460
cccgctgacg cgccctgacg ggcttgtctg ctcccggcat ccgcttacag acaagctgtg   2520
accgtctccg ggagctgcat gtgtcagagg ttttcaccgt catcaccgaa acgcgcgagg   2580
cagctgcggt aaagctcatc agcgtggtcg tgaagcgatt cacagatgtc tgcctgttca   2640
tccgcgtcca gctcgttgag tttctccaga agcgttaatg tctggcttct gataaagcgg   2700
gccatgttaa gggcggtttt ttcctgtttg gtcactgatg cctccgtgta agggggattt   2760
ctgttcatgg gggtaatgat accgatgaaa cgagagagga tgctcacgat acgggttact   2820
gatgatgaac atgcccggtt actggaacgt tgtgagggta aacaactggc ggtatggatg   2880
cggcgggacc agagaaaaat cactcagggt caatgccagc gcttcgttaa tacagatgta   2940
ggtgttccac agggtagcca gcagcatcct gcgatgcaga tccggaacat aatggtgcag   3000
ggcgctgact tccgcgtttc cagactttac gaaacacgga aaccgaagac cattcatgtt   3060
gttgctcagg tcgcagacgt tttgcagcag cagtcgcttc acgttcgctc gcgtatcggt   3120
gattcattct gctaaccagt aaggcaaccc cgccagccta gccgggtcct caacgacagg   3180
agcacgatca tgcgcacccg tggccaggac ccaacgctgc ccgagatgcg ccgcgtgcgg   3240
ctgctggaga tggcggacgc gatggatatg ttctgccaag ggttggtttg cgcattcaca   3300
gttctccgca agaattgatt ggctccaatt cttggagtgg tgaatccgtt agcgaggtgc   3360
cgccggcttc cattcaggtc gaggtggccc ggctccatgc accgcgacgc aacgcgggga   3420
ggcagacaag gtatagggcg gcgcctacaa tccatgccaa cccgttccat gtgctcgccg   3480
aggcggcata aatcgccgtg acgatcagcg gtccagtgat cgaagttagg ctggtaagag   3540
ccgcgagcga tccttgaagc tgtccctgat ggtcgtcatc tacctgcctg gacagcatgg   3600
cctgcaacgc gggcatcccg atgccgccgg aagcgagaag aatcataatg gggaaggcca   3660
tccagcctcg cgtcgcgaac gccagcaaga cgtagcccag cgcgtcggcc gccatgccgg   3720
cgataatggc ctgcttctcg ccgaaacgtt tggtggcggg accagtgacg aaggcttgag   3780
cgagggcgtg caagattccg aataccgcaa gcgacaggcc gatcatcgtc gcgctccagc   3840
gaaagcggtc ctcgccgaaa atgacccaga gcgctgccgg cacctgtcct acgagttgca   3900
tgataaagaa gacagtcata agtgcggcga cgatagtcat gccccgcgcc caccggaagg   3960
```

agctgactgg gttgaaggct ctcaagggca tcggtcgacg ctctccctta tgcgactcct 4020
gcattaggaa gcagcccagt agtaggttga ggccgttgag caccgccgcc gcaaggaatg 4080
gtgcatgcaa ggagatggcg cccaacagtc ccccggccac ggggcctgcc accataccca 4140
cgccgaaaca agcgctcatg agcccgaagt ggcgagcccg atcttcccca tcggtgatgt 4200
cggcgatata ggcgccagca accgcacctg tggcgccggt gatgccggcc acgatgcgtc 4260
cggcgtagag gattcacagg acgggtgtgg tcgccatgat cgcgtagtcg atagtggctc 4320
caagtagcga agcgagcagg actgggcggc ggccaaagcg gtcggacagt gctccgagaa 4380
cgggtgcgca tagaaattgc atcaacgcat atagcgctag cagcacgcca tagtgactgg 4440
cgatgctgtc ggaatggacg atatcccgca agaggcccgg cagtaccggc ataaccaagc 4500
ctatgcctac agcatccagg gtgacggtgc cgaggatgac gatgagcgca ttgttagatt 4560
tcatacacgg tgcctgactg cgttagcaat ttaactgtga taaactaccg cattaaagct 4620
tatcgatgat aagctgtcaa acatgagaa 4649

<210> SEQ ID NO 13
<211> LENGTH: 4664
<212> TYPE: DNA
<213> ORGANISM: Artificial Sequence
<220> FEATURE:
<223> OTHER INFORMATION: Synthetic construct: pBR-CBST-ADC-33

<400> SEQUENCE: 13
ttcttgaaga cgaaagggcc tcgtgatacg cctattttta taggttaatg tcatgataat 60
aatggtttct tagacgtcag gtggcacttt tcggggaaat gtgcgcggaa cccctatttg 120
tttatttttc taaatacatt caaatatgta tccgctcatg agacaataac cctgataaat 180
gcttcaataa tattgaaaaa ggaagagtca tatgcgattt aaaaaaattt cttgtctact 240
tttatccccg ctttttattt ttagtacctc aatttatgcg ggcaatacac caaaagacca 300
agaaattaaa aaactggtag atcaaaactt taaaccgtta ttagaaaaat atgatgtgcc 360
aggtatggct gtgggtgtta ttcaaaataa taaaaagtat gaaatgtatt atggtcttca 420
atctgttcaa gataaaaaag ccgtaaatag cagtaccatt tttgagctag gttctgtcag 480
taaattattt accgcgacag caggtggata tgcaaaaaat aaaggaaaaa tctcttttga 540
cgatacgcct ggtaaatatt ggaaagaact aaaaaacaca ccgattgacc aagttaactt 600
acttcaactc gcgacgtata caagtggtaa ccttgccttg cagtttccag atgaagtaaa 660
aacagaccaa caagttttaa ctttttttcaa agactggaaa cctaaaaact caatcggtga 720
atacagacaa tattcaaatc caagtattgg cctatttgga aaggttgtgg ctttgtctat 780
gaataaacct ttcgaccaag tcttagaaaa aacaattttt ccggcccttg gcttaaaaca 840
tagctatgta aatgtaccta agacccagat gcaaaactat gcatttggtt ataaccaaga 900
aaatcagccg attcgagtta accgcggccc actcgatgcc gcccctgcgt atggcgtcaa 960
atcgacacta cccgacatgt tgagttttat tcatgccaac cttaacccac agaaatatcc 1020
ggctgatatt caacgggcaa ttaatgaaac acatcaaggg cgctatcaag taaataccat 1080
gtatcaggca ctcggttggg aagagttttc ttatccggca acgttacaaa ctttattaga 1140
cagtaattca gaacagattg tgatgaaacc taataaagtg actgctattt caaaggaacc 1200
ttcagttaag atgtaccata aaactggctc aaccaacggt ttcggaacgt atgtagtgtt 1260
tattcctaaa gaaaatattg gcttagtcat gttaaccaat aaacgtattc caaatgaaga 1320

-continued gcgcattaag gcagcttatg ctgtgctgaa tgcaataaag aaataaggat ccctgtcaga 1380
ccaagtttac tcatatatac tttagattga tttaaaactt catttttaat ttaaaaggat 1440
ctaggtgaag atcctttttg ataatctcat gaccaaaatc ccttaacgtg agttttcgtt 1500
ccactgagcg tcagaccccg tagaaaagat caaaggatct tcttgagatc cttttttct 1560
gcgcgtaatc tgctgcttgc aaacaaaaaa accaccgcta ccagcggtgg tttgtttgcc 1620
ggatcaagag ctaccaactc tttttccgaa ggtaactggc ttcagcagag cgcagatacc 1680
aaatactgtc cttctagtgt agccgtagtt aggccaccac ttcaagaact ctgtagcacc 1740
gcctacatac ctcgctctgc taatcctgtt accagtggct gctgccagtg gcgataagtc 1800
gtgtcttacc gggttggact caagacgata gttaccggat aaggcgcagc ggtcgggctg 1860
aacggggggt tcgtgcacac agcccagctt ggagcgaacg acctacaccg aactgagata 1920
cctacagcgt gagctatgag aaagcgccac gcttcccgaa gggagaaagg cggacaggta 1980
tccggtaagc ggcagggtcg gaacaggaga gcgcacgagg gagcttccag ggggaaacgc 2040
ctggtatctt tatagtcctg tcgggtttcg ccacctctga cttgagcgtc gatttttgtg 2100
atgctcgtca ggggggcgga gcctatggaa aaacgccagc aacgcggcct ttttacggtt 2160
cctggccttt tgctggcctt ttgctcacat gttctttcct gcgttatccc ctgattctgt 2220
ggataaccgt attaccgcct ttgagtgagc tgataccgct cgccgcagcc gaacgaccga 2280
gcgcagcgag tcagtgagcg aggaagcgga agagcgcctg atgcggtatt ttctccttac 2340
gcatctgtgc ggtatttcac accgcatttg gtgcactctc agtacaatct gctctgatgc 2400
cgcatagtta agccagtata cactccgcta tcgctacgtg actgggtcat ggctgcgccc 2460
cgacacccgc caacacccgc tgacgcgccc tgacgggctt gtctgctccc ggcatccgct 2520
tacagacaag ctgtgaccgt ctccgggagc tgcatgtgtc agaggttttc accgtcatca 2580
ccgaaacgcg cgaggcagct gcggtaaagc tcatcagcgt ggtcgtgaag cgattcacag 2640
atgtctgcct gttcatccgc gtccagctcg ttgagtttct ccagaagcgt taatgtctgg 2700
cttctgataa agcgggccat gttaagggcg gttttttcct gtttggtcac tgatgcctcc 2760
gtgtaagggg gatttctgtt catgggggta atgataccga tgaaacgaga gaggatgctc 2820
acgatacggg ttactgatga tgaacatgcc cggttactgg aacgttgtga gggtaaacaa 2880
ctggcggtat ggatgcggcg ggaccagaga aaaatcactc agggtcaatg ccagcgcttc 2940
gttaatacag atgtaggtgt tccacagggt agccagcagc atcctgcgat gcagatccgg 3000
aacataatgg tgcagggcgc tgacttccgc gtttccagac tttacgaaac acggaaaccg 3060
aagaccattc atgttgttgc tcaggtcgca gacgttttgc agcagcagtc gcttcacgtt 3120
cgctcgcgta tcggtgattc attctgctaa ccagtaaggc aaccccgcca gcctagccgg 3180
gtcctcaacg acaggagcac gatcatgcgc acccgtggcc aggacccaac gctgcccgag 3240
atgcgccgcg tgcggctgct ggagatggcg gacgcgatgg atatgttctg ccaagggttg 3300
gtttgcgcat tcacagttct ccgcaagaat tgattggctc caattcttgg agtggtgaat 3360
ccgttagcga ggtgccgccg gcttccattc aggtcgaggt ggcccggctc catgcaccgc 3420
gacgcaacgc ggggaggcag acaaggtata gggcggcgcc tacaatccat gccaacccgt 3480
tccatgtgct cgccgaggcg gcataaatcg ccgtgacgat cagcggtcca gtgatcgaag 3540
ttaggctggt aagagccgcg agcgatcctt gaagctgtcc ctgatggtcg tcatctacct 3600
gcctggacag catggcctgc aacgcgggca tcccgatgcc gccggaagcg agaagaatca 3660
taatggggaa ggccatccag cctcgcgtcg cgaacgccag caagacgtag cccagcgcgt 3720

-continued

```
cggccgccat gccggcgata atggcctgct tctcgccgaa acgtttggtg gcgggaccag   3780
tgacgaaggc ttgagcgagg gcgtgcaaga ttccgaatac cgcaagcgac aggccgatca   3840
tcgtcgcgct ccagcgaaag cggtcctcgc cgaaaatgac ccagagcgct gccggcacct   3900
gtcctacgag ttgcatgata aagaagacag tcataagtgc ggcgacgata gtcatgcccc   3960
gcgcccaccg gaaggagctg actgggttga aggctctcaa gggcatcggt cgacgctctc   4020
ccttatgcga ctcctgcatt aggaagcagc ccagtagtag gttgaggccg ttgagcaccg   4080
ccgccgcaag gaatggtgca tgcaaggaga tggcgcccaa cagtcccccg gccacggggc   4140
ctgccaccat acccacgccg aaacaagcgc tcatgagccc gaagtggcga gcccgatctt   4200
ccccatcggt gatgtcggcg atataggcgc cagcaaccgc acctgtggcg ccggtgatgc   4260
cggccacgat gcgtccggcg tagaggattc acaggacggg tgtggtcgcc atgatcgcgt   4320
agtcgatagt ggctccaagt agcgaagcga gcaggactgg gcggcggcca aagcggtcgg   4380
acagtgctcc gagaacgggt gcgcatagaa attgcatcaa cgcatatagc gctagcagca   4440
cgccatagtg actggcgatg ctgtcggaat ggacgatatc ccgcaagagg cccggcagta   4500
ccggcataac caagcctatg cctacagcat ccagggtgac ggtgccgagg atgacgatga   4560
gcgcattgtt agatttcata cacggtgcct gactgcgtta gcaatttaac tgtgataaac   4620
taccgcatta aagcttatcg atgataagct gtcaaacatg agaa                    4664
```